US006764686B2

(12) United States Patent
Minetti et al.

(10) Patent No.: US 6,764,686 B2
(45) Date of Patent: Jul. 20, 2004

(54) MODIFIED IMMUNOGENIC PNEUMOLYSIN COMPOSITIONS AS VACCINES

(75) Inventors: Conceicao Minetti, Silver Spring, MD (US); Francis Michon, Bethesda, MD (US); Jeffrey K. Pullen, Columbia, MD (US); Mary Ellen Polvino-Bodnar, Annapolis, MD (US); Shu-Mei Liang, Taipei (TW); Joseph Y. Tai, Collegeville, PA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/120,044

(22) Filed: Jul. 21, 1998

(65) Prior Publication Data

US 2001/0014332 A1 Aug. 16, 2001

Related U.S. Application Data

(60) Provisional application No. 60/073,456, filed on Feb. 2, 1998, and provisional application No. 60/053,306, filed on Jul. 21, 1997.

(51) Int. Cl.[7] .................. A61K 39/02; A61K 39/09; A61K 39/385; A61K 39/116; A61K 39/38

(52) U.S. Cl. .................. 424/236.1; 424/234.1; 424/244.1; 424/190.1; 424/194.1; 424/197.11; 424/203.1; 424/184.1; 424/185.1; 424/831; 530/350; 530/825

(58) Field of Search .................. 424/236.1, 234.1, 424/244.1, 184.1, 190.1, 194.1, 197.11, 193.1, 185.1, 831, 266.1, 9.2, 9.322, 196.1, 203.1; 530/350, 825

(56) References Cited

U.S. PATENT DOCUMENTS

| 5,565,204 A | 10/1996 | Kuo et al. .............. 424/244.1 |
| 5,623,057 A | 4/1997 | Marburg et al. ........... 530/404 |
| 6,019,982 A | * 2/2000 | Clements et al. ......... 424/236.1 |

FOREIGN PATENT DOCUMENTS

| EP | 0 687 688 A1 | 12/1995 |
| WO | WO 95/16711 | 6/1995 |
| WO | WO 96/05859 | 2/1996 |
| WO | WO 98/06851 | * 2/1998 |
| WO | WO 90/06951 | 6/1999 |

OTHER PUBLICATIONS

Krishnamurthy et al. Infect. Immun. 22: 727–735, 1978.*
Lee et al. J. Infect. Dis. 151: 658–664, 1985.*
Lee et al. Vaccine 12: 875–878, 1994.*
Berry et al. Infect. Immun. 63: 1969–1974, 1995.*
Feldman et al. Am. J. Respir. Cell Mol. Biol. 5: 416–423, 1991.*
Mitchell et al. Mol. Microbiol. 5: 1883–1888, 1991.*
Alexander et al. Microb. Pathogen. 24: 167–174, 1998.*
Rossjohn et al. J. Mol. Biol. 284: 449–461, 1998.*
Pizza et al. Mol. Microbiol. 14: 51–60, 1994.*
McGuinnes et al. Lancet 337: 514–517, 1991.*
Lazar et al. Mol. Cell. Biol. 8: 1247–1252, 1988.*
Houghten et al. In: Vaccines86, Cold Spring Harbor Laboratory, p. 21–25, 1986.*
McGuinnes et al. Mol. Microbiol. 7: 505–514, 1993.*
Peter J. Morgan, et al., Structural and functional characterisation of two proteolytic fragments of the bacterial protein toxin, pneumolysin, *FEBS Letters*, vol. 412, No. 3, Aug. 4, 1997, pp. 563–567.
Jamie Rossjohn, et al., Structure of a Cholesterol–Binding, Thiol–Activated Cytolysin and a Model of Its Membrane Form, *Cell*, vol. 89, May 30, 1997, pp. 685–692.
Robert A. Lock, et al., Sequence variation in the *Streptococcus pneumoniae* pneumolysin gene affecting haemolytic activity and electrophoretic mobility of the toxin, *Microbial Pathogenesi*s, vol. 21, 1996, pp. 71–83.
Joseph Kuo, et al., Characterization of a Recombinant Pneumolysin and Its Use as a Protein Carrier for Pneumococcal Type 18C Conjugate Vaccines, *Infection and Immunity*, vol. 63, No. 7, Jul. 1995, pp. 2706–2713.
Jay C. Butler, et al., Serotype Distribution of *Streptococcus pneumoniae* Infections among preschool Children in the United States, 1978–1994: Implications for development of a Conjugate Vaccine, *The Journal of Infectious Diseases*, vol. 171, No. 4, Apr. 1995, pp. 885–889.
Janet E. Alexander, et al., Immunization of Mice with Pneumolysin Toxoid Confers a Significant Degree of Protection against At Least Nine Serotypes of *Streptococcus pneumoniae*, *Infection and Immunity*, vol. 62, No. 12, Dec. 1994, pp. 5683–5688.

(List continued on next page.)

Primary Examiner—S. Devi
(74) Attorney, Agent, or Firm—Morgan & Finnegan, L.L.P.; Kenneth H. Sonnenfeld

(57) ABSTRACT

This invention relates to modified pneumolysin polypeptides that retain the immunogenic nature of pneumolysin but have reduced or undetectable hemolytic activity compared to native pneumolysin. The invention also provides a method for generating novel pneumolysin variants with these desired characteristic properties. The invention also provides immunogenic compositions useful as pharmaceutical compositions including vaccines in which non-toxic, modified pneumolysin is used to stimulate protective immunity against *Streptococcus pneumoniae*. The vaccines may be compositions in which the modified pneumolysin is conjugated to bacterial polysaccharides or may be carried on an attenuated viral vector. In addition, the invention also provides a method of using the non-toxic, modified pneumolysin toxoid in order to stimulate antibodies against *Streptococcus pneumoniae* in a treated individual which are then isolated and transferred to a second individual, thereby conferring protection against *Streptococcus pneumoniae* in the second individual.

34 Claims, 23 Drawing Sheets

OTHER PUBLICATIONS

Jim Hill, et al., Amino Acids in Pneumolysin Important for Hemolytic Activity Identified by Random Mutagenesis, *Infection and Immunity*, vol. 62, No. 2, Feb. 1994, pp. 757–758.

Gianfranco Menestrina, et al., Structural features of the pore formed by *Staphylococcus aureus* α–toxin inferred form chemical modification and primary structure analysis, *FEMS Microbiology Immunology, Infection: Host Response and Immunity*, vol. 105, Nos. 1–3, Sep. 1992, pp. 19–28.

James C. Paton, et al., Purification and Immunogenicity of Genetically Obtained Pneumolysin Toxids and Their Conjugation to *Streptococcus pneumoniae* Type 19F Polysaccharide, *Infection and Immunity*, vol. 59, No. 7, Jul. 1991, pp. 2297–2304.

Margaret J. Green, et al., Site–Directed Mutagenesis of the Hole–Forming Toxin Aerolysin: Studies on the Roles of Histidines in Receptor Binding and Oligomerization of the Monomer, *Biochemistry*, vol. 29, No. 8, Feb. 27, 1990, pp. 2177–2180.

Abstract W–PM–B4, A.S.A. Minetti, et al., Structural And Functional Characterization of Recombinant Streptococcal Pneumolysin, Biophysical J., vol. 74, No. 2, Feb. 1998, p. A233.

F. Michon, et al., Multivalent pneumococcal capsular polysaccharide conjugate vaccines employing genetically detoxified pneumolysin as a carrier protein, *Vaccine*, vol. 16, No. 18, Nov. 1998, pp. 1732–1741.

\* cited by examiner

| | | | | |
|---|---|---|---|---|
| ATGGCAAATA | AAGCAGTAAA | TGACTTTATA | CTAGCTATGA | 40 |
| ATTACGATAA | AAAGAAACTC | TTGACCCATC | AGGGAGAAAG | 80 |
| TATTGAAAAT | CGTTTCATCA | AAGAGGGTAA | TCAGCTACCC | 120 |
| GATGAGTTTG | TTGTTATCGA | AAGAAAGAAG | CGGAGCTTGT | 160 |
| CGACAAATAC | AAGTGATATT | TCTGTAACAG | CTACCAACGA | 200 |
| CAGTCGCCTC | TATCCTGGAG | CACTTCTCGT | AGTGGATGAG | 240 |
| ACCTTGTTAG | AGAATAATCC | CACTCTTCTT | GCGGTCGATC | 280 |
| GTGCTCCGAT | GACTTATAGT | ATTGATTTGC | CTGGTTTGGC | 320 |
| AAGTAGCGAT | AGCTTTCTCC | AAGTGGAAGA | TCCCAGCAAT | 360 |
| TCAAGTGTTC | GCGGAGCGGT | AAACGATTTG | TTGGCTAAGT | 400 |
| GGCATCAAGA | TTATGGTCAG | GTCAATAATG | TCCCAGCTAG | 440 |
| AATGCAGTAT | GAAAAAATCA | CGGCTCACAG | CATGGAACAA | 480 |
| CTCAAGGTCA | AGTTTGGTTC | TGACTTTGAA | AAGACAGGGA | 520 |
| ATTCTCTTGA | TATTGATTTT | AACTCTGTCC | ATTCAGGCGA | 560 |
| AAAGCAGATT | CAGATTGTTA | ATTTTAAGCA | GATTTATTAT | 600 |
| ACAGTCAGCG | TAGACGCTGT | TAAAAATCCA | GGAGATGTGT | 640 |
| TTCAAGATAC | TGTAACGGTA | GAGGATTTAA | AACAGAGAGG | 680 |
| AATTTCTGCA | GAGCGTCCTT | TGGTCTATAT | TTCGAGTGTT | 720 |
| GCTTATGGGC | GCCAAGTCTA | TCTCAAGTTG | GAAACCACGA | 760 |
| GTAAGAGTGA | TGAAGTAGAG | GCTGCTTTTG | AAGCTTTGAT | 800 |
| AAAAGGAGTC | AAGGTAGCTC | CTCAGACAGA | GTGGAAGCAG | 840 |
| ATTTTGGACA | ATACAGAAGT | GAAGGCGGTT | ATTTTAGGGG | 880 |
| GCGACCCAAG | TTCGGGTGCC | CGAGTTGTAA | CAGGCAAGGT | 920 |
| GGATATGGTA | GAGGACTTGA | TTCAAGAAGG | CAGTCGCTTT | 960 |

FIG. 1A

| | | | | |
|---|---|---|---|---|
| ACAGCAGATC | ATCCAGGCTT | GCCGATTTCC | TATACAACTT | 1000 |
| CTTTTTTACG | TGACAATGTA | GTTGCGACCT | TTCAAAATAG | 1040 |
| TACAGACTAT | GTTGAGACTA | AGGTTACAGC | TTACAGAAAC | 1080 |
| GGAGATTTAC | TGCTGGATCA | TAGTGGTGCC | TATGTTGCCC | 1120 |
| AATATTATAT | TACTTGGAAT | GAATTATCCT | ATGATCATCA | 1160 |
| AGGTAAGGAA | GTCTTGACTC | CTAAGGCTTG | GACAGAAAT | 1200 |
| GGGCAGGATT | TAACGGCTCA | CTTTACCACT | AGTATTCCTT | 1240 |
| TAAAAGGGAA | TGTTCGTAAT | CTCTCTGTCA | AAATTAGAGA | 1280 |
| GTGTACCGGG | CTTGCTTGGG | AATGGTGGCG | TACGGTTTAT | 1320 |
| GAAAAACCG | ATTTGCCACT | AGTGCGTAAG | CGGACGATTT | 1360 |
| CTATTTGGGG | AACAACTCTC | TATCCGCAGG | TAGAAGATAA | 1400 |
| GGTAGAAAAT | GAC | | | 1413 |

FIG. 1B

| | |
|---|---:|
| ATGGCAAATA AAGCAGTAAA TGACTTTATA CTAGCTATGA | 40 |
| ATTACGATAN$_{50}$ AAAN$_{54}$AAACTC TTGACCCATC AGGGAGAAAG | 80 |
| TATTGAAAAT CGTTTCAN$_{98}$CA AAGAGGGTAA TCAGCTACCC | 120 |
| GN$_{122}$TGAGTTTG TTGN$_{134}$TAN$_{137}$CGA AGAAAGAAG CGGAGCTTGT | 160 |
| CGACAAATAC AAGTGATATT N$_{181}$CTGTAN$_{187}$CAG CTACCN$_{196}$ACGA | 200 |
| CAGTCGCCTC TATCCTGGAG CACTTCTCGT AGTGGATGAG | 240 |
| ACCTTGTN$_{248}$AG AGAATAATCC CACTCTTCTT GCGGTN$_{276}$GATC | 280 |
| GTGCTCCGAT GACTTATAGT AN$_{302}$TGN$_{305}$TTTGC CTGGTTTGGC | 320 |
| AAGTAGCGAT AGCTTCTCC AAGTGGAAGA N$_{351}$CCCAGCAAT | 360 |
| TCAAGTGTTC GCGGAGCGGN$_{380}$ AN$_{382}$ACGATTTG TTGGCTAAGT | 400 |
| GGCATCAAGA TTATGGTCAG GTCAATAATG TCCCAGCTAG | 440 |
| AAN$_{443}$GCAGTAT GAAAAAATN$_{459}$A CGGCTCACAG CATGGAACAA | 480 |
| CTCAAGGTCA AGTTTGGTTC TGACTTTGAA AAGN$_{514}$CAGGGA | 520 |
| ATTCTCTTGA TATTGATTTT AACTCTGTCC ATTCAGGN$_{558}$GA | 560 |
| AAAGCN$_{566}$GATT CAGATTGTTA ATN$_{583}$TTAAGCA GATTTATTAT | 600 |
| ACAGTCAGCG TAGACGCTGT TAAAAATCCA GGAGATGTGT | 640 |
| TTCAAGATAC TGTAACGGTA GAGGATTTAA AACAGAGAGG | 680 |
| AATTTCTGCA GAGCGTCCTT TGGTCTATAT TTCGAGN$_{717}$GTT | 720 |
| GCTTATGGGC GCCAAGTCTA TCTCAAGTTG GAAACCACGA | 760 |
| GTAN$_{764}$GAGTGN$_{770}$ TGAAGTAGAG GCTGCTTTTG AAGCTTTGAT | 800 |
| AAAAGGAGTC AAGGTAGCTC CTCAGACAGA GTGGAAGCAG | 840 |
| ATTTTGGACA ATACAGAAGT GAAGGCGGTT ATTTAGGGG | 880 |
| GCGACCCAAG TTCGGGTGCC CGAGTTGTAA CAGGCAAGGT | 920 |
| GGATATGGTA GAGGACTTGA TTCAAGAAGG CAGTCGCTTT | 960 |
| ACAGCAGATC ATCCAGGCTT GCCGATTTCC TATACAACTT | 1000 |

FIG. 2A

```
CTTTTTTACG TGACAATGTA GTTGCGACCT TTCAAAAN₁₀₃₈AG        1040
TACAGACTAT GTTGAGACTA AGGTTACAGC TTACAGAAAC            1080
GGAGATTTAC TGCTGGATCA TAGTGGTGCC TATGTTGCCC            1120
AATATTATAT TACTTGGN₁₁₃₈AT GAATTATCCT ATGATCATCA        1160
AGGTAAGGAA GTCTTGACTC CTAAGGCTTG GGACAGAAAT            1200
GGGCAGGATT TN₁₂₁₂ACGGCTCA CTTTACCACT AGTATTCCTT        1240
TAAAAGGGAA TGTTCGTAAT CTCTCTGTCA AAATTAGAGA            1280
GTGTACCGGG CTTGCN₁₂₉₆TGGG AATGGTGGCG TACGGTTTAT        1320
GAAAAACCG ATTTGCCACT AGTGCGTAAG CGGACGATTT             1360
CTATTTGGGG AACAACTCTC TATCCN₁₃₈₆CAGG TAGAN₁₃₉₅GATAA    1400
GGTAGAAAAT GAC                                         1413
```

FIG. 2B

| | | | | | | | | | |
|---|---|---|---|---|---|---|---|---|---|
| Met 1 | Ala | Asn | Lys | Ala 5 | Val | Asn | Asp | Phe | Ile 10 | Leu | Ala |
| Met | Asn | Tyr 15 | Asp | Lys | Lys | Lys | Leu 20 | Leu | Thr | His | Gln |
| Gly 25 | Glu | Ser | Ile | Glu | Asn 30 | Arg | Phe | Ile | Lys | Glu 35 | Gly |
| Asn | Gln | Leu | Pro 40 | Asp | Glu | Phe | Val | Val 45 | Ile | Glu | Arg |
| Lys | Lys 50 | Arg | Ser | Leu | Ser | Thr 55 | Asn | Thr | Ser | Asp | Ile 60 |
| Ser | Val | Thr | Ala | Thr 65 | Asn | Asp | Ser | Arg | Leu 70 | Tyr | Pro |
| Gly | Ala | Leu 75 | Leu | Val | Val | Asp | Glu 80 | Thr | Leu | Leu | Glu |
| Asn 85 | Asn | Pro | Thr | Leu | Leu 90 | Ala | Val | Asp | Arg | Ala 95 | Pro |
| Met | Thr | Tyr | Ser 100 | Ile | Asp | Leu | Pro | Gly 105 | Leu | Ala | Ser |
| Ser | Asp 110 | Ser | Phe | Leu | Gln | Val 115 | Glu | Asp | Pro | Ser | Asn 120 |
| Ser | Ser | Val | Arg | Gly 125 | Ala | Val | Asn | Asp | Leu 130 | Leu | Ala |
| Lys | Trp | His 135 | Gln | Asp | Tyr | Gly | Gln 140 | Val | Asn | Asn | Val |
| Pro 145 | Ala | Arg | Met | Gln | Tyr 150 | Glu | Lys | Ile | Thr | Ala 155 | His |
| Ser | Met | Glu | Gln 160 | Leu | Lys | Val | Lys | Phe 165 | Gly | Ser | Asp |
| Phe | Glu 170 | Lys | Thr | Gly | Asn | Ser 175 | Leu | Asp | Ile | Asp | Phe 180 |
| Asn | Ser | Val | His | Ser 185 | Gly | Glu | Lys | Gln | Ile 190 | Gln | Ile |
| Val | Asn | Phe 195 | Lys | Gln | Ile | Tyr | Tyr 200 | Thr | Val | Ser | Val |
| Asp 205 | Ala | Val | Lys | Asn | Pro 210 | Gly | Asp | Val | Phe | Gln 215 | Asp |
| Thr | Val 220 | Thr | Val | Glu | Asp | Leu | Lys | Gln 225 | Arg | Gly | Ile |
| Ser | Ala | Glu 230 | Arg | Pro | Leu | Val 235 | Tyr | Ile | Ser | Ser | Val 240 |
| Ala | Tyr | Gly | Arg | Gln 245 | Val | Tyr | Leu | Lys | Leu 250 | Glu | Thr |
| Thr | Ser | Lys 255 | Ser | Asp | Glu | Val | Glu 260 | Ala | Ala | Phe | Glu |
| Ala 265 | Leu | Ile | Lys | Gly | Val 270 | Lys | Val | Ala | Pro | Gln 275 | Thr |
| Glu | Trp | Lys | Gln 280 | Ile | Leu | Asp | Asn | Thr 285 | Glu | Val | Lys |

FIG. 3A

```
Ala Val Ile Leu Gly Gly Asp Pro Ser Ser Gly Ala
    290             295                 300
Arg Val Val Thr Gly Lys Val Asp Met Val Glu Asp
            305                 310
Leu Ile Gln Glu Gly Ser Arg Phe Thr Ala Asp His
            315             320
Pro Gly Leu Pro Ile Ser Tyr Thr Thr Ser Phe Leu
325             330                 335
Arg Asp Asn Val Val Ala Thr Phe Gln Asn Ser Thr
            340             345
Asp Tyr Val Glu Thr Lys Val Thr Ala Tyr Arg Asn
    350             355                 360
Gly Asp Leu Leu Leu Asp His Ser Gly Ala Tyr Val
            365             370
Ala Gln Tyr Tyr Ile Thr Trp Asn Glu Leu Ser Tyr
    375             380
Asp His Gln Gly Lys Glu Val Leu Thr Pro Lys Ala
385             390                 395
Trp Asp Arg Asn Gly Gln Asp Leu Thr Ala His Phe
            400             405
Thr Thr Ser Ile Pro Leu Lys Gly Asn Val Arg Asn
    410             415                 420
Leu Ser Val Lys Ile Arg Glu Cys Thr Gly Leu Ala
                425                 430
Trp Glu Trp Trp Arg Thr Val Tyr Glu Lys Thr Asp
        435                 440
Leu Pro Leu Val Arg Lys Arg Thr Ile Ser Ile Trp
445             450                 455
Gly Thr Thr Leu Tyr Pro Gln Val Glu Asp Lys Val
            460                 465
Glu Asn Asp
470
```

FIG. 3B

| | | | | | | | | | |
|---|---|---|---|---|---|---|---|---|---|
| Met 1 | Ala | Asn | Lys | Ala 5 | Val | Asn | Asp | Phe | Ile 10 | Leu | Ala |
| Met | Asn | Tyr 15 | Asp | Xaa | Xaa | Lys | Leu | Leu 20 | Thr | His | Gln |
| Gly 25 | Glu | Ser | Ile | Glu | Asn 30 | Arg | Phe | Xaa | Lys | Glu 35 | Gly |
| Asn | Gln | Leu | Pro 40 | Xaa | Glu | Phe | Val | Xaa 45 | Xaa | Glu | Arg |
| Lys | Lys 50 | Arg | Ser | Leu | Ser | Thr 55 | Asn | Thr | Ser | Asp | Ile 60 |
| Xaa | Val | Xaa | Ala | Thr 65 | Xaa | Asp | Ser | Arg | Leu 70 | Tyr | Pro |
| Gly | Ala | Leu 75 | Leu | Val | Val | Asp | Glu 80 | Thr | Xaa | Leu | Glu |
| Asn 85 | Asn | Pro | Thr | Leu | Leu 90 | Ala | Val | Asp | Arg | Ala 95 | Pro |
| Met | Thr | Tyr | Ser 100 | Xaa | Xaa | Leu | Pro | Gly 105 | Leu | Ala | Ser |
| Ser | Asp 110 | Ser | Phe | Leu | Gln | Val 115 | Glu | Asp | Pro | Ser | Asn 120 |
| Ser | Ser | Val | Arg | Gly 125 | Ala | Xaa | Xaa | Asp | Leu 130 | Leu | Ala |
| Lys | Trp | His 135 | Gln | Asp | Tyr | Gly | Gln 140 | Val | Asn | Asn | Val |
| Pro 145 | Ala | Arg | Xaa | Gln | Tyr 150 | Glu | Lys | Xaa | Thr | Ala 155 | His |
| Ser | Met | Glu | Gln 160 | Leu | Lys | Val | Lys | Phe 165 | Gly | Ser | Asp |
| Phe | Glu 170 | Lys | Xaa | Gly | Asn | Ser 175 | Leu | Asp | Ile | Asp | Phe 180 |
| Asn | Ser | Val | His | Ser 185 | Gly | Glu | Lys | Xaa | Ile 190 | Gln | Ile |
| Val | Asn | Xaa 195 | Lys | Gln | Ile | Tyr | Tyr 200 | Thr | Val | Ser | Val |
| Asp 205 | Ala | Val | Lys | Asn | Pro 210 | Gly | Asp | Val | Phe | Gln 215 | Asp |
| Thr | Val 220 | Thr | Val | Glu | Asp | Leu | Lys | Gln 225 | Arg | Gly | Ile |
| Ser | Ala 230 | Glu | Arg | Pro | Leu | Val 235 | Tyr | Ile | Ser | Xaa | Val 240 |
| Ala | Tyr | Xaa | Arg | Gln 245 | Val | Tyr | Leu | Lys | Leu 250 | Glu | Thr |
| Thr | Ser | Xaa 255 | Ser | Xaa | Glu | Val | Glu 260 | Ala | Ala | Phe | Glu |
| Ala 265 | Leu | Ile | Lys | Gly | Val 270 | Lys | Val | Ala | Pro | Gln 275 | Thr |
| Glu | Trp | Lys | Gln 280 | Ile | Leu | Asp | Asn | Thr 285 | Xaa | Val | Lys |

FIG. 4A

```
Ala Val Ile Leu Gly Gly Asp Pro Ser Ser Gly Ala
    290                 295                 300
Arg Val Val Thr Gly Lys Val Asp Met Val Glu Asp
            305                 310
Leu Ile Gln Glu Gly Ser Arg Phe Thr Ala Asp His
        315                 320
Pro Gly Leu Pro Ile Ser Tyr Thr Thr Ser Phe Leu
325                 330                 335
Arg Asp Asn Val Val Ala Thr Phe Gln Asn Ser Thr
            340                 345
Asp Tyr Val Glu Thr Lys Val Thr Ala Tyr Arg Asn
    350                 355                 360
Gly Asp Leu Leu Leu Asp His Ser Gly Ala Tyr Val
            365                 370
Ala Gln Tyr Tyr Ile Thr Trp Xaa Glu Leu Ser Tyr
        375                 380
Asp His Gln Gly Lys Glu Val Leu Thr Pro Lys Ala
385                 390                 395
Trp Asp Arg Asn Gly Gln Asp Leu Thr Ala His Phe
            400                 405
Thr Thr Ser Ile Pro Leu Lys Gly Asn Val Arg Asn
    410                 415                 420
Leu Ser Val Lys Ile Arg Glu Cys Thr Gly Leu Ala
            425                 430
Trp Glu Trp Trp Arg Thr Val Tyr Glu Lys Thr Asp
        435                 440
Leu Xaa Leu Val Arg Lys Arg Thr Ile Ser Ile Trp
445                 450                 455
Gly Thr Thr Leu Tyr Pro Gln Val Glu Asp Lys Val
            460                 465
Glu Asn Asp
    470
```

FIG. 4B

MODIFIED IMMUNOGENIC PNEUMOLYSIN COMPOSITIONS AS VACCINES

The instant application claims domestic priority to the provisional applications, 60/073,456 filed Feb. 2, 1998 and 60/053,306 filed Jul. 21, 1997.

FIELD OF THE INVENTION

This invention relates to the field of vaccines, and in particular, methods for the production of modified forms of pneumolysin and their use in producing compositions for the immunization of mammals against infections caused by bacteria including *Streptococcus pneumoniae.*

BACKGROUND OF THE INVENTION

*Streptococcus pneumoniae* is the major cause of bacterial pneumonia, bacteremia, meningitis, and otitis media (Baltimore et al. in *Bacterial infections of humans: Epidemiology and control* Evans and Brachman eds, Plenum Press, New York, 1989 pp.525–546; Schuchat et al. *N. Engl. J. Med.* 1997, 337, 970–976). Even with appropriate antibiotic therapy, pneumococcal infections have been estimated to result in as many as 40,000 deaths a year in the United States (Fedson et al. *Archives of Internal Medicine* 1994, 154, 2531–2535; Fiebach et al. *Archives of Internal Medicine* 1994, 154, 2545–2557). In addition, pneumococci have gained increased resistance to penicillin and other antibiotics making the development of an effective vaccine to prevent pneumococcal infections a public health priority (Farr et al. *Archives of Internal Medicine* 1995, 155, 2336–2340). Since the current 23-valent pneumococcal capsular polysaccharide vaccine is ineffective in children less than two years old (Douglas et al. *J Infect Dis* 1983, 148, 131–137; Leinonen et al. *Pediatric Infectious Disease Journal* 1986, 5, 39–44), numerous groups are developing multivalent conjugate vaccines to prevent otitis media, the major indication in this age group.

Pneumolysin (PLY), a sulfydryl-activated cytolytic toxin, is produced by all types of *Streptococcus pneumoniae* (Kanclerski et al. *J Clin Microbiol* 1987, 25, 222–225) and is considered a major virulence factor in pneumococcal infection (Boulnois *Journal of General Microbiology* 1992, 138, 249–259). Genetically engineered PLY-negative mutant strains of *S. pneumoniae* have been shown to be significantly less virulent in mice (Berry et al. *Microb Pathog* 1992, 12, 87–93; Berry et al. *Infection and Immunity* 1989, 57, 2037–2042). Cytotoxicity of PLY to pulmonary endothelial and epithelial cells is well demonstrated in vitro (Rubins et al. *Infection and Immunity* 1992, 60, 1740–1746). In addition, PLY may be the principal cause of hearing loss and cochlear damage in a guinea pig model of pneumococcal meningitis (Winter et al. *Infection and Immunity* 1997, 65, 4411–4418).

As of 1985, an estimated five million children under the age of 5 died from pneumonia caused by *S. pneumoniae* in developing countries each year. *Lancet* (1985) Sep 28 2(8457):699–701. *S. pneumoniae* employs a number of virulence factors to establish an initial infection and then produce invasive disease(s). To prevent systemic infections caused by the various serotypes of *S. pneumoniae,* immunization of infants and adults with suitable, cross-reactive vaccines, capable of eliciting safe, effective, and long-lasting immunity, is needed.

In a prospective study of pneumococcal colonization and infection in children, it was reported that pneumococcal serotypes 6, 14, 19, and 23 are the most commonly carried as well as the most frequent cause of infection in infants, mainly otitis media (Gray et al. *J. Infect. Dis.,* 1988, 158, 948–955). In addition, it was recently found that these same strains are more frequent among the penicillin resistant clinical isolates (Nesin et al. *J. Infect. Dis.,* 1998, 177, 707–713). Clinical studies carried out in young infants with a tetravalent pneumococcal conjugate vaccine including the above types, report a reduction in the carriage of vaccine-related strains (Dagan et al. *Infect. Dis. J.,* 1997, 16, 1060–1064).

Almost all isolates of *S. pneumoniae* exhibit an external capsule made up of repeating oligosaccharides. Antigenic differences in the capsular polysaccharides due to different saccharide sequences are the hallmark of the different *S. pneumoniae* serotypes. Serotype-specific capsular polysaccharides are the major contributors to the virulence of the pneumococcus. Existing anti-pneumococcal vaccines are formulated from 23 capsular polysaccharides selected from the 84 serologically distinct types currently recognized. Unfortunately, these vaccines are not effective in all populations, especially those of Asia. A second shortcoming of the current vaccines is that polysaccharides by themselves are poor immunogens, especially for infants and the elderly.

Polypeptides expressed by *S. pneumoniae* also play an important pathogenic role. Some of the defined polypeptides that appear to contribute to the virulence of this organism include pneumolysin, autolysin, neuraminidase, pneumococcal surface polypeptide A (PspA), the 37 kDa polypeptide, adhesion molecules, hyaluronidase, and an IgA1 protease.

Virtually all serotypes of *S. pneumoniae* produce pneumolysin, one of the major virulence factors. This expression by the various *S. pneumoniae* serotypes makes pneumolysin a prime candidate for use in a protective vaccine against pneumococcal infections provided its toxicity can be altered.

Pneumolysin is an intracellular bacterial polypeptide with a molecular weight of approximately 53-kD. (Kanclerski et al. (1987) *J. Clin. Microbiol.* 25:222–225.) It is a member of a family of thiol-activated hemolysins and has various effects on eukaryotic cells. Pneumolysin is known to bind to cholesterol molecules in the eukaryotic membrane, form oligomers, and generate transmembrane pores. It has also been demonstrated that the respiratory burst, chemotactic, and phagocytic functions of polymorphonuclear leukocytes, all of which are critically important for removing invading pneumococci, are severely compromised in the presence of pneumolysin.

Pneumolysin causes both cytolytic and cytotoxic effects, and can stimulate an inflammatory response by the complement activation pathway. Nonspecific activation of complement causes depletion of complement polypeptides and generates nonspecific inflammation. Inoculation of pneumolysin into lungs of experimental animals causes pneumoniae-like symptoms. However, pre-immunization with pneumolysin is protective for experimental animals upon challenge with pneumococci. Paton et al. (1983) *Infect. Immun.* 40:548–552.

Because of pneumolysin's immunogenic activity and capacity to elicit a protective response in individuals immunized with it, it has been suggested to use pneumolysin as a component of a vaccine. See PCT/AU89/00539. However, before pneumolysin can be included in vaccines for human use, this toxin must be modified so as to be substantially non-toxic while retaining the capacity to elicit protective antibodies.

Modified pneumolysins devoid of toxic activities are reported to have been generated based on the identification of amino acid regions of pneumolysin thought to have similar functions to related thiol-containing polypeptides. (WO 90/06951). The reported mutations are exclusively in the C-terminal portion of the polypeptide and were generated using targeted mutagenesis techniques. Other mutations, including certain specific amino acids in the N-terminal region have been reported to reduce hemolytic activity. The most significant reduction in hemolytic activity is reported as possibly being a result of histidine modification at position 156. Hill et al. (1994) *Infection and Immunity*, 62, 757–758. No data is provided concerning whether any of these substituted pneumolysins were properly refolded. A single mutation, Thr-172→Ile was reported to be responsible for a pneumolysin with reduced hemolytic activity. However, anomalous electrophoretic mobility indicates that the protein is incorrectly folded. Lock et al. *Microb. Pathog.* (1996) 21, 71–83.

SUMMARY OF THE INVENTION

This invention provides a novel method for generating and identifying stable, genetically modified, substantially non-toxic, immunogenic pneumolysin polypeptides using random PCR mutagenesis. Modified pneumolysin (pneumolysoid) which can be used as immunogens in a vaccine or can be used as an immunogenic carrier polypeptide for polysaccharide conjugate vaccines against *S. pneumoniae* or other bacterial infections are also provided. The modified pneumolysin polypeptides of this invention, while exhibiting substantially reduced or none of the toxin's toxic activity, elicit antibodies which are cross-reactive with those elicited by the native toxin.

This invention also relates to nucleic acid sequences encoding the modified pneumolysins, vectors containing them as well as transformed host cells capable of expressing the nucleic acid molecules of this invention.

Another embodiment of this invention is polysaccharide-polypeptide conjugate molecules in which the modified pneumolysin of this invention is covalently coupled to bacterial polysaccharide to form the conjugate. Such conjugate molecules are useful as immunogens for eliciting a T cell dependent immunogenic response directed against the bacterial polysaccharide conjugated to the modified pneumolysin.

The invention is further directed to pharmaceutical compositions containing the modified pneumolysin polypeptides of the invention which elicit an immune response.

This invention further relates to a method of eliciting the production of antibodies reactive to the modified pneumolysin polypeptides. Such antibodies may be used to elicit both active and passive immunity. The modified pneumolysins of this invention may also be used to identify and isolate reactive antibodies.

It is therefore an object of this invention to provide genetically stable, modified *S. pneumoniae* pneumolysin polypeptides which have substantially attenuated or absent toxicity while retaining epitopes which cause production of antibodies which also bind the native toxin molecule.

It is a further object of this invention to provide a method for generating genetically modified pneumolysins (pneumolysoids).

It is another object of this invention to provide vaccine preparations comprising a modified pneumolysin polypeptide that can elicit antibodies and induce protective immunity against *Streptococcus pneumoniae* when delivered to a susceptible mammal. Such vaccines may be based on the pneumolysoid itself, or conjugates that comprise one or more bacterial polysaccharides covalently bound to a modified pneumolysin polypeptide of this invention.

BRIEF DESCRIPTION OF THE DRAWINGS

FIGS. 1A and 1B Wild-type nucleic acid sequence of type 14 pneumolysin (SEQ ID NO: 1).

FIGS. 2A and 2B Non-limiting nucleic acid variations of type 14 pneumolysin (SEQ ID NO: 2). The residue position followed by examples of nucleic acid substitutions that attenuate hemolytic activity are: 181, C; 443, A; 583, A or G. The residue position followed by examples of nucleic acid substitutions not observed to attenuate hemolytic activity are: 50, G; 54, T; 98, C; 122, G; 134, C; 137, C; 187, T; 196, T; 248, C; 276, C; 302, C; 305, G; 351, T; 380, A; 382, C; 459, C; 514, G; 558, C; 566, G; 717, A; 764, G; 770, ; 1038, T; 1138, A; 1212, A; 1296, T; 1386, G; 1395, A.

FIGS. 3A and 3B Amino acid sequence of type 14 pneumolysin (SEQ ID NO: 3).

FIGS. 4A and 4B Non-limiting amino acid variations of type 14 pneumolysin (SEQ ID NO: 4). The residue position followed by examples of amino acid substitutions that attenuate hemolytic activity are: 61, Pro; 148, Lys; 195, Ile or Val; 243, Arg, Val, Glu, or Ser; 286, Asp; 446, Ser. The residue position followed by examples of amino acid substitutions not observed to attenuate hemolytic activity are: 17, Arg; 18, Asn; 33, Thr; 41, Gly; 45, Ala; 46, Thr; 63, Ser; 66, Tyr; 83, Ser; 101, Thr; 102, Gly; 127, Glu; 128, His; 153, Met; 172, Ala; 189, Arg; 239, Arg; 255, Gly; 257, Gly.

DETAILED DESCRIPTION OF THE INVENTION

Figure 5:
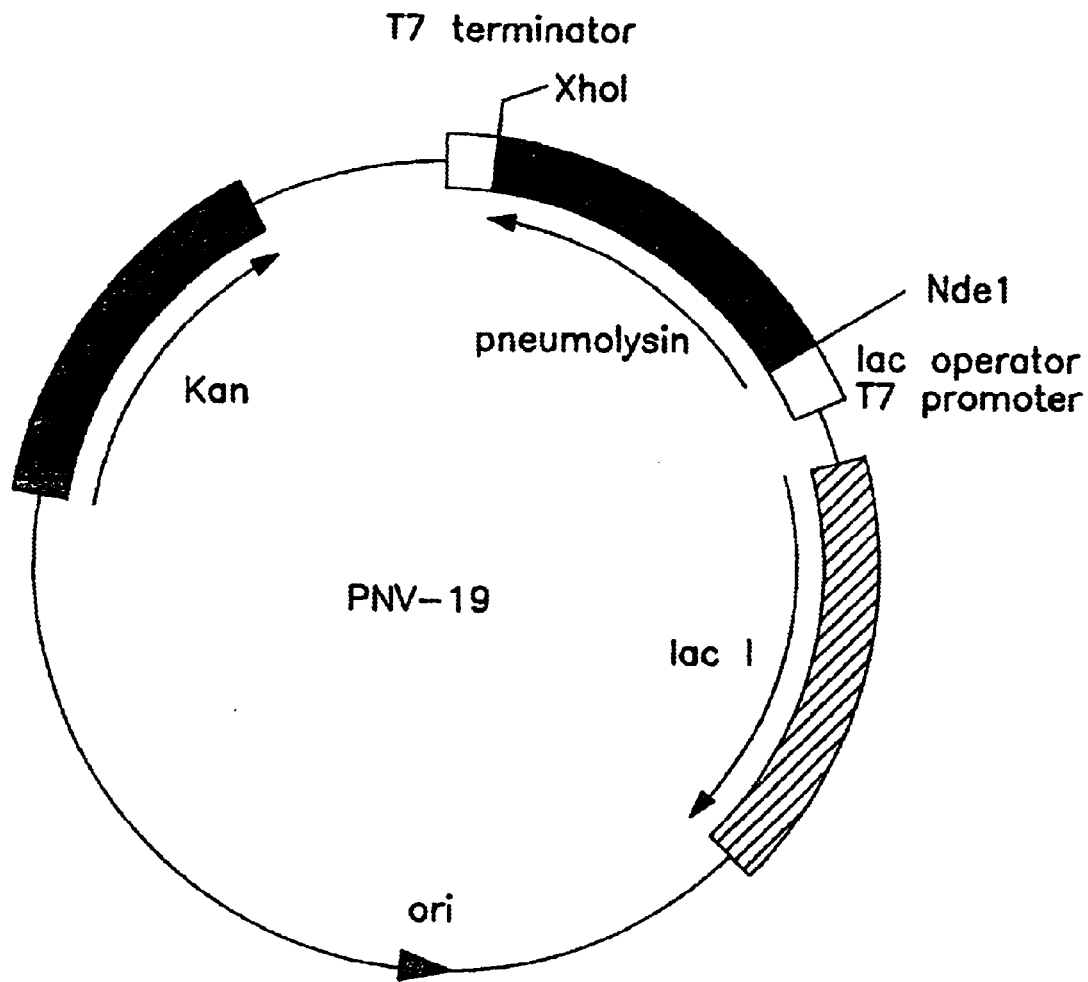
FIG. 5: Map of plasmid pNV-19 containing wild-type pneumolysin nucleic acid sequence. The pNV series of plasmids were derived from pET-24a by cloning in modified pneumolysin nucleic acid sequences.
Figure 6:
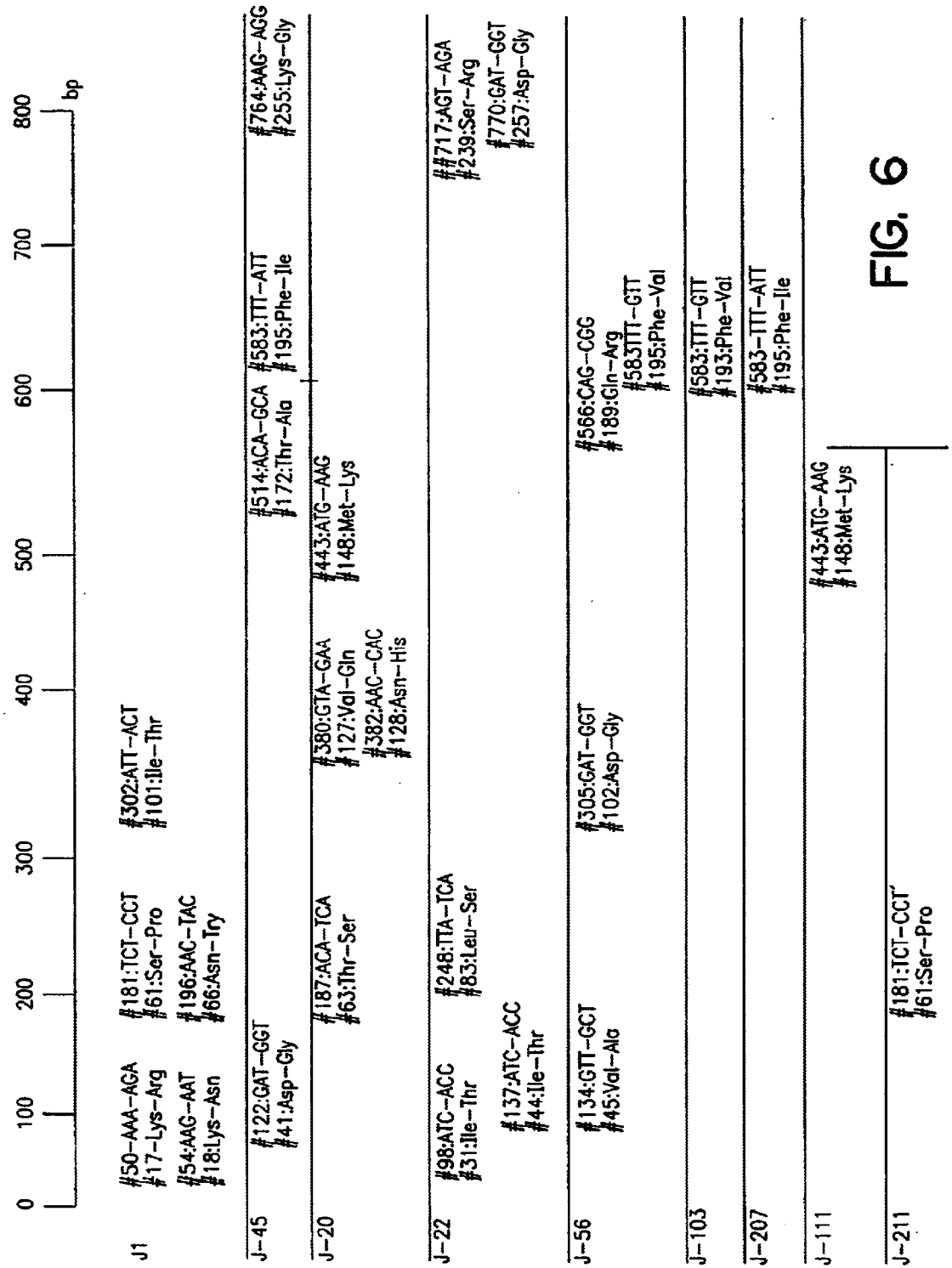
FIG. 6: Diagram showing the positions of the nucleic acid and amino acid substitutions in specific modified pneumolysin polypeptides pNVJ1, pNVJ45, pNVJ20, pNVJ22, pNVJ56, pNV103, pNV207, pNV111, pNV211.
Figure 7:
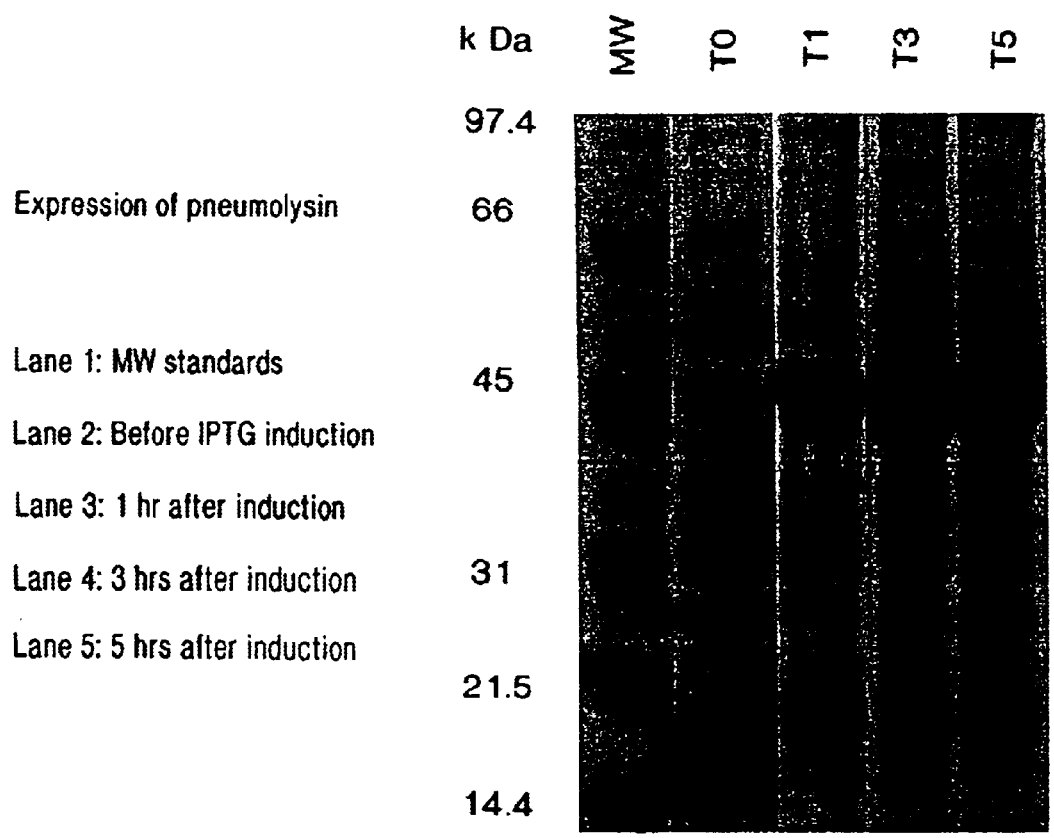
FIG. 7: SDS-PAGE showing expression of recombinant pneumolysin following IPTG induction.

Pneumolysin is found in virtually all known strains of *S. pneumoniae*. Its broad distribution provides the ability to obtain substantial cross-protection among different *S. pneumoniae* serotypes. This invention provides genetically modified pneumolysin polypeptides which act as toxoids (pneumolysoids) and are therefore useful for eliciting antibodies and for use in vaccines against *S. pneumoniae*. Nucleic acid sequences encoding the modified pneumolysins, vectors and host cells transformed with vectors comprising the nucleic acids encoding the modified pneumolysins are also embodiments of this invention.

The modified pneumolysin polypeptides of this invention in which at least one amino acid is substituted, retain sufficient epitopes to be immunogenic and elicit antibodies which are cross-reactive with wild-type pneumolysin. In addition, the toxicity of such modified polypeptides is sufficiently reduced to allow for their administration to mammals without substantial risk of dangerous side effect.

In an embodiment of this invention, specific modified pneumolysin polypeptides are provided which are covalently bound to polysaccharides to produce conjugates. By conjugating the modified pneumolysin polypeptides of this invention to different polysaccharides, this invention provides compositions capable of eliciting antibodies to a wide range of serologically distinct pathogens. By selecting the capsular polysaccharide from specific bacteria, this invention can be used to provide immunization against meningococcus, pneumococcus, haemophilus influenzae type b and Group B streptococcus as well as other bacteria.

In another embodiment of the invention, genetic modifications in the pneumolysin genome are generated using random mutagenesis techniques.

A. Method for Producing and Identifying Modified Pneumolysin

Genetically modified pneumolysin polypeptides of this invention are produced using conventional recombinant methodology (Sambrook et al. (1989) *Molecular Cloning: A Laboratory Manual* 2nd ed., Cold Spring Harbor Laboratory Press and Ausubel et al. Eds. (1997) *Current Protocols in Molecular Biology*, John Wiley & Sons, Inc.). Minor variant forms of pneumolysin polypeptides have been reported which show high degrees of conservation of amino acid and nucleic acid sequences. See, for example, Mitchell et al. (1990) *Nucleic Acid Res.* 18:4010 which is incorporated herein by reference and which reports that isoleucine at position 153 of pneumolysin of type 1 *S. pneumoniae* is substituted with methionine in type 2. Type 14 which also has isoleucine at position 153 has an asparagine at position 380 rather than an aspartic acid. These variations may also be included among other substitutions in the nucleic acid and amino acid compositions of this invention which provides modified pneumolysin in which at least one epitope is preserved.

Modified pneumolysin polypeptides are provided by this invention which have reduced or no hemolytic activity compared to the wild-type and retain a sufficient number of epitopes to produce antibodies cross reactive with native or wild-type pneumolysin. Identification of such polypeptides is accomplished by first inserting random mutations into the gene encoding pneumolysin and then screening the expressed polypeptide products for loss or reduction of activity associated with toxicity.

1. Methods of Modifying Pneumolysin

A novel screening system useful for making and identifying substantially immunogenic, but non-toxic or minimally toxic pneumolysins useful in immunizing against *S. pneumoniae* infections is provided by this invention.

This method comprises two basic steps: (1) random mutagenesis and (2) selection.

Random mutagenesis is one of the suitable techniques for introducing mutations into pneumolysin. Standard mutagenesis methods are suitable for use with this invention. In an embodiment, random PCR is performed in order to randomly incorporate nucleotide changes into the type 14 pneumolysin genome. The subsequent selection will identify desirable changes. This method is applicable with any isolated pneumolysin gene. Preferably, enough of the nucleic acid sequences is identified to enable production of oligonucleotide probes. Non-limiting examples of such pneumolysin genes are those encoding for type 2 and 14 pneumolysin. The nucleotide sequence encoding type 14 is shown in FIGS. 1A and 1B.

PCR, or nucleic acid amplification, is described in U.S. Pat. Nos. 4,183,195, 4,965,188 and 5,176,995, which are incorporated herein by reference. Generally, PCR is a method for amplifying one or more specific nucleic acid sequences wherein each sequence consists of two separate complementary strands. PCR requires hybridizing each strand with a complementary oligonucleotide primer. These nucleic acids are templates for synthesis of complementary strands using primers as described below. An extension product of each primer is then synthesized which is complementary to each nucleic acid strand. Next, the extension products are separated from the templates on which they were synthesized to produce single stranded molecules. Finally, the single stranded molecules are again treated with the primers of the first step under conditions such that an extension product is synthesized for each of the single stranded molecules produced in the second step. These steps may be repeated for optimal amplification of the original nucleic acid and product synthesis.

PCR mutagenesis involves incorporation of a "mismatch" nucleotide into the growing strand and may be facilitated by reliance on the high error rate of commonly used PCR polymerases. Other methods, known in the art for creating random mutations may also be used such as, for example chemical mutagenesis (Eichenleub, R. (1979) *J. Bacteriol.* 138:559–566.) Alternatively, the mutagenesis step may be accomplished by PCR using a "semi-random" process in which either one or both primers include a random series of nucleotides but a portion of one or both primers is complementary and thus "anchored" to at least one known pneumolysin sequences.

"Primers," as that term is used herein, refers to an oligonucleotide, whether occurring naturally as in a purified restriction digest or produced synthetically, which is capable of acting as a point of initiation of nucleic acid synthesis when placed under conditions in which synthesis of a primer extension product which is complementary to a nucleic acid strand is induced, i.e. in the presence of nucleotides and an inducing agent such as DNA polymerase and at a suitable temperature and pH. The primers are preferably single stranded for maximum efficiency in amplification, but may alternatively be double stranded. If double stranded, the primer is first treated to separate its strands before being used to prepare amplification products. Preferably, the primers are oligodeoxyribonucleotides but must be sufficiently long to prime the synthesis of extension products in the presence of the inducing agent. The exact lengths of the primers will depend on many factors, including temperature, source of primer and use of the method. The primers typically contain 10 or more nucleotides.

Synthetic oligonucleotide primers may be prepared using any suitable method, such as, for example, the phosphotriester and phosphodiester methods (Narang, S. A. et al. (1979) *Meth. Enzymol.* 68:90; Brown E. L., et al. (1979) *Meth. Enzymol.* 68:109) or automated embodiments thereof. In one such automated embodiment, diethylphosphoramidites are used as starting materials and may be synthesized as described by Beaucauge et al. (1981) *Tetrahedron Let.* 22:1859–1962. One method for synthesizing oligonucleotides on a modified solid support is described in U.S. Pat. No. 4,458,066 which is incorporated herein by reference.

It is also possible to use a primer which has been isolated from a biological source. One such example may be a restriction endonuclease digest of a large nucleic acid molecule encoding pneumolysin which is sufficiently complementary to hybridize to the pneumolysin sequences. Nucleotide substitutions may also be inserted into primers during chemical synthesis.

It is to be understood that the nucleotide sequences of this invention need not be limited to a single mutation within any given molecule encoding the modified pneumolysin polypeptides. Multiple mutations are also possible when they preserve the immunogenic character of native pneumolysin polypeptide (see FIGS. 2A and 2B), while attenuating or eliminating one or more of its toxic characteristics. Multiple modifications may therefore be included in a single polypeptide molecule (see FIGS. 4A and 4B). Multiple modifications may be useful because they may reduce the likelihood of reversion to the toxic native sequence. However, a preferred embodiment of this invention is single mutations in the nucleic acid sequence which result in single amino acid substitutions.

The random or semi-random PCR products encoding modified pneumolysin, may be cloned into an appropriate expression vector using standard cloning techniques known in the art.

In an embodiment, the vector includes at least one possible cloning site, at least one antibiotic selection marker gene, transcription promoter and an origin of replication. The vector may be grown in a variety of compatible host cells, allowing a high degree of expression. Preferred hosts include bacteria such as *E. coli, B. subtilis* or yeast such as *S. cerevisiae*. Other eukaryotic cells besides yeast such as mammalian cells may also be used, for example. The cloning plasmid vector/host cell combination may be any compatible vector and host cell. Any suitable expression vector and host cell are acceptable provided they are able to support the expression of the modified pneumolysin. Standard protocols for cloning and expression may be used as described in Ausubel, F. M. et al., eds. (1997) *Current Protocols in Molecular Biology*, John Wiley & Sons, Inc. which is incorporated herein by reference.

2. Screening of Modified Pneumolysin

Following ligation of the modified pneumolysin nucleotide sequence to the vector in proper reading frame and transformation into the host cell, screening is performed in order to identify cell clones expressing modified pneumolysin polypeptides which have reduced or absent toxicity.

A method for identifying suitably transformed hosts expressing the randomly mutated pneumolysin polypeptide is provided by this invention. Preferred modified pneumolysin polypeptides will have similar structural features such as size when compared to native pneumolysin. Therefore selection methods which analyze polypeptide size such as SDS-PAGE and gel permeation chromatography maybe used. Transformed hosts expressing modified pneumolysin maybe identified by analyzing the proteins expressed by the host using SDS-PAGE and comparing the gel to an SDS-PAGE gel obtained from the host which was transformed with the same vector but not containing a nucleic acid sequence coding for pneumolysin or modified pneumolysin (the "standard host").

Transformed hosts expressing pneumolysoid will produce a new band when examined by SDS-PAGE and transformed hosts producing a large band corresponding to pneumolysoid can be selected as candidates. The modified pneumolysin polypeptides expressed by these clones may then be screened for hemolytic activity in the cell extracts to identify the modified pneumolysin polypeptides that have attenuated hemolytic activity. Transformed hosts producing non-modified or modified yet active pneumolysin which are toxic can be eliminated by this simple screening step.

Alternatively, modified pneumolysin can be identified by other methods known to those of ordinary skill in the art such as, but not limited to, SDS-PAGE, followed by electroblotting or western blotting analysis, or dot blotting of total cell extracts, or limited proteolysis of the soluble fraction and further analysis of the digests by SDS-PAGE or western blotting.

Factors to be considered in choosing the method of pneumolysin purification and isolation include whether the modified pneumolysin is present as a soluble protein or whether it becomes insolubilized in inclusion bodies. Although not a general rule, mutations which affect the folding properties of pneumolysin appear to favor its accumulation in inclusion bodies.

Modified pneumolysin which has been identified in the soluble fraction of the cell extracts may be isolated and purified by conventional methods of purification, such as, but not limited to: precipitation of nucleic acids, salt fractionation or capture procedures such as ion exchange chromatography or hydrophobic interaction chromatography. Gel permeation chromatography may be used, particularly as a polishing step, following one of the aforementioned chromatographic procedures. Alternatively, the recombinant modified pneumolysin may be isolated by affinity chromatography, or by procedures used for isolation of thiol-containing proteins, as well as other methods known to those of ordinary skill in the art (Current Protocols in Protein Science, 1995 John Wiley & Sons).

Alternatively, modified pneumolysin derived from the inclusion bodies may be isolated following several inclusion body washes to remove nucleic acids and other bacterial cell wall contaminants. This procedure may include, but is not limited to, washing the pellet with regular buffers, or regular buffers and detergent additives. The protein may be further purified under denaturing conditions by dissolving the washed inclusion bodies in urea or guanidine HCl followed by gel filtration chromatography. This procedure can be done prior to protein refolding. However, refolding followed by ion-exchange chromatography represents a preferred method to achieve maximal yields of refolded and purified protein.

Native pneumolysin can be obtained by the procedure described and used as reference. The hemolytic activity and the migratory or elution profile of the native counterpart can thus be used as reference for the isolation of modified pneumolysins from either the soluble or inclusion body fractions.

Preferred criteria for selecting clones expressing suitable modified pneumolysin polypeptides include one or more of: (1) modified pneumolysin expression; (2) at or near full length expression (based on a molecular weight of about 53,000 for native pneumolysin); (3) presence of pneumolysoid in the soluble fraction; (4) low hemolytic activity; and (5) high yield of expressed polypeptide.

Although the inclusion of all the above criteria in a screening protocol would identify the most efficient and likely useful clones expressing a useful modified pneumolysin polypeptide, less efficient clones may also produce modified pneumolysins which are suitable for use in this invention including some that may not be full length, but are sufficiently long to elicit production of antibodies cross-reactive with native pneumolysin and/or function as carrier polypeptides in a polysaccharide-polypeptide conjugate molecule.

Although the preferred method for identifying desirable clones described above directly assays characteristics of expressed protein including size and hemolytic activity, other methods such as detecting cross-reactivity with antibodies directed against native pneumolysin or hybridization to nucleic acid probes may also be used. In one embodiment, initial identification of host cell clones transformed with plasmids containing the modified pneumolysin nucleic acid sequences may be performed using standard hybridization analysis as known to those skilled in the art. Probes for modified pneumolysin genes include native pneumolysin nucleic acid sequences or the amplification primers or other primers indicating the presence of the amplified sequences. Preferably such hybridizing probes are 30 to 40 nucleotides in length; more preferable 10 to 20 nucleotides in length. Stringency should be relatively low since probes may be hybridizing to sequences containing altered bases.

A preferred method of hybridization is blot hybridization. See Sambrook et al. (1989) *Molecular Cloning: A Laboratory Manual* 2nd Ed., Cold Spring Harbor Laboratory Press which is incorporated herein by reference, for additional details regarding blot hybridization. A probe can be DNA or RNA and can be made detectable by any of the many labeling techniques readily available and known to the skilled artisan. Such methods include, but are not limited to, radio-labeling, digoxygenin-labeling, and biotin-labeling. A well-known method of labeling DNA is $^{32}$P using DNA polymerase, Klenow enzyme or polynucleotide kinase. In addition, there are known non-radioactive techniques for signal amplification including methods for attaching chemical moieties to pyrimidine and purine rings (Dale, R. N. K. et al. (1973) *Proc. Natl. Acad. Sci. USA* 70:2238–42), methods which allow detection by chemiluminescence (Barton, S. K. et al. (1992) *J. Am. Chem. Soc.* 114:8736–40) and methods utilizing biotinylated nucleic acid probes (Johnson, T. K. et al. (1983) *Anal. Biochem.* 133:125–131; Erickson, P. F. et al. (1982) *J. Immunol. Methods* 51:241–49; Matthaei, F. S. et al. (1986) *Anal. Biochem.* 157:123–28) and methods which allow detection by fluorescence using commercially available products. Non-radioactive labeling kits are also commercially available.

The screening process includes testing of the pneumolysoid-expressing cells for low hemolytic activity by methods which are known in the art. (Bernheimer, A. (1988) *Meth. Enzymol.* 165:213–217.) A micro-assay may be performed in a 96-well, U-bottom, micro-titer plate, using an aliquot of culture grown from colonies positive for pneumolysin (native or modified) expression determined as described above. The aliquots may be extracted and normalized for polypeptide content. The extracts may further be centrifuged and the resulting pellet cell debris and the supernatant analyzed separately. Further identification of pneumolysoid expression in the supernatant indicates availability in the solubilized fraction.

Aliquots of the cell lysates may be obtained, pelleted by centrifugation and the supernatant or pellet analyzed for activity. Screening the pellets for activity involves solubilization with a denaturant, such as urea, followed by serial dilutions which are conducted as described for the soluble species. Using this procedure the protein undergoes refolding and activity, if present, can be detected.

Negative activity results imply either an inactive refolded polypeptide or an improperly refolded polypeptide. To distinguish between these two conditions, a second screening process can be used. Activity-negative clones are denatured and refolded before loading onto an ion-exchange chromatography column. The mutants which have an elution pattern similar to wild-type pneumolysin can be further analyzed by gel-filtration chromatography and monomeric species with a Stokes radius similar to wild-type pneumolysin are selected.

The inserted nucleic acid sequence encoding the modified pneumolysin of selected clone(s) may be sequenced by any of the methods commonly used in the art and the corresponding amino acid sequences deduced.

B. Modified Pneumolysin Polypeptides

1. Reduction of Hemolytic Activity

The modified pneumolysin polypeptides of this invention are polypeptides that are non-hemolytic or substantially non-hemolytic and still maintain at least one epitope that binds to antibody directed against the native polypeptide. Because such hemolytic activity is associated with the toxicity of pneumolysin, the modified pneumolysins would therefore also be expected to be less toxic than native pneumolysin. The modified pneumolysin polypeptides of this invention contain at least one mutation relative to *S. pneumoniae* type 14 wild-type pneumolysin (FIGS. 3A and 3B), preferably among the first 257 amino acids beginning from the N-terminus. Modification of as few as one amino acid is required to result in modified pneumolysin polypeptides which have little or insignificant toxicity as determined by hemolytic assay. Thus, substitutions at any one, or more, of positions 61, 148 and 195 may result in polypeptides having reduced hemolytic activity. Preferred substitutions for amino acids 61, 148 and 195 are shown below in Table 1.

TABLE 1

| | Amino Acid Position | | |
|---|---|---|---|
| | 61 | 148 | 195 |
| Wild-type | Ser | Met | Phe |
| Substitutions | Pro | Lys | Ile/Val |

Substitutions at these preferred positions with amino acids other than the preferred ones, for example, those having similar charge at neutral pH, are also within the scope of this invention. Accordingly, substitution of the serine at 61 with hydroxyproline; methionine at 148 with arginine or histidine; phenylalanine at 195 with leucine, glycine or alanine are other non-limiting examples of possible substitutions.

Although single substitutions may be sufficient to attenuate hemolytic activity, such reduction may also be accomplished by substituting in a single polypeptide specific groups of amino acids. For example, the collective substitution in a single polypeptide of the amino acids at positions 33, 46, 83, 239 and 257 produces polypeptides having characteristics of pneumolysin but with reduced hemolytic activity. Preferred substitutions are shown in Table 2.

TABLE 2

| | Amino Acid Position | | | | |
|---|---|---|---|---|---|
| | 33 | 46 | 83 | 239 | 237 |
| Wild-type | Ile | Ile | Leu | Ser | Asp |
| Substitution | Thr | Thr | Ser | Arg | Gly |

As with the single substitution, other amino acids in addition to those which are preferred may also be substituted based on the same considerations of charge discussed above with the further non-limiting example that serine and threonine may be substituted for each other, and that other neutral amino acids such as those recited above may be substituted for Asp at 257.

It should be understood that besides the substitutions disclosed above, which are effective for reducing or eliminating the hemolytic activity, other substitutions may also be made provided that at least one epitope capable of binding an antibody which binds native pneumolysin is retained. Non-limiting examples of amino acid residues which may be substituted but which alone do not reduce hemolytic activity include those at positions 17, 18, 33, 41, 45, 46, 63, 66, 83, 101, 102, 127, 128, 172, 189, 239, 255 and 257. Examples of substitutions at these positions include, but are not limited to those shown in Table 3. Because these sites are not associated with decreases in hemolytic activity it is expected that these positions may be more freely substituted with less regard to size and charge.

TABLE 3

| | Amino Acid Position | | | | | | | | |
|---|---|---|---|---|---|---|---|---|---|
| | 17 | 18 | 33 | 41 | 45 | 46 | 63 | 66 | 83 |
| Wild-type | Lys | Lys | Ile | Asp | Val | Ile | Thr | Asn | Leu |
| Substitution | Arg | Asn | Thr | Gly | Ala | Thr | Ser | Tyr | Ser |

TABLE 3-continued

| | Amino Acid Position | | | | | | | | |
|---|---|---|---|---|---|---|---|---|---|
| | 101 | 102 | 127 | 128 | 172 | 189 | 239 | 255 | 257 |
| Wild-type | Ile | Asp | Val | Asn | Thr | Gln | Ser | Lys | Asp |
| Substitution | Thr | Gly | Glu | His | Ala | Arg | Arg | Gly | Gly |

It is to be understood that the amino acid substitutions described above are not exhaustive and that other modified pneumolysin polypeptides identified according to the methods of this invention are also within its scope.

Single point mutations of the native pneumolysin sequence are preferred because the antigenic nature of the native pneumolysin polypeptide is more likely to be preserved by the single point modified form. Alternatively, a combination of multiple mutations, may be used.

However, multiple mutations are sometimes unpredictable. The mutations, in some cases, may act synergistically to abolish activity or they may be involved in compensation mechanisms during folding. For these reasons, single point mutations are considered to be advantageous.

Although the screening process is based on identifying modified pneumolysin polypeptides which are substantially full-length, this invention also encompasses fragments and truncated forms of the modified pneumolysin polypeptides provided they retain at least one epitope recognized by an antibody which binds to the mature pneumolysin. In addition, it is preferred that such fragments or truncated forms be of sufficient size to produce polysaccharide-polypeptide conjugates which produce a T cell dependent immune response.

The hemolytic activity of the pneumolysoid proteins of this invention may vary over a wide range depending on how the pneumolysoid is actually used. For example, conjugation of a pneumolysoid with reduced hemolytic activity may reduce such activity further to acceptable levels. Conversely, where a pneumolysoid is to be introduced into an individual, unconjugated to another component or where it may be cleaved, it will be desirable to have the hemolytic activity reduced as close to the minimum detectable level as possible. For such purposes, levels of hemolytic activity between about 0.2% and about 0.5%, or more preferably about 0.2% are suitable. Where some hemolytic activity may be tolerated, or where such activity may be further attenuated by, for example, conjugation to polysaccharide, higher levels of hemolytic activity may be acceptable, i.e. from about 0.5% to about 25%, or more preferably between about 1% and about 10%.

2. Protein Structure

Previous studies report that the C-terminus of PLY contains the cell-binding site (Owen et al., 1994 FEMS Microbiol. Let. 121, 217–221). The mutagenesis studies of this invention were focused on the N-terminus which reportedly contains the oligomerization domain. The finding that pre-incubation of erythrocytes with certain mutants abrogated the wild type hemolytic activity in a concentration dependent manner indicates that these mutants are indeed capable of competing with the wild type counterpart for the cell binding site. Since the mutants inhibit wild type activity, these mutants likely retain the structural features of wild-type pneumolysin. The preservation of the cell binding domain in the mutant forms, specifically in the case of pNV103 and pNV207 is significant as these mutants also exhibit the immunological properties of the wild type molecule, as evidenced in ELISA inhibition assays. Moreover, antibodies generated against these mutants possess the ability to neutralize the hemolytic activity of the wild type counterpart, additional evidence of their native-like structure.

The structural features and integrity of wild type pneumolysin and selected mutants have also been assessed by circular dichroism and fluorescence spectroscopy. These techniques offer the unique advantage of providing both qualitative and quantitative information on the secondary and tertiary structure of these proteins. Wild type pneumolysin is characterized by a high content of β-sheet structure, a prominent feature in the far UV CD spectra of all the mutants selected in the present study. The shape of the spectra and deconvolution analysis are consistent with previous studies on recombinant pneumolysin purified from soluble fractions of E. coli which was structurally and functionally equivalent to the native pneumococcal pneumolysin (Mitchell et al., 1989 Biochem. Biophys. Acta 1007, 67–72). Likewise, both the near UV CD and fluorescence spectra are consistent with the native structure containing Trp residues (Morgan et al., 1993 Biochem. J. 296, 671–674) whose side chains are partially exposed to solvent, as evidenced by the emission maximum at ~345 nm upon excitation at 290 nm. The unique near UV CD spectra characterized by a minimum ellipticity at ~280 and a maximum ellipticity at ~290 nm, represents a fingerprint of this (Morgan et al., 1993) and other cytolysins, such as perfringolysin (Nakamura et al., 1995 Biochemistry 34, 6513–6520). As such, this characteristic spectroscopic fingerprint may represent a useful baseline measurement for subsequent evaluation of batch-to-batch consistency, particularly for those mutants selected as components of vaccine candidates.

C. Nucleic Acid Molecules Encoding Modified Pneumolysin

The modified pneumolysin polypeptides of this invention are preferably synthesized by expressing a nucleic acid molecule encoding the modified polypeptide in a host microorganism transformed with the nucleic acid molecule. Accordingly, this invention also encompasses the nucleic acid molecules, including DNA and RNA encoding the modified pneumolysins discussed above.

The DNA encoding the polypeptides of the invention may be used to express recombinant polypeptide in a wide variety of host cells using a wide variety of vectors. The host cell may be prokaryotic or eukaryotic. DNA for native wild-type pneumolysin may be obtained from natural sources, such as *Streptococcus pneumoniae,* or alternatively synthesized. The wild-type DNA may then be used as the starting material for modification, as described above, to obtain the DNA encoding the modified pneumolysin polypeptides of this invention. Once identified as encoding desirable modified pneumolysin polypeptides, the DNA encoding such polypeptides may then be cloned into various vectors for expression. Alternatively, the genes encoding such polypeptides may also be synthesized in whole or in part.

In one embodiment, the invention relates to a method of expressing the modified pneumolysin polypeptide in a microorganism wherein the microorganism is transformed by a vector comprising a gene encoding the modified pneumolysin polypeptide wherein the polypeptide so produced comprises more than about 2% of the total protein expressed in the transformed microorganism. In yet another embodiment, the modified pneumolysin polypeptide expressed comprises more than about 40% of the total proteins expressed in *E. coli.*

Cloning vectors may comprise segments of chromosomal, non-chromosomal and synthetic DNA sequences. Non-limiting examples of some suitable prokaryotic vectors include plasmids from *E. coli,* such as colEl, pCR1, pBR322, pMB9, and RP4. Prokaryotic vectors also include derivatives of phage DNA such as M13, fd, and other filamentous single-stranded DNA phages.

The modified pneumolysin polypeptides can be expressed either direct or as fusion constructs. Two non-limiting examples of fusion constructs are Thiofusion and His-Tag which can be isolated and purified by conventional methods. Vectors for expressing proteins in bacteria, especially *E. coli,* are also known. Such vectors include, but are not limited to, pK233 (or any of the tac family of plasmids), pT7, and lambda pSKF. Examples of vectors that express fusion proteins include the PATH vectors described by Dieckmann and Tzagoloff (1985) in *J. Biol. Chem.* 260:1513–1520. These vectors contain DNA sequences that encode anthranilate synthesis (TrpE) followed by a polylinker at the carboxy terminus. Two non-limiting examples of fusion constructs are Thiofusion and His-Tag which can be isolated and purified by conventional methods. Other expression vector systems are based on beta-galactosidase (pEX); maltose binding protein (pMAL); and glutathione S-transferase (pGST)—(see (1988) *Gene* 67:31 and (1990) *Peptide Research* 3:167). See Ausubel et al., supra.

Vectors useful in yeast are also available. Suitable examples are YIp, YRp, YCP, YEp and YLp plasmids. See Ausubel, Id.

Suitable vectors for use in mammalian cells are also known. Such vectors include well-known derivatives of SV-40, adenovirus, retrovirus-derived DNA sequences and vectors derived from combination of plasmids and phage DNA. Additional vectors for eukaryotic expression vectors are reported in (e.g., P. J. Southern and P. Berg (1982) *J. Mol. Appln. Genet.* 1:327–341; S. Subramani et al. (1981) *Mol. Cell. Biol.* 1:854–864; R. J. Kaufmann and P. A. Sharp (1982) *J. Mol. Biol.* 159:601–621; R. J. Kaufmann and P. A. Sharp (1982) *Mol. Cell. Biol.* 159:601–664; S. I. Scahill et al. (1983) *Proc. Natl. Acad. Sci.* USA 80:4654–4659; G. Urlaub and L. A. Chasin (1980) *Proc. Natl. Acad. Sci.* USA 77:4216–4220.

Examples of preferred vectors are plasmids, and some non-limiting examples of plasmids containing the T7 inducible promotor, include the expression plasmids pET-17b, pET-11a, pET-24a-d(+) and pET-9a, all of which are commercially available from Novagen (565 Science Drive, Madison, Wis. 53711). These plasmids comprise, operatively linked, in sequence, a T7 promoter, optionally a lac operator, a ribosome binding site, restriction sites to allow insertion of the structural gene and a T7 terminator sequence. See, Novagen catalogue (1993) at 36–43.

Useful expression hosts include well-known prokaryotic and eukaryotic cells. Some suitable prokaryotic hosts include, for example, *E. coli,* such as *E. coli* BL21 (DE 3), *E. coli* SG-936, *E. coli* HB 101, *E. coli* W3110, *E. coli* X1776, *E. coli* X2282, *E. coli* DHI, and *E. coli* MRC1, Pseudomonas, and Bacillus, such as *Bacillus subtilis,* and Streptomyces. Suitable eukaryotic cells include yeasts such as Saccharomyces and other fungi, insect, animal cells, such as COS and CHO cells, human cells and plant cells in tissue culture.

In a preferred embodiment, *E. coli* strain BL21 (DE3) is employed. The above mentioned plasmids may be transformed into this strain.

Selection of *E. coli* transformed with the desired vectors may be accomplished using standard selection protocols involving growth in a selection medium which is toxic to non-transformed cells. For example, E. coli is grown in a medium containing a selection agent, e.g. any β-lactam to which E. coli is sensitive such as ampicillin. The pET expression vectors provide selectable markers which confer antibiotic resistance to the transformed organism.

High level expression of the modified pneumolysin polypeptide can be toxic in *E. coli*. Surprisingly, this invention allows for selection of modified pneumolysin polypeptides which may be expressed in *E. coli* to a level of at least about 40% of total cellular proteins.

Additional nucleotide mutations may be made that were not identified in the selection process particularly where the translated amino acid is the same as the identified amino acid predicted based on the sequence of the selected clone. In addition, nucleotide changes may be made which encode conservative amino acid substitutions, especially where the identified polypeptides exhibit other amino acid substitutions. Conservative amino acid substitutions are known in the art and represent substitutions of "similar" amino acids. Considerations include, but are not limited to polarity, hydrophobicity, size, and side chain structure.

The modified pneumolysin polypeptides of this invention are polypeptides that are non-toxic or substantially non-toxic and still retain at least one epitope that binds antibody directed at native pneumolysin. The modified pneumolysin of this invention contain at least one mutation relative to wild-type pneumolysin, preferably among the first 257 amino acids of the N-terminus. The modified pneumolysin may be altered in that the amino acid present at one, or more than one, of residue sites 17, 18, 33, 41, 45, 46, 61, 63, 66, 83, 101, 102, 127, 128, 148, 172, 189, 195, 239, 243, 255, 257, 286 or 446 of wild-type pneumolysin are replaced, removed or blocked. As discussed above, additional modifications can be incorporated from other known, modified pneumolysin polypeptides such as those at residue sites 367, 379, 384, 385, 397, 428, 433, 434 or 435 which are disclosed in PCT WO 90/06951 which is incorporated herein by reference. In addition to the amino acid substitutions of this invention disclosed herein, other amino acid substitutions that have been reported (Hill et al. (1994) *Infection and immunity* 62, 757–758) for pneumolysin may also be used with this invention provided they allow for refolding of the pneumolysin as determined by the methods described herein. Hill et al. reports four N-terminal region mutations, Arg-31→Cys, Leu-75→Phe, Val-127→Gly and His-156→Tyr that result in 75%, 100%, 75% and 2% hemolytic activity, respectively. They also report four C-terminal region mutations, Ala-432→Val, Trp-433→Arg, Trp-436→Arg and Val-468→Leu that result in 100%, <1%, 50% and 100% hemolytic activity, respectively. However, if any of these mutations result in improperly refolded pneumolysoids, then it is preferred they not be used. The preferred modifications of pneumolysin are those at residue sites 61, 148 or 195 and the most preferred is at residue 195. Additionally, the combination of modifications at sites 33, 46, 83, 239 and 257 is also preferred.

Specific changes may be introduced into the native pneumolysin sequence by any of the methods for site-directed mutagenesis known in the art. In a preferred embodiment, PCR may be performed using oligonucleotide amplification primers encoding the desired nucleotide substitution(s) within their sequence.

Alternatively, the modified pneumolysoid polypeptide may be constructed by chemical synthesis. (Kent et al. Adv. Exp. Med. Biol., 1995, 362, 425–438). Such synthesis can be used to make all or part of a pneumolysoid. In the case of partial synthesis, the synthetic peptide can be covalently bound to an appropriate portion of the pneumolysoid peptide, prepared by methods known in the art or taught herein, to generate a semi-synthetic pneumolysoid.

D. Vaccine and Antibody Preparations

This invention is also directed to vaccine and antibody preparations. According to this invention, the expressed, modified pneumolysin described above or its derivatives or fragments thereof may be used as an immunogen to generate antibodies that are reactive against pneumolysin.

1. Antibodies

The recombinant techniques for polypeptide expression described above, provide for the production of abundant amounts of the modified pneumolysin polypeptides of this invention, based on the nucleic acid sequences of this invention. This facilitates the generation of antibodies reactive against the modified pneumolysin polypeptide. However, it should be understood that the polypeptide may also be synthesized by chemical methods or combinations thereof.

In another embodiment, antibodies directed against the modified pneumolysin polypeptides may be generated by any of the techniques that are well known in the art. According to one approach, the antibodies may be generated by injecting an isolated modified pneumolysin polypeptide preparation or derivatives or fragments thereof into a host animal. The host animal may be, but is not limited to, rat, mouse, rabbit, non-human primate, or a human. Immunological responses may be increased by the use of adjuvants which are known in the art.

Monoclonal antibodies directed against the modified pneumolysin polypeptide may also be prepared by any of the techniques that are well known in the art. According to one method, cultures of continuous hybridoma cell lines are used (Kohler and Milstein (1975) *Nature* 256:495–497). Monoclonal antibodies directed against the modified pneumolysin polypeptide may be human monoclonal antibodies or chimeric monoclonal antibodies made by any of the techniques that are well known in the art. According to one approach, chimeric monoclonal antibodies may be generated that have a non-human (e.g. mouse) antigen-binding domain combined with a human constant region. (Takeda et al. (1985) *Nature* 314:452).

Antibodies directed against the modified pneumolysin polypeptide may be purified by any of the techniques that are well known in the art including, but not limited to immunoabsorption or immunoaffinity chromatography, or other chromatographic methods (e.g. HPLC, gel filtration or ion exchange). Antibodies may also be purified as immunoglobulin fractions from serum, plasma or cell culture medium.

Antibody molecules of this invention may be intact immunoglobulin molecules, substantially intact immunoglobulin molecules, or those portions of an immunoglobulin molecule, for example Fab fragments, that contain the antigen binding site.

Fragments of antibodies directed against the modified pneumolysin polypeptide may be generated by any of the techniques that are well known in the art. (Campbell (1985) *Laboratory Techniques in Biochemistry and Molecular Biology,* Vol. 13, Burdon, et al. (eds.), Elsevier Science Publishers, Amsterdam).

2. Conjugate Molecules

The modified pneumolysin polypeptides of this invention may be used to elicit an antibody response to *S. pneumoniae* in an individual either alone or when conjugated to another immunogenic molecule such as a polysaccharide. The other immunogenic molecule, may be derived from either *S.* pneumoniae, or from a different infectious agent against which it is desirable to generate an immune response. Preferably the other immunogenic molecule to which the modified pneumolysin is conjugated is a capsular or non-capsular polysaccharide from a pathogenic bacteria. Such bacteria including for example: Haemophilus influenzae type b; meningococcus group A, B, or C; group B or A streptococcus of various serotypes including group B types Ia, Ib, II, III, V, and VIII; as well as the various serotypes of *S. pneumoniae* preferably types 1–23. *S. pneumoniae* serotypes 3, 4, 6b, 9v, 14, 18c, 19f and 23 are most preferred. Such polysaccharides for use to conjugate pneumolysoid may also be modified themselves in order to be more effective or reduce cross-reactivity to endogenous epitopes. See, for example, Jennings et al. U.S. Pat. Nos. 4,727,136, 5,576,002 and U.S. application Ser. No. 08/484,569 which is published as international application WO 96/40239 which are incorporated herein by reference for modification to group B meningococcal polysaccharides.

Any mode of conjugation may be employed to conjugate the polysaccharide components with the modified pneumolysin polypeptide. A preferred method is that described in U.S. Pat. No. 4,356,170, i.e. by introducing terminal aldehyde groups (via oxidation of cis-vicinal hydroxyl groups) into the polysaccharide and coupling the aldehyde groups to the polypeptide amino groups by reductive amination. The polysaccharide and the modified pneumolysin polypeptides are thereby linked through a $—CH_2—NH$-polypeptide linkage.

It is to be understood, however, that the conjugate vaccines of the invention are not limited to those produced via reductive amination. Thus, the vaccines may also be produced by conjugating the polysaccharide with the modified pneumolysin polypeptide using an adipic dihydrazide spacer, as described by Schneerson, R., et al. (1980) *J. Exp. Med.* 1952:361–476, and in U.S. Pat. No. 4,644,059. Alternatively, the binary spacer technology developed by Merck may be used, as described by Marburg, S. et al. (1986) *J. Am. Chem. Soc.* 108:5282–5287 or, possibly, the reducing ends methodology.

Conjugate molecules prepared according to this invention typically comprise at least one modified pneumolysin polypeptide of the present invention to which is bound at least one polysaccharide component. Thus, this invention provides the ability to produce conjugate molecules wherein the polypeptide is linked to the polysaccharide through at least two sites to create cross-linked conjugates.

The vaccines of this invention may provide active or passive immunity. Vaccines for providing active immunity comprise a purified modified pneumolysin polypeptide of this invention. Preferably the polypeptide of this vaccine comprises at least one of the following amino acid substitutions in the wild-type pneumolysin amino acid sequence as shown in Table 1.

In another embodiment of this invention, antibodies directed against the modified pneumolysin polypeptide of this invention may be used as a pharmaceutical preparation in a therapeutic or prophylactic application in order to confer immunity from a host individual to another individual (i.e. to augment an individual's immune response against *S. pneumoniae* or to provide a response in immuno-compromised or immuno-depleted individuals including AIDS patients). Passive transfer of antibodies is known in the art and may be accomplished by any of the known methods. According to one method, antibodies directed against the modified pneumolysin polypeptides or conjugates thereof of this invention are generated in an immunocompetent host ("donor") animal, harvested from the host animal and transfused into a recipient individual. For example, a human donor may be used to generate antibodies reactive against the modified pneumolysin polypeptide or conjugate of this invention, the antibodies transfused in therapeutically or prophylactically effective amounts into a human recipient in need of treatment, thereby conferring resistance in the recipient against not only the pneumolysin toxin, but against *S. pneumoniae* and a bacteria which bind antibodies elicited by the polysaccharide component if the donor was immunized with a conjugate.

E. Pharmaceutical Compositions

The pharmaceutical compositions of this invention may comprise the modified pneumolysin polypeptides, conjugate molecules comprising the modified polypeptides or compositions comprising antibodies elicited by one of the modified pneumolysin polypeptide compositions of this invention. These pharmaceutical compositions are particularly useful as vaccines.

For eliciting passive immunity, the pharmaceutical composition may be comprised of, polyclonal antibodies or monoclonal antibodies or their derivatives or fragments thereof as described above. The amount of antibody, fragment, or derivative will be a therapeutically or prophylactically effective amount as determined by standard clinical techniques.

The pharmaceutical preparations of this invention may be introduced to an individual by methods known to be effective in the art. Intradermal, intraperitoneal, intravenous, subcutaneous, intramuscular, oral, and intranasal are among, but not the only routes of introduction.

The compositions of the invention may comprise standard carriers, buffers or preservatives known to those in the art which are suitable for vaccines including, but not limited to any suitable pharmaceutically acceptable carrier, such as physiological saline or other injectable liquids. Additives customary in vaccines may also be present, for example stabilizers such as lactose or sorbitol, and adjuvants to enhance the immunogenic response such as aluminum phosphate, hydroxide, or sulphate and stearyl tyrosine. The vaccines produced according to this invention may also be used as components of multivalent vaccines which elicit an immune response against a plurality of infectious agents.

Vaccines of the present invention are administered in amounts sufficient to elicit production of antibodies as part of an immunogenic response. Dosages may be adjusted based on the size, weight or age of the individual receiving the vaccine. The antibody response in an individual can be monitored by assaying for antibody titer or bactericidal activity and boosted if necessary to enhance the response. Typically, a single dose is about 0.1 to 10 $\mu$g/kg.

F. Diagnostic Kits

In another preferred embodiment, the modified pneumolysin polypeptides of this invention or derivatives or fragments thereof may be used to produce safer diagnostic kits that do not incorporate pneumolysin toxin but can still indicate the presence of antibodies directed against *S. pneumoniae*. The presence of such antibodies can indicate prior exposure to the pathogen, and predict individuals who may be resistant to infection. An antibody reaction may be identified by any of the methods described in the art, including but not limited to an ELISA assay. Such knowledge is important, and can avoid unnecessary vaccination. The diagnostic kit may comprise at least one of the modified pneumolysin polypeptides of this invention or derivatives or fragments thereof and suitable reagents for the detection of an antibody reaction when the modified polypeptides or derivatives or fragments are mixed with a sample that contains antibody directed against pneumolysin.

Alternatively, the diagnostic kit may further comprise a solid support or magnetic bead or plastic matrix and at least one of the modified pneumolysin polypeptides of this invention or derivatives or fragments thereof.

In some cases, it may be preferred that the polypeptides or derivatives or fragments are labeled. Labeling agents are well-known in the art. For example, labeling agents include but are not limited to radioactivity, chemiluminescence, bioluminescence, luminescence, or other identifying "tags" for convenient analysis. Body fluids or tissues samples (e.g. blood, serum, saliva) may be collected and purified and applied to the diagnostic kit. The pneumolysin polypeptides, derivatives (pneumolysoid) or fragments may be purified or non-purified and may be composed of a cocktail of molecules. Antibodies within the sample may or may not react with the pneumolysin.

Solid matrices are known in the art and are available, and include, but are not limited to polystyrene, polyethylene, polypropylene, polycarbonate, or any solid plastic material in the shape of test tubes, beads, microparticles, dip-sticks, plates or the like. Additionally matrices include, but are not limited to membranes, 96-well micro titer plates, test tubes and Eppendorf tubes. In general such matrices comprise any surface wherein a ligand-binding agent can be attached or a surface which itself provides a ligand attachment site.

All publications, patents and articles referred to within the specification are herewith incorporated in toto, by reference into the application. The following examples are presented to illustrate the present invention but are in no way to be construed as limitations on the scope of the invention. One skilled in the art will readily recognize other permutations within the purview of the invention.

EXAMPLES

Materials and Methods

Bacterial Strains and Plasmids. *Streptococcus pneumoniae* serotype 14 (ATCC, 10801 University Boulevard, Manassas, Va. 20110-2209) was used in this study for isolation of genomic DNA. *E. coli* strain DH5 (Life Technologies, Gaithersburg, Md.) was used for initial cloning and production of plasmid DNA. *E. coli* strain BL21 (DE3)ompA, used for protein expression, was derived from BL21 (BE3) (Novagen) (see U.S. Pat. No. 5,439,808 for details). *S. pneumoniae* was grown overnight in Todd-Hewitt (TH) broth at 37 C. without shaking under 7.5% $CO_2$. . . *E. coil* strains were grown in Luria-Bertani (LB) broth, supplemented with carbenicillin (50–100 µg/ml) or kanamycin (50 µg/ml) as needed. The plasniid vectors pUC-19 and/or pBluescript II SK+ (Stratagene) were used for cloning fragments to be sequenced and the plasmids pET-17 b and pET-24 a (Novagen) were used for cloning fragments to be expressed.

SDS-PAGE. Protein samples were prepared as follows: 1.5 ml fractions were collected from cultures and the cells harvested by centrifugation. The cells were resuspended in 150 µl of protein loading buffer and boiled for 5 min to lyse the cells. Cell debris were removed by centrifugation and 10 µl of each supernatant were electrophoresed through an 8–16% gradient Tris-glycine "Laemmli" polyacrylamide gel (Novex) along with low molecular weight standards (Bio-Rad). Alternatively, crude extracts prepared for analysis of hemolytic activity were diluted 1:1 with protein loading buffer and 10–15 µl loaded onto the gel. The protein bands were visualized with Coomassie blue staining.

Example 1

Expression of Pneumolysin

*E. coli* strain BL21 (DE3) Δompa transformed with pET-17b or pET-24a containing the desired gene was grown with moderate aeration at 30° C. in LB supplemented with 0.4% glucose and 100 µg/ml of carbenicillin (for pET-17b constructs) or 50 µg/ml of kanamycin (for pET-24a constructs). When the $OD_{600}$ reached 0.6, IPTG was added to a final concentration of 0.4 mM (for pET-17b constructs) of 1 mM (for pET-24a constructs) and the cells were allowed to incubate for another 2 h for screening, or 5 h for larger scale production. To assay for pneumolysin levels, 1.5 ml aliquots were removed prior to induction and at various time points after induction and examined by SDS-PAGE.

Example 2

Cloning of the Pneumolysin Gene for *Streptococcus pneumoniae* Serotype 14

Genomic DNA was isolated from approximately 0.5 g *Streptococcus pneumoniae* serotype 14 using the method described above. This DNA served as the template for two pneumolysin-specific oligonucleotides in a standard PCR reaction. These oligonucleotides were designed to be complementary to the 5' and 3' flanking regions of the pneumolysin gene from *S. pneumoniae* serotype 2 and to contain XbaI restriction sites to facilitate the cloning of the fragment if desired. The sequence of the forward oligonucleotide was 5' AAC CTT GAT TGA TCT AGA TAA GGT ATT TAT GTT GG 3' (SEQ ID NO: 5) and the reverse oligonucleotide had the sequence 5' TCT TTT TGT CTC TAG AAT TCT CCT CTC CTA GTC 3'(SEQ ID NO: 6) . The PCR reaction conditions were as follows: 200 ng *S. pneumoniae* type 14 genomic DNA, the two oligonucleotide primers described above at 1 μM of each, 200 μM of each dNTP, PCR reaction buffer (10 mM Tris HCl, 50 mM KCl, pH 8.3), 1.5 mM $MgCl_3$, and 2.5 units of Taq polymerase, and QS. to 100 μl with $dH_2O$. This reaction mixture was then subjected to 25 cycles of 95° C. for 1 min, 50° C. for 2 min and 72° C. for 1.5 min. At the end of the cycling period, the reaction mixture was loaded on a 1.0% agarose gel and the material was electrophoresed for 2 h after which the band at 1.7 kb was removed and the DNA recovered using GeneClean® (Bio 101). This DNA was then digested with XbaI, repurified and ligated to XbaI-digested pUC-19 using T4 DNA ligase. The ligation mixture was used to transform competent *E. coli* DH5α. Recombinant plasmids were identified and sequenced; many were found to have a DNA sequence consistent with that of the gene encoding pneumolysin.

Example 3

Expression of the Pneumolysin Gene in *E. coli*

Plasmids capable of expressing the mature pneumolysin protein were constructed by amplifying DNA containing the full-length pneumolysin gene (pST20, pST85, or type 14 genomic DNA) with nested oligonucleotides designed to isolate the pneumolysin coding region. The forward oligonucleotide was designed to contain a NdeI site and would install a start codon at the 5' end of the coding region. This primer had the sequence 5' TAT TAG GAG GAG CAT ATG GCA AAT AAA GCA GTA AAT G 3'(SEQ ID NO: 7) . The reverse oligonucleotide was designed to contain an XhoI site and had the sequence 5' GGC CTC TTT TTG TCT CGA GCA TTC TCC TCT CCT AGT C 3'(SEQ ID NO: 8). This strategy allowed the cloning of the fragment encoding mature pneumolysin into the NdeI and XhoI sites of either the pET-17b or pET-24a. Standard PCR was conducted using a template containing the entire pneumolysin gene (type 1, 2 & 14) and the two oligonucleotides described above. This PCR reaction yielded a 1.6 kb product when analyzed on a 1.0% agarose gel. The DNA obtained from the PCR reaction was gel purified and digested with the restriction enzyme NdeI and XhoI. The 1.6 kb product was again gel purified and ligated to NdeI- and XhoI- digested pET-17b or pET-24a using T4 DNA ligase. This ligation mixture was then used to transform competent *E. coli* DH5α. Colonies that contained the 1.6 kb insert were chosen for further analysis. The DNA from the DH5α clones was analyzed by restriction mapping and the cloning junctions of the chosen plasmids were sequences. After this analysis, the DNA obtained from the DH5α clones was used to transform *E. coli* BL21 (DE3)ΔompA. The transformed bacteria were selected on LB-agar containing 100 μg/ml of carbenicillin, or 50 μg/ml of kanamycin when using the pET-24a plasmid. Typically, several clones were screened for their ability to produce the mature pneumolysin protein.

Example 4

Random Mutagenesis to Generate Modified Pneumolysin

A portion of the gene encoding pneumolysin comprising amino acid residues 1–257 was subjected to random mutagenesis using a modification of the technique as described. (Cadwell, R. C. and Joyce, G. F. (1994) *PCR Methods Appl.* 3:pS136–40; Cadwell, R. C. and Joyce, G. F. (1992) *PCR Methods Appl.* 2:28–33). An oligonucleotide complementary to the T7 promoter region of the pET-24a plasmid (See, FIGS. 1 and 1B) with the sequence 5'ATT ACG CGA CTC ACT ATA GGG 3' (SEQ ID NO: 9) and an oligonucleotide complementary to a region of the pneumolysin gene around 1250 bp (See FIGS. 1A and 1B) with the sequence 5'ATT ACG AAC ATT CCC TTT AGG3' (SEQ ID NO: 10) were used to define the region of the gene to be mutated. The random mutagenesis PCR reaction conditions were as follows: purified plasmid pNV-19.2 (100 ng), the two oligonucleotide primers described above at 1 μM of each imbalance dNTP concentrations of 0.2 mM dGTP, 0.2 mM dATP, 1 mM dCTP, and 1 mM dTTP, PCR reaction buffer (19 mM Tris-HCl, 50 mM KCl, pH 8.3), 8.0 mM MgCl$_2$, 0.5 mM MnCl$_2$, 6 units Taq polymerase, and QS to 100 μl with dH$_2$O. This reaction mixture was then subjected to 40 cycles of 95° C. for 1 minute, 40° C. for 2 minutes, and 72° C. for 3 minutes. After the PCR reaction, fragments were extracted with phenol/chloroform and ethanol precipitated. The fragment was then digested with NdeI and HindIII, gel purified and ligated to pNV-19.2, digested with the same enzymes. The fragments were ligated and subsequently transformed into competent BL21 (DE3) *E. coli*.

Example 5

Selection of Modified Pneumolysin Expressing Modified Pneumolysin Devoid of Toxic Effects The transformation described by Example 4 resulted in numerous colonies (approximately 10$^4$) of which 400 were selected randomly for evaluation. The novel screening method described in this example was used to identify colonies that expressed modified pneumolysin polypeptides with the following characteristics: 1) no hemolytic activity, 2) substantially full-length, 3) partially soluble, and 4) monomeric and refoldable when isolated from inclusion bodies. This screening method involved the following steps:

(a) Testing for Presence of Low Hemolytic Activity:

A micro-hemolytic assay was used to evaluate the clones. Hemolytic activity-assays were conducted in U-bottom micro titer plates using TBS (Tris-buffered saline, pH 7.4) as an incubation buffer. Following a pre-incubation period of 5 min with 1 mM DTT, twofold serial dilutions were performed and the samples incubated with an identical volume of a 1% suspension of washed sheep erythrocytes (Cappel) resuspended in the same buffer. The reactions were conducted at room temperature as a function of time (kinetic study), and the extent of erythrocyte lysis was monitored by visual inspection. Each clone undergoing evaluation was scored from 0–5. A rank of zero indicated no hemolytic activity while a rank of 4–5 indicated hemolytic activity at wild-type levels or above. Two hundred clones with a score of 0, 1, 2, were selected and screened again for other desired properties.

(b) Testing for Expression of Full-length Pneumolysin Polypeptide:

The polypeptide expression assay was carried out in a 96-well format. Colonies with low hemolytic activity were evaluated by SDS-PAGE for the presence of a strong band having a molecular weight of about 53,000 Daltons. Full-length pneumolysin has a molecular weight of about 53 kD. Fifty-eight out of 200 were found positive in this assay. These clones were collected for further selection.

(c) Testing for Expression of Modified Pneumolysin Polypeptides in the Soluble Fractions:

Modified pneumolysin polypeptides expressed in both the soluble fraction and inclusion bodies are more likely to be refoldable. Ten ml cultures from 2h IPTG-induced *E. coli* cells harboring plasmids containing mutant pneumolysin sequences lacking or exhibiting reduced hemolytic activity were harvested and resuspended in 1.5 ml of TEN buffer; the cells are lysed by a sequential freezing/thawing/sonication procedure until the supernatant exhibits significant levels of protein, as indicated by the Bradford protein assay, which is indicative of successful lysis. The lysed cell suspension is centrifuged (14,000 rpm/10 min) and aliquots of both, the pellet and supernatant are analyzed by SDS-PAGE. An aliquot of the soluble fraction is tested for hemolytic activity and the hemolytic titer is determined to confirm the reduced activity observed in the kinetic qualitative study conducted in the initial phase of screening. Clones were found that contained soluble, modified pneumolysin polypeptides that had little hemolytic activity.

(d) High Yields of Refoldable and Monomeric, Modified Pneumolysin Polypeptides:

Clones containing soluble pneuniolysin are selected for the next step in the screening procedure, which consists of discarding the supernatant by aspiration, washing the pellet with TEN buffer twice, and solubilizing the pellet in 5 ml of 8 M urea prepared in TEN buffer. After sonicating for 2 min, the urea solution is quickly centrifuged to remove aggregates and added dropwise to 45 ml of refolding solution, under constant stirring at 4° C. The refolding solution is then loaded onto a 2 ml DEAE-SEPHAROSE-FF column, pre-equilibrated in Buffer A (25 mM Tris.HCl, pH 8.0). The column is washed with Buffer A and the bound protein is eluted with a gradient of 0 to 1 M NaCl. The properly refolded pneumolysin mutant should elute as a single peak between 13 and 20% Buffer B (25 mM Tris.HCl, 1 M NaCl, pH 8.0) similarly to what is observed for the wild-type. The protein peak is further analyzed by HPLC on a SUPEROSE 12 column and both elution time, aggregate/monomer ratio, and hemolytic activity are evaluated (see Table 4). The selected mutant(s) should present a single monomeric species with a Stokes radius comparable to the wild-type. Five clones (pNVJ1, pNVJ20, pNVJ22, pNVJ45, pNVJ56) with high yields of monomeric modified polypeptides were selected for further analysis including nucleic acid sequencing. The amino and nucleic acid substitutions of these clones are shown in Tables 5A and 6. Throughout the specification and claims, proteins are given the name of the vector that encodes them.

TABLE 4

Comparison of Wild-Type (pNV19) And Mutant Pneumolysin Polypeptides

| Protein | Pure Monomer (mg/L) | HPLC (Elution time) | Hemolytic activity (U/mg) | Activity (% wild type) |
|---|---|---|---|---|
| pNV19 | 63 | 20.1 | $10^6$ | 100 |
| pNV111 | 92 | 19.3 | 2,555(9)[1] | 0.25 |
| pNVJ22 | 86 | 20.7 | 2,440(9) | 0.24 |
| pNVJ20 | 90 | 19.8 | 1,961(6) | 0.20 |
| pNVJ1 | 66 | 20.2 | 1,536(2) | 0.15 |
| pNVJ45 | 86 | 18.7 | 1,360(5) | 0.14 |
| pNVJ56 | 104 | 19.8 | 2,000(2) | 0.20 |
| pNV211 | n.d. | 20 | 1800(2) | 0.18 |
| pNV207 | 100 | 20.5 | 800(2) | 0.08 |
| pNV103 | 104.7 | 20 | 950(2) | 0.10 |

[1]Numbers in parenthesis indicate number of experiments.

TABLE 5A

Amino Acid Sequence of Wild-Type (pNV19) Pneumolysin and Modified Forms

| | $X_{aa17}$ | $X_{aa18}$ | $X_{aa33}$ | $X_{aa41}$ | $X_{aa45}$ | $X_{aa46}$ | $X_{aa61}$ | $X_{aa63}$ | $X_{aa66}$ | $X_{aa83}$ | $X_{aa101}$ | $X_{aa102}$ |
|---|---|---|---|---|---|---|---|---|---|---|---|---|
| Pnv19 | Lys | Lys | Ile | Asp | Val | Ile | Ser | Thr | Asn | Leu | Ile | Asp |
| pNVJ1 | Arg | Asn | — | — | — | — | Pro | — | Tyr | — | Thr | — |
| pNVJ45 | — | — | — | Gly | — | — | — | — | — | — | — | — |
| pNVJ20 | — | — | — | — | — | — | — | Ser | — | — | — | — |
| pNVJ22 | — | — | Thr | — | — | Thr | — | — | — | Ser | — | — |
| pNVJ56 | — | — | — | — | Ala | — | — | — | — | — | — | Gly |
| pNV103 | — | — | — | — | — | — | — | — | — | — | — | — |
| pNV207 | — | — | — | — | — | — | — | — | — | — | — | — |
| pNV111 | — | — | — | — | — | — | — | — | — | — | — | — |
| pNV211 | — | — | — | — | — | — | Pro | — | — | — | — | — |

| | $X_{aa127}$ | $X_{aa128}$ | $X_{aa148}$ | $X_{aa172}$ | $X_{aa189}$ | $X_{aa195}$ | $X_{aa239}$ | $X_{aa255}$ | $X_{aa257}$ |
|---|---|---|---|---|---|---|---|---|---|
| Pnv19 | Val | Asn | Met | Thr | Gln | Phe | Ser | Lys | Asp |
| pNVJ1 | — | — | — | — | — | — | — | — | — |
| pNVJ45 | — | — | — | Ala | — | Ile | — | Gly | — |
| pNVJ20 | Glu | His | Lys | — | — | — | — | — | — |
| pNVJ22 | — | — | — | — | — | — | Arg | — | Gly |
| pNVJ56 | — | — | — | — | Arg | Val | — | — | — |
| pNV103 | — | — | — | — | — | Val | — | — | — |
| pNV207 | — | — | — | — | — | Ile | — | — | — |
| pNV111 | — | — | Lys | — | — | — | — | — | — |
| pNV211 | — | — | — | — | — | — | — | — | — |

TABLE 5B

Amino Acid Sequence of Modified Pneumolysin Polypeptides

| Protein | Mutation | Hemolytic activity |
|---|---|---|
| pNV19 | wild-type | 100% |
| pNV21 | 446 P to S | 25% |
| pNV46 | 286 E to D | 12% |
| pNV22 | 243 G to R, 446 P to S | <1% |
| pNV38 | 243 G to V | <1% |
| pNV39 | 243 G to E | <1% |

TABLE 5B-continued

Amino Acid Sequence of Modified Pneumolysin Polypeptides

| Protein | Mutation | Hemolytic activity |
|---|---|---|
| pNV40 | 243 G to S | <1% |
| pNV20 | 243 G to R | <1% |

TABLE 6

Nucleic acid substitutions to the wild-type (pNV19) pneunsolysin gene which resulted in dramatically reduced hemolytic activity

|  | $N_{50}$ | $N_{54}$ | $N_{98}$ | $N_{122}$ | $N_{134}$ | $N_{137}$ | $N_{181}$ | $N_{187}$ | $N_{196}$ | $N_{248}$ | $N_{302}$ | $N_{305}$ |
|---|---|---|---|---|---|---|---|---|---|---|---|---|
| pNV19 | A | G | T | A | T | T | T | A | A | T | T | A |
| pNVJ1 | G | T | — | — | — | — | C | — | T | — | C | — |
| pNVJ45 | — | — | — | G | — | — | — | — | — | — | — | — |
| pNVJ20 | — | — | — | — | — | — | — | T | — | — | — | — |
| pNVJ22 | — | — | C | — | — | C | — | — | — | C | — | — |
| pNVJ56 | — | — | — | — | C | — | — | — | — | — | — | G |
| pNV103 | — | — | — | — | — | — | — | — | — | — | — | — |
| pNV207 | — | — | — | — | — | — | — | — | — | — | — | — |
| pNV111 | — | — | — | — | — | — | — | — | — | — | — | — |
| pNV211 | — | — | — | — | — | — | C | — | — | — | — | — |

|  | $N_{380}$ | $N_{382}$ | $N_{443}$ | $N_{514}$ | $N_{566}$ | $N_{583}$ | $N_{717}$ | $N_{764}$ | $N_{770}$ |
|---|---|---|---|---|---|---|---|---|---|
| pNV19 | T | A | T | A | A | T | T | A | A |
| pNVJ1 | — | — | — | — | — | — | — | — | — |
| pNVJ45 | — | — | — | G | — | A | — | G | — |
| pNVJ20 | A | C | A | — | — | — | — | — | — |
| pNVJ22 | — | — | — | — | — | — | A | — | G |
| pNVJ56 | — | — | — | — | G | G | — | — | — |
| pNV103 | — | — | — | — | — | G | — | — | — |
| pNV207 | — | — | — | — | — | A | — | — | — |
| pNV111 | — | — | A | — | — | — | — | — | — |
| pNV211 | — | — | — | — | — | — | — | — | — |

Example 6

Site Directed Mutagenesis of Pneumolysin Gene with Single Mutation

To dissect whether a single mutation or multiple mutations are responsible for the loss of hemolytic activity in specific peptides (Table 4), each mutation was introduced into the wild-type allele as a single-site mutation using oligonucleotide directed mutagenesis. Table 7 presents the oligonucleotides used to introduce these specific mutations. Polypeptides carrying desired mutations were identified and their nucleic acid sequences confirmed. The following polypeptides with single base changes that resulted in a loss of hemolytic activity from these site-directed polypeptides were identified (See Table 5A): nucleic acid sequence 103 contains a single base change at 583 from wild-type T to modified G (195-Phe→Val); nucleic acid sequence 207 contains a single base change at 583 from wild-type T to modified A (195-Phe→Ile); nucleic acid sequence 111 contains a single base change at 443 from wild-type T to modified A (148-Met→Lys); nucleic acid sequence 211 contains a single base change at 181 from wild-type T to modified C (61-Ser→Pro).

The polypeptides shown in Table 5B exhibited poor refolding yields, explaining their reduced hemolytic activity. Single mutations introduced into pneumolysin polypeptide at positions 243, 286 and 446 or a combination of substitutions introduced at positions 243 and 446 produced species found exclusively in the insoluble fraction as inclusion bodies. Attempted refolding of these mutants yielded mostly aggregated species.

TABLE 7

Modified Pneumolysin Sequences

| MUTATION POSITION | AA # | Primer Sequence |
|---|---|---|
| 443 | 148 | Forward (SEQ ID NO: 11)<br>5'ggtcaggtcaataatgtcccagctagaaAgcagtatg 3' |
|  | Met-Lys | Reverse (SEQ ID NO: 12)<br>5'gctgtgagccgtgattttttcatactgcTttCtagCtg 3' |
| 583 | 195 | Forward (SEQ ID NO: 13)<br>5'gcagattcagattgttaatGttaagcagatttattata 3' |
|  | Phe-Ile | Reverse (SEQ ID NO: 14)<br>5'atctgcttaaCattaacaatctgaatctgCttttCgCC 3' |
| 583 | 195 | Forward (SEQ ID NO: 15)<br>5'cagattgttaatAttaagcagatttattataCagtCagc3' |
|  | Phe-Val | Reverse (SEQ ID NO: 16)<br>5'aatctgcttaaTattaacaatctgaatctgcttttcgcc3' |

TABLE 7-continued

Modified Pneumolysin Sequences

| MUTATION POSITION | AA # | Primer Sequence |
|---|---|---|
| 181 | 61 | Forward (SEQ ID NO: 17) 5'acaagtgatattcctgtaacagctaccaa cgacagtcgc3' |
| | Ser-Pro | Reverse (SEQ ID NO: 18) 5'agctgttacagGaatatcacttgtatttg tcgacaagCt3' |

Example 7

Expression and Purification of Modified Polypeptides

These single mutated genes were cloned into expression vectors (pET-24a) individually to overexpress the modified polypeptides in *E. coli*. The expression level is ~40%. Novel purification and refolding processes were developed to purify these recombinant modified pneumolysins.

Pneumolysin expressed in *E. coli* cells harboring the expression vector pNV19 was isolated from inclusion bodies by resuspending and lysing the cells in TEN buffer (50 mM Tris-HCl, 100 mM NaCl, 10 mM EDTA pH 8.0), with an air driven cell disrupter (Stansted Fluid Power Ltd.) under a pressure of 8,000 psi. The cell lysate was centrifuged at 13,000 rpm at 4 C. for 20 minutes; both pellet and supernatant were saved for isolation of soluble and aggregated pneumolysin, respectively. The inclusion bodies were washed three times with TEN buffer and stored at -70 C. Purification and subsequent refolding were achieved by solubilizing the inclusion bodies in an 8 M urea solution (freshly prepared in TEN buffer), followed by PEG-assisted refolding. Polypeptide solutions in 8 M urea (200 µg/ml) were diluted 10-fold by drop-wise addition to a refolding solution, consisting of 20 µM of PEG 8,000 in 25 mM Tris-HCl, pH 8.0 under constant stirring at 4 C. The sample was clarified and loaded into a DEAE- SEPHAROSE Fast Flow ion exchange column (Pharmacia) equilibrated in 25 mM Tris-HCl, pH 8.0. A gradient of 0–1 M NaCl was applied and pneuniolysin containing fractions were identified by detection of hemolytic activity, as described below, and by SDS-PAGE. The purified fractions were concentrated by using an Amicon concentrator and PM30 membrane. Aliquots of purified polypeptide were tested for hemolytic activity, and analyzed by SDS-PAGE and size exclusion chromatography, using a SUPEROSE 12 column.

Hemolytic activity assays were conducted in U-bottom micro-titer plates using TBS (Tris buffered saline, pH 7.4) as an incubation buffer. Following a pre-incubation period of 5 minutes with 1 mM DTT, twofold serial dilutions of normalized proteins were performed and the samples incubated with an identical volume of a 1% suspension of washed sheep erythrocytes (total volume 200 µl) (Cappel) resuspended in the same buffer. The reactions were conducted at 37° C. for 30 minutes and the extent of erythrocyte lysis was monitored spectrophotometrically by spinning down the U-plates transferring the supernatant to flat-bottomed plates and measuring the extent of hemoglobin release at 450 nm. The end point was set to be the concentration at which 50% lysis occurred and was based on comparison with a 0.5% cell suspension that was lysed hypotonically (see Tables 4 and 5B).

Another method of assaying the modified pneumolysin polypeptides is to conduct a hemolysis inhibition assay of the modified polypeptides. This assay consists of determining the ability of the mutant proteins to reduce or eliminate the hemolytic activity of the wild-type protein by pre-incubating erythrocytes with the modified pneumolysin polypeptides and assessing the hemolytic titer of the wild-type pneumolysin toward the pre-treated erythrocytes. The results from using this assay with four modified polypeptides are given in Table 8, and a detailed description of the procedure appears in Example 11.

TABLE 8

Hemolysis inhibition assay of pneumolysin by the pneumolysin mutants

| Designation | Mutation | End point (*) |
|---|---|---|
| pNV19 | wild-type | 512 |
| pNV103 | Phe$^{195}$Val | 64 |
| pNV111 | Met$^{148}$Lys | 128 |
| pNV207 | Phe$^{195}$Ile | 32 |
| pNV211 | Ser$^{61}$ Pro | 512 |

(*) Reciprocal of the hemolytic titer of a wild-type pneumolysin preparation in the presence of the indicated mutant The antigenic cross-reactivity of the selected single site pneumolysin mutants was determined by immunizing rabbits (n=2) with each of the mutant proteins shown in Table 9 by conventional immunization procedures. Immunization of rabbits: New Zealand White rabbits (Covance, Denvers, Pa.) weighing 2–3 kg were immunized subcutaneously with 100 µg of wild-type or mutant pneumolysin emulsified with complete Freund's adjuvant, (Vol/Vol). Booster doses of vaccine mixed with incomplete Freund's adjuvant were administered by the same route 21 and 42 days after the primary dose. Sera were collected on day 0, 21, 42, and 52. The sera were tested for the presence of antibodies against wild-type pneumolysin. The antigenic titer of pooled sera (n=2) towards type 14 pneumolysin was determined by ELISA. In brief, plates were coated with wild-type pneumolysin and incubated with serial dilutions of each of the anti-mutant pneumolysin sera. Significant binding of wild-type pneumolysin to antibodies elicited by the modified pneumolysin polypeptides was observed as shown in Table 9.

TABLE 9

Reactivity and hemolysis neutralizing titer of mutant pneumolysin rabbit antisera towards type 14 pneumolysin by ELISA

| Designation | Mutation | Titer | Antibody Neutralizing Titer |
|---|---|---|---|
| pNV19 | wild-type | 892,647 | 256 |
| pNV211 | Ser$^{61}$Pro | 432,100 | 128 |
| pNV111 | Met$^{148}$Lys | 296,113 | 128 |
| pNV103 | Phe$^{195}$Val | 2,505,208 | 512 |
| pNV207 | Phe$^{195}$Ile | 402,426 | 128 |
| PBS | — | — | 8 |

As can be seen in Table 9, antisera to each of the above polypeptides, in addition to their strong cross-reaction with the wild-type pneumolysin as measured by ELISA, have significant neutralizing, anti-hemolytic titers as measured in a hemolysis inhibition assay.

Example 8

Preparation of Pneumolysoid Conjugates
Preparation of Polysaccharide for Conjugation PnC type 14 polysaccharide (ATCC Lot #2016107) (390 mg) was dissolved in 16 ml of 0.5 N NaOH, and the solution was heated at 70 C. for 3 hours. Following cooling of the solution, 1.93 ml of glacial acetic acid was added to bring the pH to 4. After addition of 3 ml of 5% (w/v) $NaNO_2$, the reaction mixture was kept stirring at 4 C for 2 hours. The sample was then diluted to 50 ml with deionized water and the pH was adjusted to 7 with 0.5 N NaOH. Excess reagents were dialyzed out by diafiltration with DI water through a SPECTRAIPOR molecular porous membrane tubing (MWCOL:3,500), and the retentates freeze-dried. The deaminated type 14 polysaccharide was then molecular sieved on a SUPERDEX G-200 (Pharmacia) column using PBS as eluent. Fractions eluting from the column with molecular weight between 5000 and 15,000 as determined by Chromatography/Multiangle Laser Light Scattering using a SUPEROSE 12 column (Pharmacia) were pooled and dialyzed against DI water through a SPECTRA/POR molecular porous membrane tubing (MWCOL 3,500) and freeze-dried.

Preparation of Conjugates

Each of the PnCPS were first depolymerized and functional aldehydes were introduced into the fragmented CPS by oxidation with sodium metaperiodate. Following the oxidation process, the excess periodate was destroyed with ethylene glycol, the oxidized polysaccharides were dialysed against DI water and lyophilized.

Modified pneumolysin polypeptides in 0.2 M phosphate buffer (pH 8) at a concentration of 5 mg/ml were mixed with 2.5 equivalents (by weight) of PnC 14 polysaccharide-fragment together with 2 equivalents (by weight) of recrystallized sodium cyanoborohydride. Reaction mixtures were incubated at 37° C. for 24 hours. Conjugates were then purified from the free components by passage through a SUPERDEX G200 (Pharmacia) column using PBS containing 0.01% thimerosal as an eluent. Fractions eluting from the column were monitored on a Waters R403 differential refractometer and by UV spectroscopy at 280 nm. The fractions containing the conjugates were pooled, sterile-filtered through a 0.22 µm Millipore membrane and then stored at 4 C. Polypeptide and carbohydrate content were measured by the methods of Bradford and Dubois respectively. Polysaccharide content in the resulting conjugates were approximately 30%.

Tetanus toxoid conjugates for use as control, were also produced as described above and as follows: Tetanus toxoid (Serum Statens Institute) was first passed through a molecular sieve column (SUPERDEX G-200 Pharmacia) in order to obtain the monomer form of the toxoid. For conjugation, 12 mg of the monomer and 36 mg of the PnC 14 polysaccharide-fragments were dissolved in 600 d of 0.2 M phosphate buffer pH 7.2. Recrystallized sodium cyanoborohydride (24 mg) was then added to the solution which was then incubated at 37° C. for 3-days. The conjugate was purified as above. The conjugates had polysaccharide contents in the 25–30% range (see Table 10).

TABLE 10

Composition of Tetanus-Toxoid and Modified Pneumolysin type 14 Conjugates

| Carrier Polypeptide | Approx. MW of PS | Polypeptide (mg/ml) | PS (mg/ml) | % PS in Conjugate |
|---|---|---|---|---|
| pNV103 #195 Phe-Val | 9,000 | 0.170 | 0.079 | 32% |
| pNV207 #195 Phe-Ile | 9,000 | 0.117 | 0.048 | 29% |
| pNV111 #148 Met-Lys | 9,000 | 0.145 | 0.062 | 30% |
| pNV19 Wild-type | 9,000 | 0.115 | 0.049 | 30% |
| Tetanus Tm | 9,000 | 0.245 | 0.098 | 28% |

Example 9

Immunization with Modified Pneumolysin Conjugates

Groups of 20 CD1 female mice (age 6–8 weeks), from Charles River Laboratories, were immunized subcutaneously (S.C.) with 2 µg of the conjugated polysaccharides of Example 8 adsorbed on aluminum (Aluminum hydroxide, Superfos, Denmark) at a concentration of 1 mg of elemental aluminum per ml of PBS containing 0.01% thimerosal. Mice received the vaccine at day 0, 28, and 49. Sera were collected at day 0, 42, and 59, and stored at −70° C.

ELISA

Micro titer plates (Nunc Polysorb ELISA plates) were sensitized by adding 100 µl of type 14 polysaccharide-fragment (MW ca: 10,000)/HSA conjugate (2.5 µg/ml) in PBS. The plates were sealed and incubated at 37 C. for 1 hour. The plates were washed with PBS containing 0.05% TWEEN 20 (PBS-T) and blocked with 0.5% (w/v) BSA in PBS for 1 hour at room temperature. The wells were then filled with 100 µl of serial two-fold dilutions in PBS-T plates, 100 µl of peroxidase labeled goat anti-mouse IgG (H+L) (Kirkegaard and Perry Laboratories), and then washed five times with PBS-T. Finally, 50 µl of TMB peroxidase substrate (Kirkegaard and Perry Laboratories) were added to each well, and following incubation of the plates for 10 minutes at room temperature, the reaction was stopped by the addition of 50 ul of 1 M $H_3PO_4$. The plates were read at 450 nm with a Molecular Device Amex microplate reader using 650 nm as a reference wavelength. Inhibition ELISA Assay.

Microtiter plates (NUNC Polysorp) were coated with PLY (20 ng in 100 mL to each well) in PBS (50 mM sodium phosphate, 150 mM NaCl, pH 7.4) for one hour at 37° C. After washing the plates with PBS+0.05% TWEEN 20 (PBST), the plates were post-coated with 150 mL of PBS+ 0.1% BSA, rewashed, and stored at 4° C. until used.

Hyperimmune rabbit anti-PLY was diluted in PBST, added to the PLY coated plates, and incubated at room temperature for 1 h. After washing, 100 mL of goat anti-rabbit Ig-HRP conjugate (KPL) diluted in PBST according to the manufacturer's instructions were added to each well. The plate was incubated at room temperature for one hour and then washed again. 100 mL of TMB microwell substrate (KPL) were added to each well. The reaction was stopped after 10 minutes by the addition of TMB one-component stop solution (KPL) and the $OD_{450\ nm}$ was immediately read. The dilution corresponding to ½ the maximum signal was chosen for the inhibition study. PLYD mutants as well as PLY as a control were diluted serially in three-fold ingrements in PBST containing the rabbit antiserum diluted such that the final mixture contained the dilution which gave half-maximal activity and applied immediately to the coated microtiter plates in duplicate. The plates were incubated at room temperature for one hour and processed. Inhibition was determined as percent of maximum signal achieved with dilute antiserum in the absence of any inhibitor.

Opsonic Activity of Conjugate Antisera

The opsonic ability of mice antisera to the PnC type 14 conjugates was tested in an in vitro opsonophagocytic killing assay using the human promyelocytic leukemia HL-60 cell line (ATCC #CCL240). (See Table 11). Briefly, 200 cfu of PnC type 14 (12-8-95 CB) cells were mixed in equal volume with serially diluted antibodies and incubated 15 minutes under shaking at 37° C. in a 5% $CO_2$ incubator. Baby rabbit complement and HL-60 cells ($5 \times 10^5$) cultured 5-days in the presence of 90 mM dimethylformamide were added to the mixture which was then incubated at 37° C. for 1 hour under shaking. Aliquots were removed for quantitative culture and plated on chocolate agar. Titers were determined by extrapolating the antibody dilution corresponding to 50% live bacteria.

TABLE 11

Immunogenicity of PnC 14 Polysaccharide Conjugates

| Carrier | ELISA Titer at Day | | | Op+ Titer at Day | ELISA titer to wild-type pneumolysin at Day |
|---|---|---|---|---|---|
| | 0 | 42 | 59 | 59 | 59 |
| Polypeptide | | | | | |
| Tetanus Toxoid | <50 | 287,000 | 170,000 | 28,000 | <50 |
| pNV103 #195 Phe-Val | <50 | 209,000 | 178,000 | 18,000 | 124,000 |
| pNV207 #195 Phe-Ile | <50 | 175,000 | 149,000 | 31,000 | 111,000 |
| pNV111 #148 Met-Lys | <50 | 137,000 | 127,000 | 10,500 | 84,000 |
| pNV19 Wild-type | <50 | 275,000 | 241,000 | 29,000 | 124,000 |
| PBS | <50 | <50 | <50 | <100 | |

*PnC 14 polysaccharide-specific antibody titer
+Opsonophagocytic Titer

As can be seen from the data in Table 11, all of the modified pneumolysin conjugates elicited antibodies which had opsonophagocytic activity in the presence of complement. Mice immunized with all the above conjugates, in addition to a strong IgG anti-PS response, mount a very strong IgG response against the pneumolysoid carriers and to the same extent as that raised against the conjugated wild-type pneumolysin.

Example 10

Preparation of Tetravalent 6B/14/19F/23F Pneumolysoid Vaccines

Preparation of Conjugates

The hydrolysis of polysaccharides was carried out as follows: type 6B PS was depolymerized with 0.1 N HCl at 60° C. for 3 hrs and 45 min; type 14 was depolymerized with 0.1N HCl at 60° C. for 7 hrs ; type 19F was depolymerized with a 10 mM NaOAc buffer of pH 4.1 at 70° C. for 2 hrs and 20 min; and type 23F was depolymerized with 0.2M acetic acid solution at 100° C. for 30 minutes.

Oxidized 6B PS was prepared as follows: the partially depolymerized PS (35 mg) was dissolved in 1750 ml DI water and treated with 250 ml of 10 mM $NaIO_4$ in the dark for 2 hrs at room temperature. The excess $NaIO_4$ was destroyed with ethylene glycol, and after extensive dialysis the oxidized PS was lyophilized. Oxidized 14 PS was prepared as described above for type 6B. Oxidized 19F was prepared as follows: 50 mg of depolymerized PS was dissolved in 0.2 M sodium phosphate buffer pH 7.5 (5 ml) and treated with 41 ml of 100 mM $NaIO_4$ at 4° C. overnight in the dark. Excess $NaIO_4$ destroyed with ethylene glycol and after extensive dialysis the oxidized 19F PS was lyophilized. Oxidized 23F was prepared as follows: 68 mg of partially depolymerized PS was dissolved in 3.4 ml of 3 mM $NaIO_4$ solution at room temperature in the dark for 1 hour. The excess $NaIO_4$ was destroyed by the addition of ethylene glycol, and after extensive dialysis, the oxidized PS was lyophilized to dryness.

The oxidized PSs were separately coupled to recombinant pneumolysoid mutant 207 in which amino acid Phe residue 195 was replaced by Ile. In brief, the oxidized PSs and the protein (5 mg/ml) in 0.2 M sodium phosphate buffer were combined at a PS/protein ratio of about 2.5:1 by weight at room temperature and sodium cyanoborohydride (2 equivalents by weight) was then added. The conjugation mixtures were incubated at 37 C. for 2 days. After reduction of the residual aldehydes of the conjugated PS, with excess $NaBH_4$, the conjugates were purified from the reaction mixtures by passage through a column of SUPERDEX 200 PG (Pharmacia) eluted with PBS containing 0.01% thimerosal as the preservative, except for the type 23 conjugate where the conjugate was loaded onto a Q SEPHAROSE Fast Flow column, and eluted with 10 mM Tris-HCl, pH 7.5 using a gradient of 0.5 M NaCl. Fractions corresponding to the conjugates were pooled and analyzed for protein and carbohydrate content as described in example 8 (see Table 12).

TABLE 12

Composition of pneumolysoid conjugates

| Pneumococcal Serotype | Approx. MW of PS | Polypeptide (mg/ml) | PS (mg/ml) | % PS in conjugate |
|---|---|---|---|---|
| 6B | 41,000 | 0.24 | 0.14 | 37 |
| 14 | 41,000 | 0.13 | 0.08 | 38 |
| 19F | 10,000 | 0.46 | 0.14 | 23 |
| 23F | 90,000 | 0.44 | 0.06 | 12 |

Example 11

Immunization with Pneumolysoid Tetravalent Vaccines

Immunization of Mice

Figure 8:
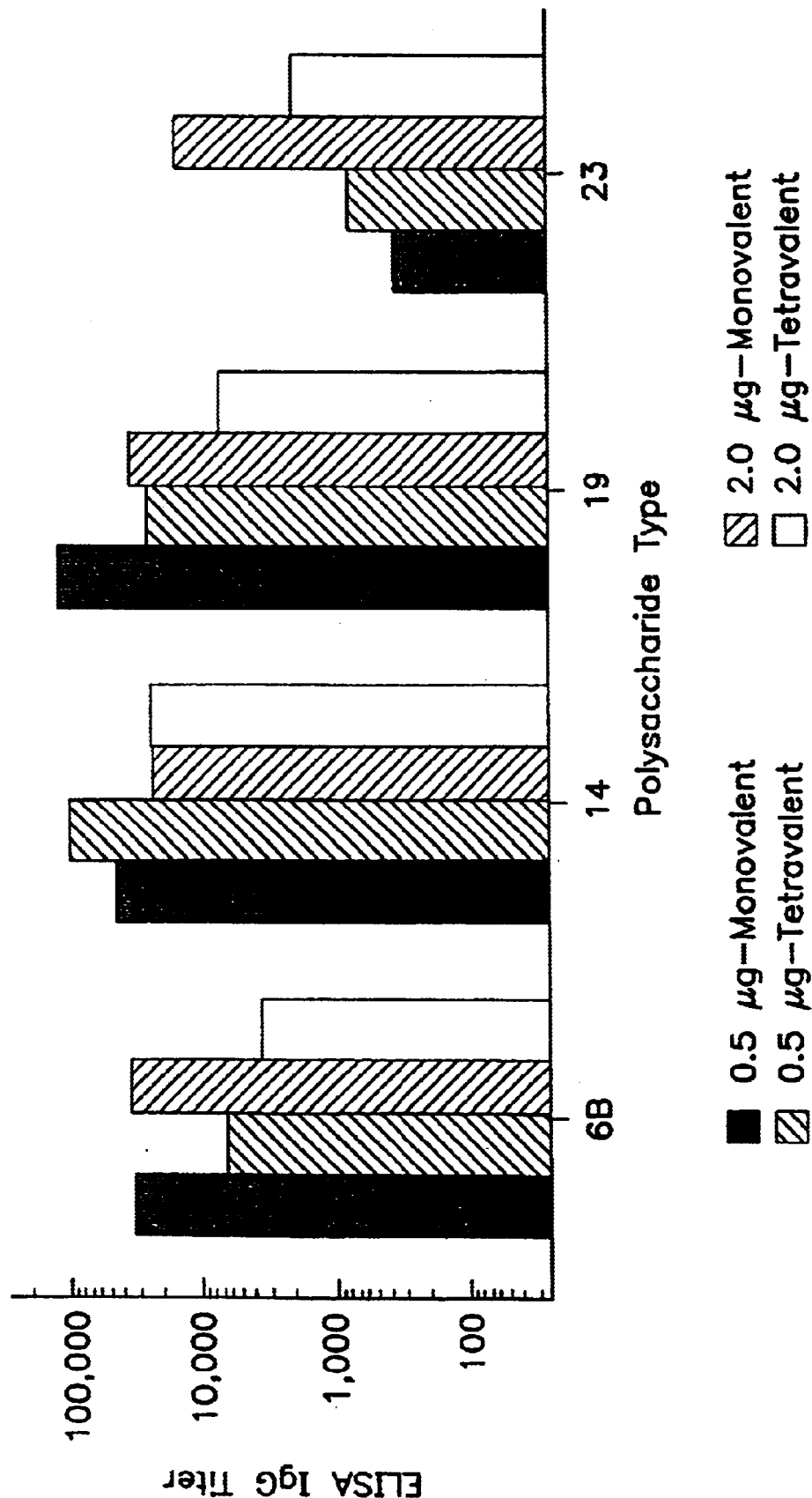
FIG. 8: Comparison of polysaccharide dose response of polysaccharide specific IgG following two injections of monovalent or tetravalent pneumococcal pneumolysoid vaccines in mice.
Figure 9:
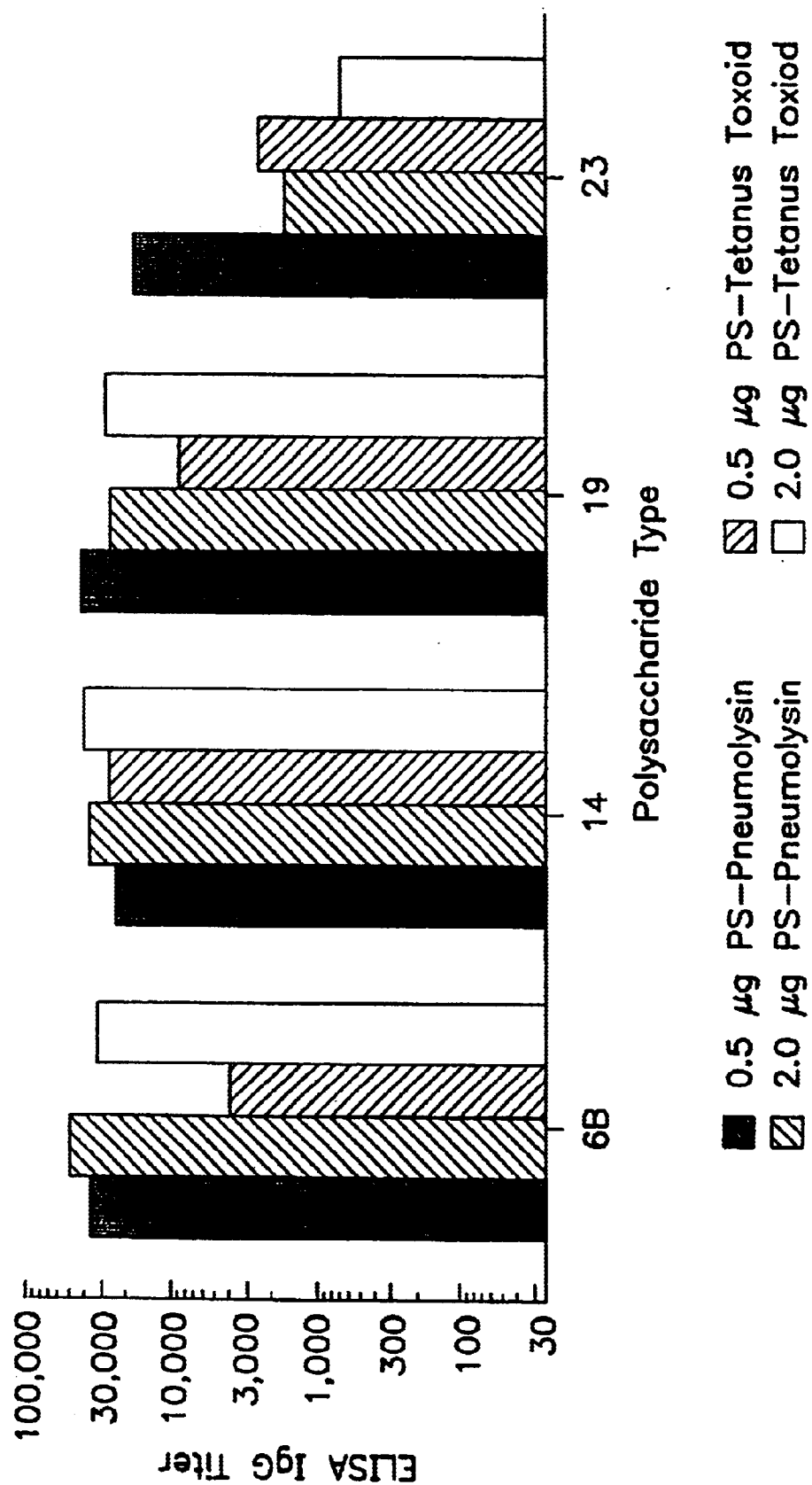
FIG. 9: Comparison of polysaccharide-specific IgG following two injections in mice of tetravalent pneumococcal vaccines conjugated to pneumolysoid or tetanus toxoid carriers.
Figure 10:
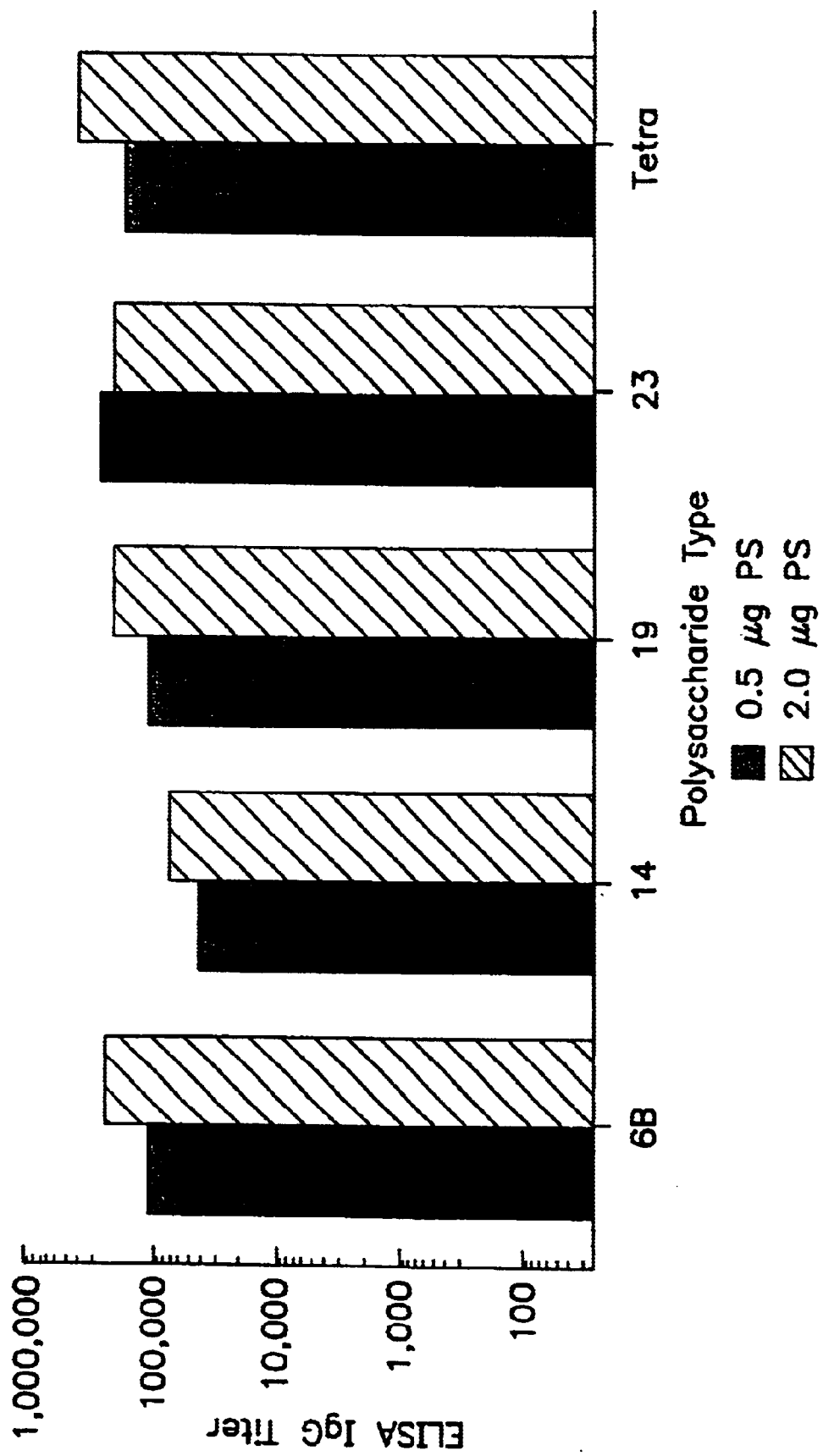
FIG. 10: Pneumolysoid-specific IgG elicited by monovalent and tetravalent pneumococcal polysaccharide-pneumolysin vaccines in mice after two injections.
Figure 11:
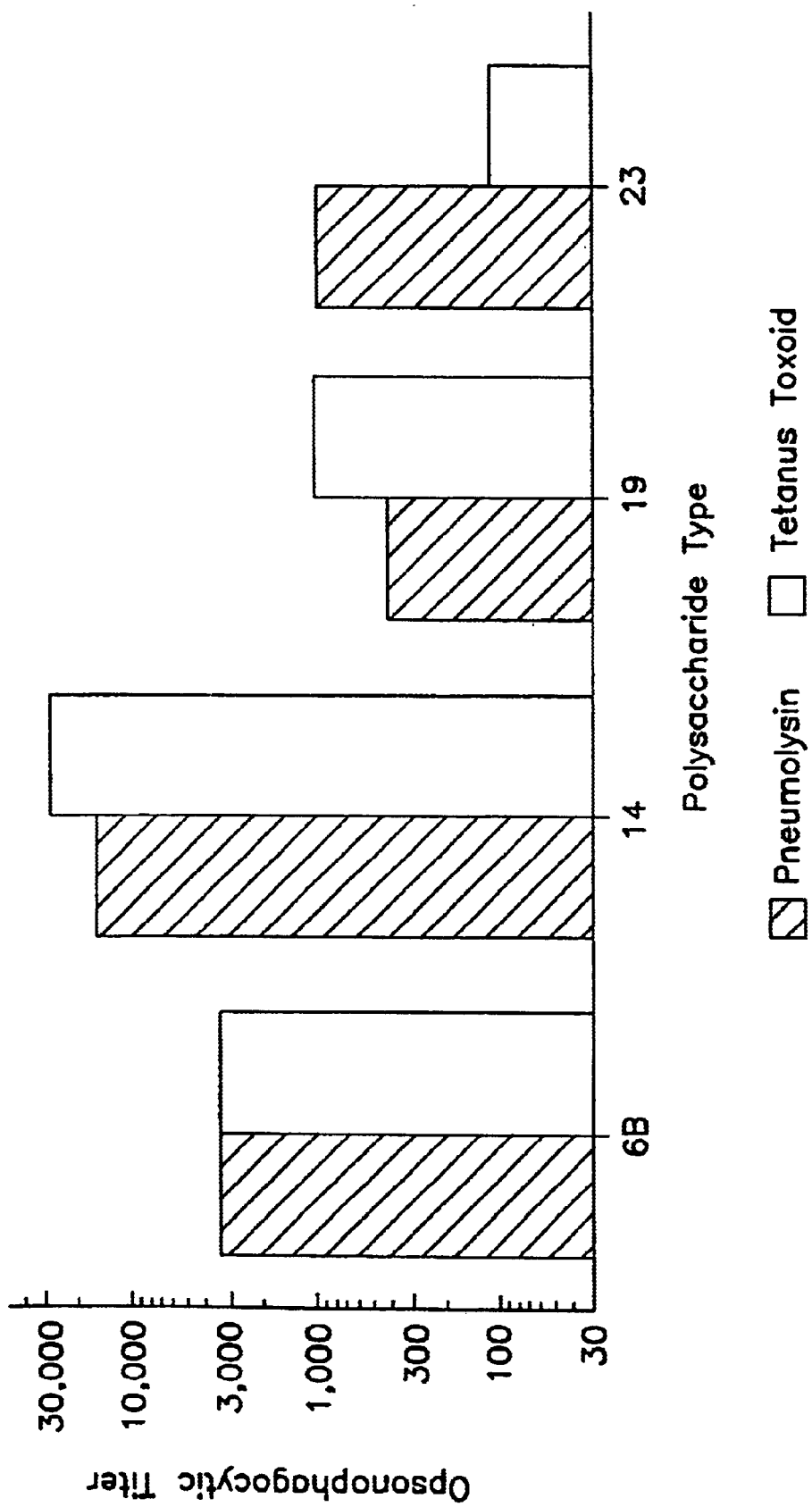
FIG. 11: Polysaccharide-specific opsonophagocytic activity elicited by tetravalent pneumococcal PS-pneumolysoid and PS-tetanus toxoid conjugate vaccines in mice after two injections.

Six to 8 weeks old female outbred CD-1 mice (Charles River, Raleigh) were immunized with monovalent or tetravalent vaccines. Streptococcus pneumoniae polysaccharides types 6B, 14, 19, and 23 were conjugated to tetanus toxoid or pneumolysin mutant (0.5 µg PS/0.2 ml to 2 µg PS/0.2 ml) in 1 mg/ml 1 alum. The vaccines were administered subcutaneously, on days 0, 28, and 49, and blood samples were collected on days 0, 14, 28, 38 and 59. ELISA titers against polysaccharides and the carrier protein were determined using HSA-PS conjugates and wild-type pneumolysin (FIGS. 8, 9 and 10). The opsonic activity of the sera was determined in a phagocytic assay using HL-60 cell line as described in Example 9 (FIG. 11).

Hemolysis Assay

The pneumolysin activity was assessed according to Paton et al. (1993) Infect. Immun. 40:548, with some modifications. In brief, on standard U-bottomed microtiter plates, wild-type and mutant pneumolysin proteins were twofold serially diluted in TBS (15 mM Tris, 0.15 M NaCl, pH 7.5) plus 1 mM DTT as cofactor, in a final volume of 100 μl. One hundred microliters of 1% sheep erythrocyte suspension in TBS were added and the reaction conducted at 37° C. for 30 minutes. After spinning down the unlysed cells, the extent of the erythrocyte lysis was monitored in the supernatant at 405 nm using a microtiter plate reader. The end point of the assay was taken as the well in which 50% of erythrocytes were lysed, based on a 0.5% cell suspension lysed hypotonically.

Hemolysis Inhibition Assay of Murine Antisera

Figure 12:
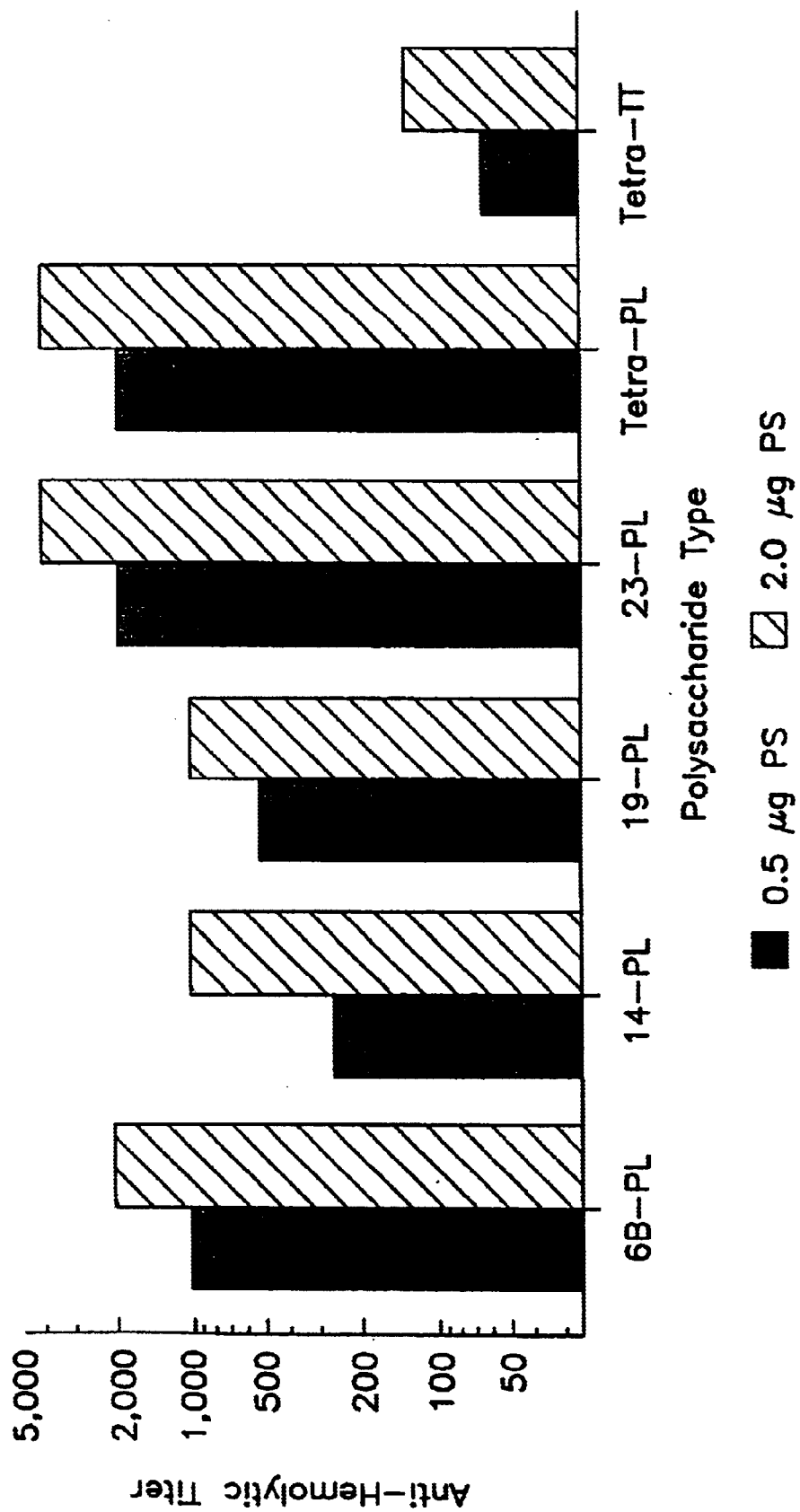
FIG. 12: Anti-hemolytic pneumolysoid-specific activity elicited by monovalent and tetravalent pneumococcal conjugates in mice after three injections.

Inhibition of the hemolytic activity was tested according to Paton et al. (1993) Infect. Immun. 40:548, with some variations. Before dilution, the mouse antisera were treated twice with chloroform, to eliminate cholesterol. A twofold serial dilution of 50 μl of the mice antisera were performed and 50 μl of toxin stock solution at 4HU (hemolytic units) were added. The hemolytic activity of the toxins were assessed immediately before the neutralization assay. After 15 min incubation at 37° C. to allow serum antibody to bind to the pneumolysin, 100 μl sheep red blood (1% in TBS) (ICN, Costa Mesa, Calif.) was added in each well. The plates were incubated 30 min at 37° C. and the unlysed cells were pelleted by centrifugation. The extent of the erythrocyte lysis released in the supernatant was monitored at 405 nm using a microtiter plate reader. The antibody titers were taken as the highest dilutions of sera which gave complete inhibition of the hemolysis (FIG. 12).

Hemolysis Inhibition Assay by Modified Pneumolysin

Figure 13:
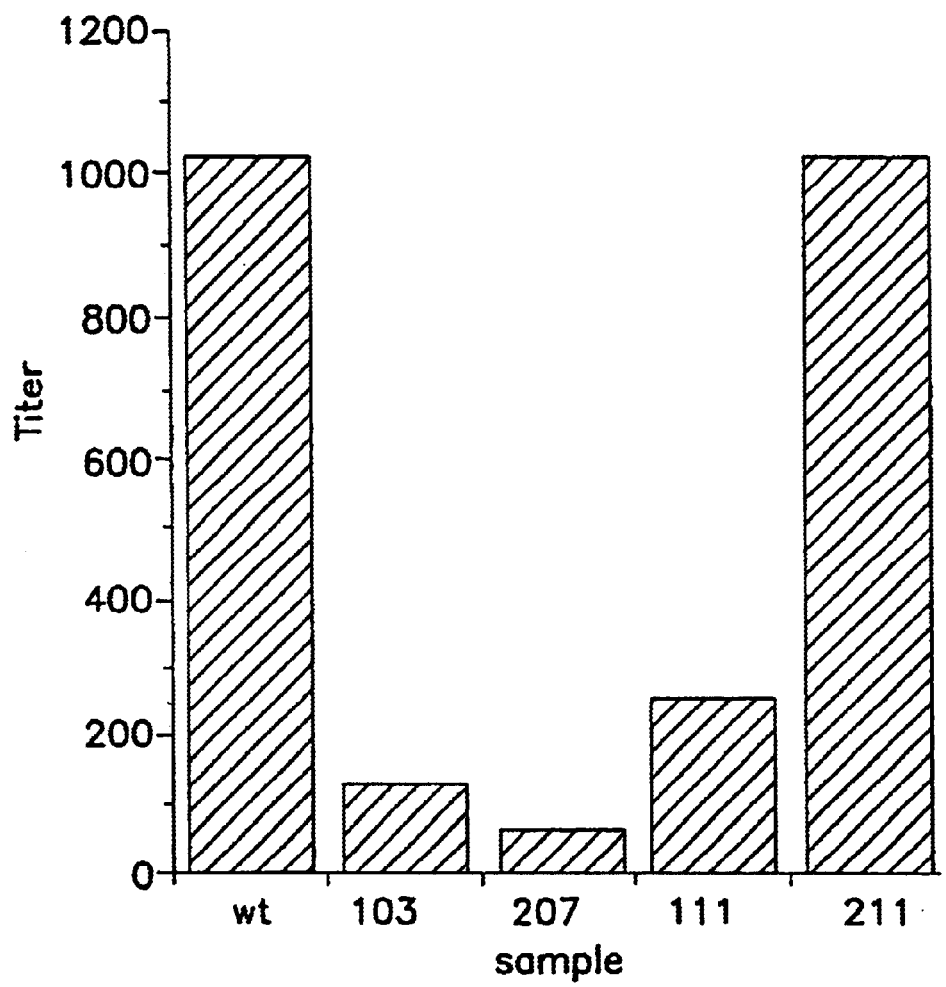
FIG. 13: Hemolysis Inhibition Assay. Hemolysis titer of wild type pneumolysin upon pre-incubation with the indicated mutants. The bars represent the final hemolytic titer of the wild type tested against erythrocytes pre-treated with the indicated mutants.
Figure 14:
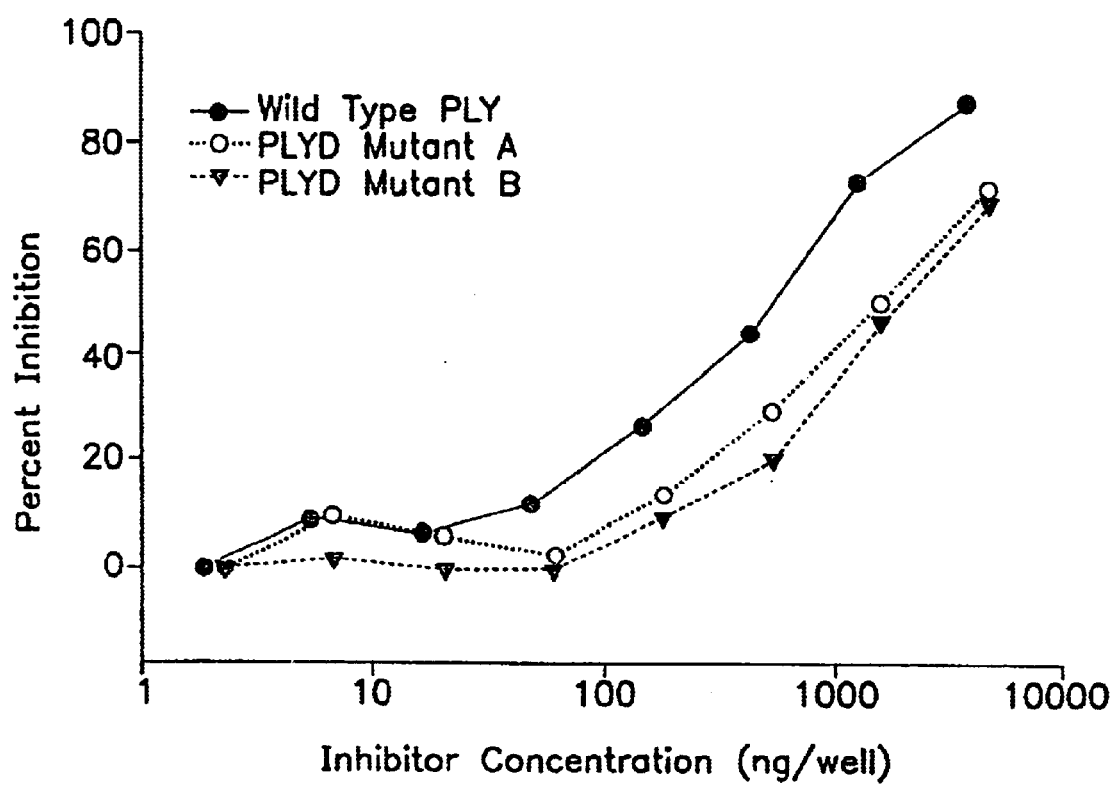
FIG. 14: Competitive inhibition ELISA studies between a rabbit polyclonal antibody to wild type PLY and wild type PLY protein using soluble wild type PLY, PLYD mutant pNV207 (A) and PLYD mutant pNV103 (B).

Modified pneumolysin polypeptides can be tested for their ability to inhibit the hemolytic activity of wild-type pneumolysin when pre-incubated with erythrocytes. A suspension of erythrocytes (3 ml) was incubated with 1 μl (1 mg/ml) of each of the modified pneumolysin polypeptides for 10 min and the suspension added to wells of a microtiter plate containing serial dilutions of wild-type pneumolysin. The plate was incubated at 37° C. for 30 min and the hemolytic titer compared with a control incubation performed with normal erythrocytes. The selected mutants exert variable degrees of inhibition of the wild type hemolytic activity upon pre-incubation with erythrocytes (FIG. 13), suggesting that these mutants are capable of competing with the wild type for the binding site, but are unable to insert into membranes to form lytic channels. The mutants pNV103 and pNV207 represent the most effective inhibitors, followed by pNV111. The mutant pNV211 apparently does not exhibit such inhibition properties. Additional corroboration of the structural integrity and identity of the PLYD mutants is that most of their antigenicity is retained when compared to native PLY as shown in FIG. 14.

Circular Dichroism (CD) Spectroscopy

The secondary and tertiary structures of the free wild type and mutant pneumolysin and the respective conjugate were evaluated by circular dichroism (CD) spectroscopy in the far UV (180 to 250 nm) and near UV (250 to 350 nm) regions, respectively. Concentrated stock solutions of protein were dialyzed exhaustively against a buffer system comprised of 10 mM $NaPO_4$ (pH 8.0). Spectra of samples containing 1.0 mg/ml protein were recorded at 0.1 nm wavelength intervals on a JASCO Model 710 circular dichroism spectropolarimeter (JASCO, Easton, Md.) employing a scan speed of 5 nm/min and average response time of 1 s. A minimum of four consecutive scans were accumulated and the average spectra stored. The temperature of the samples was maintained at 25° C. through the use of water-jacketed 0.01 cm and 1.0 cm pathlength cells in the far and near UV, respectively.

Fluorescence Spectroscopy

Fluorescence measurements were performed on an SLM AMINCO-Bowman 8100 Series 2 spectrofluorometer. Fluorescence spectra of samples containing 100 μg/ml protein in 10 mM $NaPO_4$ (pH 7.5) were recorded over the range of 300 to 500 nm employing an excitation wavelength of 290 nm and slit widths of 2 nm. Temperature stability was maintained through use of a water-jacketed 1.0 cm quartz cuvette thermostatted at 25° C.

Figure 15:
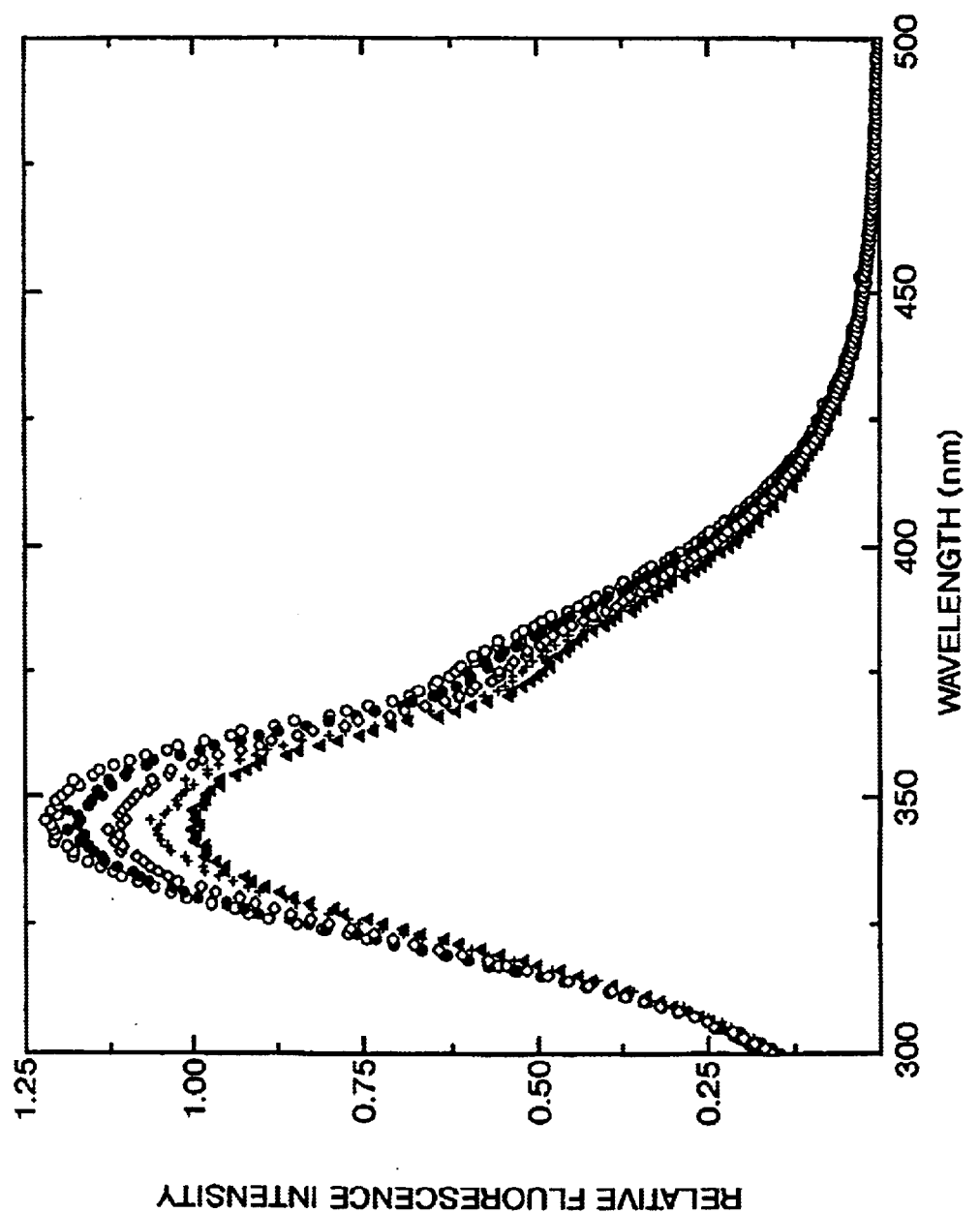
FIG. 15: Fluorescence Spectra of Wild Type Pneumolysin and Mutants. Fluorescence emission spectra of wild type pneumolysin and selected mutants recorded in 10 mM sodium phosphate (pH 7.5) employing an excitation wavelength of 290 nm and monochromator slits of 2 nm. ○ represents pNV207, • represents pNV111, ◇ represents pNV211, + represents pNV103, and □ represents wild-type.
Figure 16:
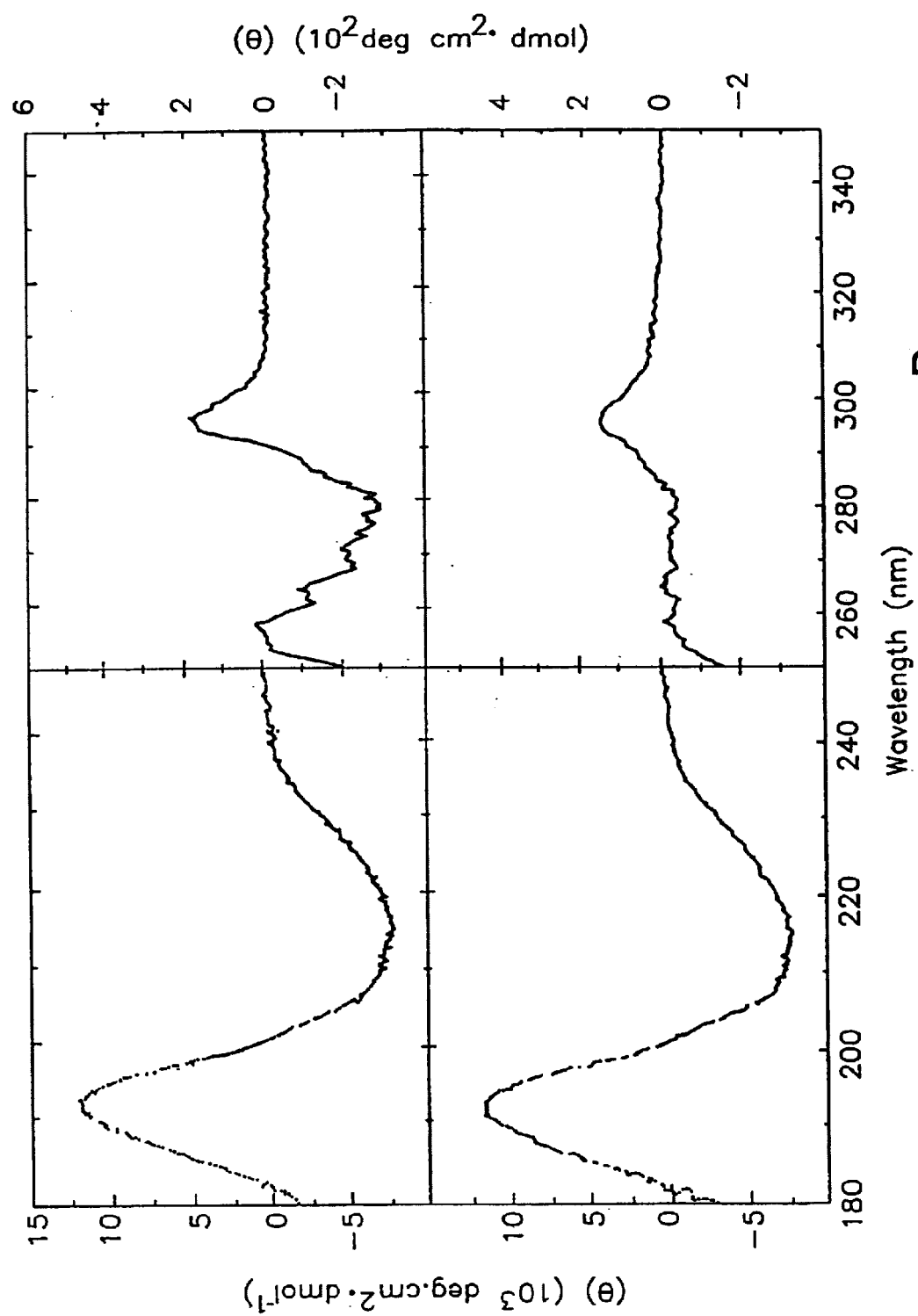
FIG. 16: (A) Far UV CD spectra of mutant pneumolysin pNV207(upper chart) and type 14 CPS conjugated mutant pneumolysin pNV207(lower chart); (B) near UV CD spectra of mutant pneumolysin pNV207(upper chart) and type 14 CPS conjugated mutant pneumolysin pNV207 (lower chart).
Figure 17A:
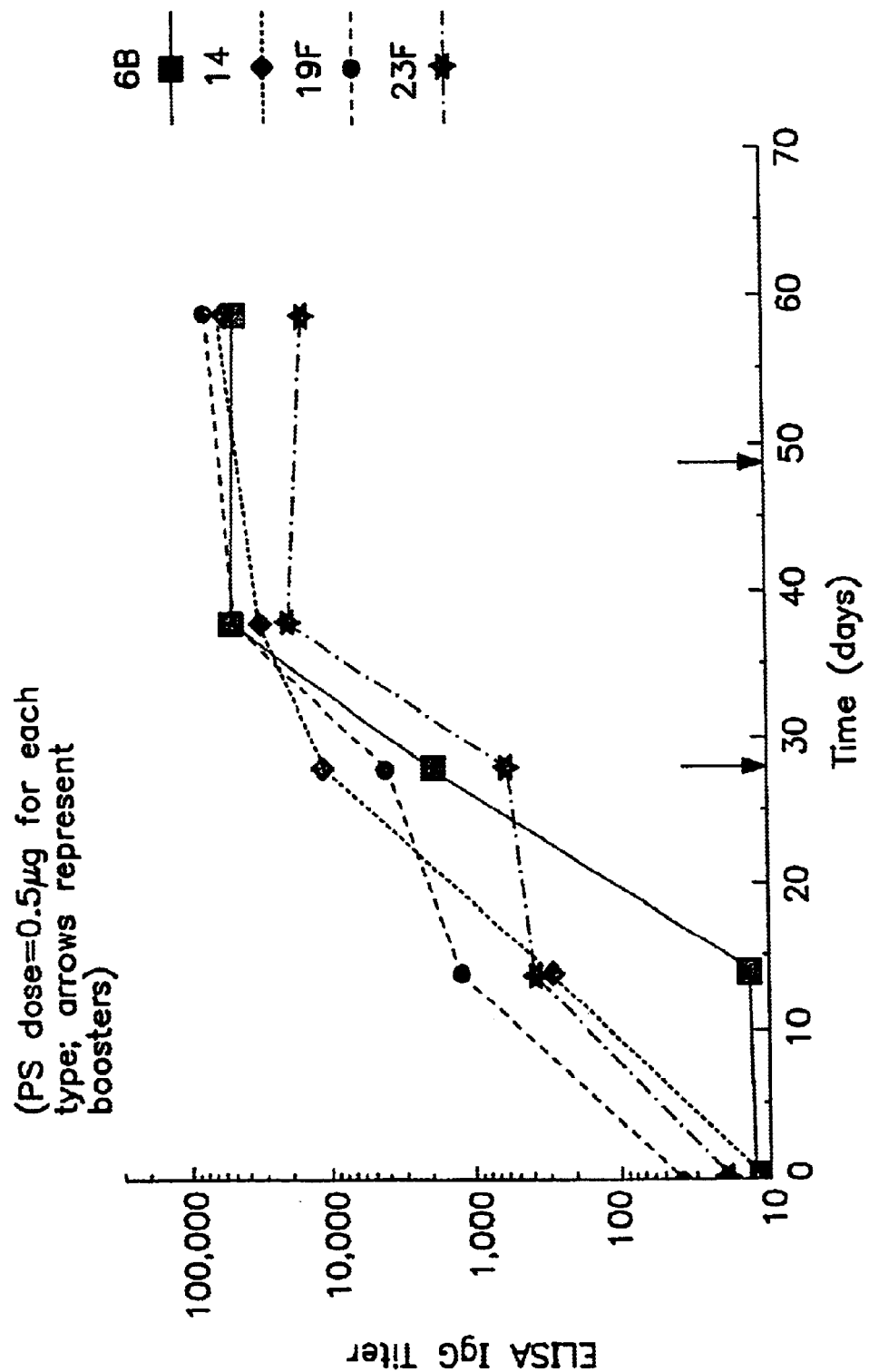
FIG. 17: (A) Tetravalent pneumococcal pneumolysoid pNV207 conjugate vaccine in mice: polysaccharide-specific IgG response over time; (B) tetravalent pneumococcal TT conjugate vaccine in mice: polysaccharide-specific IgG response over time; (C) monovalent pneumococcal pneumolysoid pNV207 conjugate vaccines in mice: polysaccharide-specific IgG response over time.
Figure 17B:
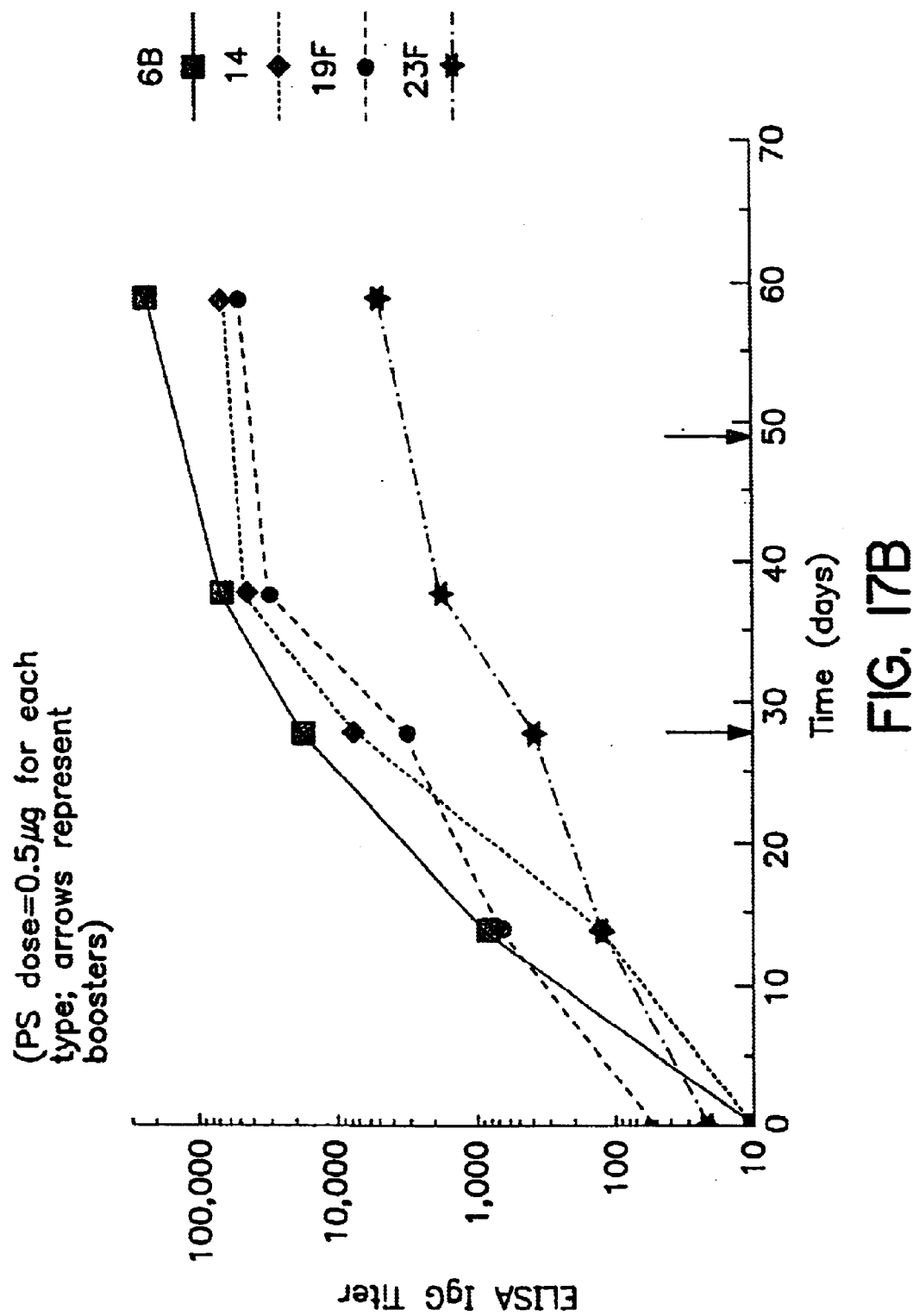
Figure 17C:
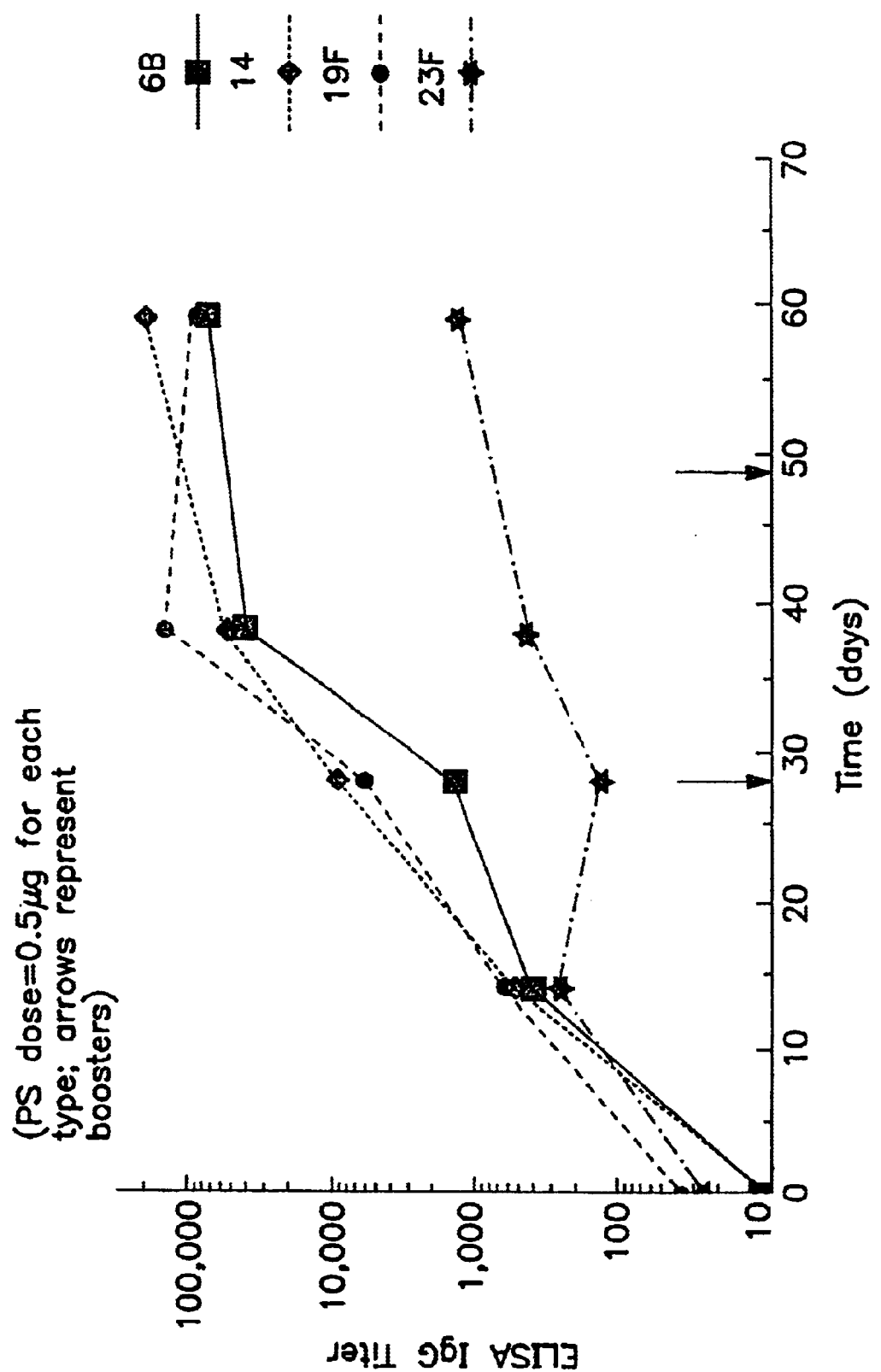

A comparison of the fluorescence spectra of wild type pneumolysin and selected mutants has been performed under experimental conditions in which these proteins adopt a native folded conformation. As evidenced in FIG. 15, the fluorescence spectra of all the proteins are characterized by a maximum emission intensity at ~345 nm, with somewhat higher amplitudes observed for the mutant proteins when compared to the wild type. Overall, the results indicate that all the proteins are in a native conformation, which is characterized by a significant number of Trp residues exposed to solvent. These results have been observed previously for perfringolysin, and are consistent with the presence of a Trp-rich cell-binding domain in the C-terminus of these cytolysins.

Basic Structural and Immunological Features of Pneumolysin (PLY), Pneumolysoid (PLYD) and CPS-PLYD Conjugates as Assessed by Circular Dichroism PLY overexpressed in *E. coli* and refolded from inclusion bodies exhibits a typical far UV CD spectrum characteristic of a high content of β-sheets with a minimum observed at ~215 nm (Minetti et al. *Biophys. J.,* 1998, 74, A233) which does not significantly change in the single point mutation PLYD. Likewise, chemical conjugation of either PLY or PLYD with PnCPS does not affect the overall secondary structure of the proteins (FIG. 16A). The near UV CD spectrum (FIG. 16B) which derives from the relative assymetry of tyrosyl and tryptophanyl residues in the protein has also been assessed in the free versus conjugate protein and reveals a highly ordered structure resembling the wild type free protein. The conjugate, however exhibits minor changes in the near UV CD profile as a result from the presence of the polysaccharide on the surface of these complexes, interfering particularly with the specific Tyr signal (i.e., negative ellipticity with a minimum centered at ~280 nm), reduced in the respective conjugate. Additional corroboration of the structural integrity and identity of the PLYD mutants is that most of their antigenicity is retained when compared to native PLY as shown in FIG. 14.

Spectroscopic methods represent a powerful tool in the evaluation of the integrity of proteins. In the particular case of conjugate vaccines which employ proteins as carriers, these methods, in conjunction with functional and immunological techniques may facilitate monitoring batch-to-batch variations as well as the molecular basis for vaccine efficacy (Crane et al. *Eur. J. Biochem.* 1997, 246, 320–327; Jones et al. *Dev. Biol. Stand.* 1996, 87, 143–151). The mutations render the protein atoxic, but it retains the ability to refold to a native-like structure, indistinguishable from the parent molecule. The nearly superimposable far UV CD spectra of the free mutant protein (i.e., pNV207) and the corresponding Pn 14 conjugate, as seen by both amplitude and crossover points, are indications that the secondary structure of the protein within this macromolecular complex remains intact. These results contrast with previous studies conducted with other polysaccharide-protein conjugates in which light variations in the secondary structure were noticeable, following conjugation (Crane et al. *Eur. J. Biochem.* 1997, 246, 320–327).

The tyrosyl residues in the vicinity of the conjugation sites may be perturbed by the presence of the polysaccharide as indicated by the differences observed in the near UV CD spectra in the region around 280 nm. However, the tryptophanyl peak, characteristic at 290 nm, remains unaffected by the conjugation, another indication that the Tyr-containing regions are not affected by the reductive amination procedure.

Overall the spectroscopic in conjunction with the serological results provide excellent evidence that PLYD-CPS conjugates represent suitable vaccine candidates for the prevention of pneumococcal diseases.

Immunogenicity Time Course Studies

An immunogenicity time course study for the tetravalent PLYD-PnCPS was carried out and is shown in FIG. 17A. The animals received three injections at days 0, 28 and 49, and blood samples were obtained at days 0, 14, 28, 38, and 59. Each dose contained 0.5 μg PnCPS of each type. The PnCPS-specific IgG response to each type increased over time to peak just after the second injection (titers ranging between 20,000 and 50,000) and then reached a plateau. Significant booster effects were observed after the second injection.

In FIG. 17B is shown the time course of the PnCPS-specific IgG response of the tretravalent TT conjugate. Like for the PLYD combination vaccine, the animals were similarly immunized using the same schedule and same dose of vaccine. Again, the IgG response to each type polysaccharide increased after each injection with similar magnitude (final titers between 50,000 and 200,000) except for type 23F which gave a significantly lower titer (ca: 5,000). Booster effects were also observed for each type after the second injection, except for 23 which gave a much less pronounced effect.

For comparison with the above PLYD-PnCPS combination vaccine, the immunogenicity time course of the monovalent PLYD-PnCPS conjugates are shown in FIG. 17C. The animals received the same doses of 0.5 μg of PnCPS and had the same immunization schedule as mentioned above. The time course of the IgG response to the PnCPS in those monovalent conjugates was almost identical to the one observed for the combination except for the type 23 PnCPS which gave rise to a less steeper time course curve, with antibody titers an order of magnitude lower than those of the three other types.

The preclinical studies demonstrate that conjugates consisting of polysaccharides derived from four pneumococcal strains (6, 14, 19, and 23) and PLYD are highly immunogenic in animals, and they elicited PnCPS-specific antibodies titers which compared well with those raised with a TT tetravalent conjugate. In addition, the PLYD tetravalent conjugate was able to generate high levels of PLY-specific IgG antibodies that neutralized hemolytic activity of wild type PLY. In the light of a recently published report on the clear pathogenic role of PLY in the hearing loss and cochlear damage in a pneumococcal experimental meningitis model, it is clear that PLYD vaccine-induced antibodies will be a useful adjunct to the capsular antibodies to ameliorate or even prevent the feared complications associated with otitis media (Winter et al. *Infection and Immunity* 1997, 65, 4411–4418).

We claim:

1. A modified pneumolysin polypeptide comprising one or more amino acid substitutions in a wild type pneumolysin polypeptide having the amino acid sequence SEQ ID NO:3, wherein said one amino acid substitution occurs at a position selected from the group consisting of positions 61, 148, and 195, or wherein said more than one amino acid substitutions occur at positions selected from the group consisting of 17, 18, 33, 41, 45, 46, 61, 63, 66, 83, 101, 102, 128, 148, 189, 195, 239, 243, 255, and 257, and wherein said modified pneumolysin polypeptide is soluble, elicits antibodies which are cross-reactive with wild-type pneumolysin, and has attenuated hemolytic activity.

2. The modified pneumolysin polypeptide according to claim 1, wherein the hemolytic activity is less than 25% compared to the hemolytic activity of the wild-type pneumolysin.

3. The modified pneumolysin polypeptide according to claim 2, wherein the hemolytic activity is less than 1% compared to the hemolytic activity of the wild-type pneumolysin.

4. The modified pneumolysin polypeptide according to claim 1, wherein the polypeptide is selected from the group consisting of pNVJ1, pNVJ22, pNVJ56, pNV103, pNV207, pNV111, and pNV211.

5. The modified pneumolysin polypeptide according to claim 1, wherein the modified pneumolysin polypeptide is conjugated to a polysaccharide which elicits antibodies cross-reactive with a bacterial polysaccharide.

6. The modified pneumolysin polypeptide conjugated to a polysaccharide according to claim 5, wherein the polysaccharide is from a bacterium selected from the group consisting of *Haemophilus influenzae* type b; meningococcus group A, B or C; group B streptococcus type Ia, Ib, II, III, V or VIII; and one or more of serotypes 1–23 of *S. pneumoniae*.

7. A vaccine comprising the modified pneumolysin polypeptide according to claim 1 and a pharmaceutically acceptable carrier.

8. The vaccine according to claim 7, wherein the polypeptide is conjugated to a polysaccharide which elicits antibodies cross-reactive with a bacterial polysaccharide.

9. The vaccine according to claim 8, wherein the bacterial polysaccharide is from a bacterium selected from the group consisting of *Haemophilus influenzae* type b; meningococcus group A, B, or C; group A streptococcus or group B streptococcus type Ia, Ib, II, III, V, or VIII; and one or more of serotypes 1–23 of *S. pneumoniae*.

10. The modified pneumolysin polypeptide according to claim 1, wherein said one amino acid substitution at position 61 is a proline or substitution.

11. The modified pneumolysin polypeptide according to claim 1, wherein said one amino acid substitution at position 148 is a lysine, substitution.

12. The modified pneumolysin polypeptide according to claim 1, wherein said one amino acid substitution at position 195 is a valine or isoleucine substitution.

13. The modified pneumolysin polypeptide according to claim 1, wherein said amino acid substitution at position 243 is an arginine, valine, glutamic acid, or serine substitution.

14. The modified pneumolysin polypeptide according to claim 1, wherein the modification of the polypeptide comprises a combination of substitutions at positions 17, 18, 61, 66 and 101.

15. The modified pneumolysin polypeptide according to claim 14, wherein the substitutions consist of arginine at position 17, asparagine at position 18, proline at position 61, tyrosine at position 66, and threonine at position 101.

16. The modified pneumolysin polypeptide according to claim 1, wherein the modification of the polypeptide comprises a combination of substitutions at positions 41, 195 and and an additional substitution at position 172.

17. The modified pneumolysin polypeptide according to claim 16, wherein the substitutions consist of glycine at position 41, isoleucine at position 195, glycine at position 255, and alanine at position 172.

18. The modified pneumolysin polypeptide according to claim 17, wherein the modified pneumolysin polypeptide is pNVJ45.

19. The modified pneumolysin polypeptide according to claim 1, wherein the modification of the polypeptide comprises a combination of substitutions at positions 63, 128 and 148.

20. The modified pneumolysin polypeptide according to claim 19, wherein the substitutions consist of serine at position 63, histidine at position 128, 148, and glutamic acid at position 127.

21. The modified pneumolysin polypeptide according to claim 20, wherein the modified pneumolysin polypeptide is pNVJ20.

22. The modified pneumolysin polypeptide according to claim 1, wherein the modification of the polypeptide comprises a combination of substitutions at positions 33, 46, 83, 239 and 257.

23. The modified pneumolysin polypeptide according to claim 22, wherein the substitutions consist of threonine at position 33, threonine at position 46, serine at position 83, arginine at position 239 and glycine at position 257.

24. The modified pneumolysin polypeptide according to claim 1, wherein the modification of the polypeptide comprises a combination of substitutions at positions 45, 102, 189 and 195.

25. The modified pneumolysin polypeptide according to claim 24, wherein the substitutions consist of alanine at position 45, glycine at position 102, arginine at position 189, and valine at position 195.

26. Modified pneumolysin polypeptide pNVJ1.

27. Modified pneumolysin polypeptide pNVJ20.

28. Modified pneumolysin polypeptide pNVJ22.

29. Modified pneumolysin polypeptide pNVJ45.

30. Modified pneumolysin polypeptide pNVJ56.

31. Modified pneumolysin polypeptide pNV103.

32. Modified pneumolysin polypeptide pNV207.

33. Modified pneumolysin polypeptide pNV111.

34. Modified pneumolysin polypeptide pNV211.

* * * * *

SEQUENCE LISTING

```
(1) GENERAL INFORMATION:

(iii) NUMBER OF SEQUENCES:  18

(2) INFORMATION FOR SEQ ID NO:1:

(i) SEQUENCE CHARACTERISTICS:
          (A) LENGTH:  1413
          (B) TYPE:  nucleic acid
          (C) STRANDEDNESS:  double
          (D) TOPOLOGY:  linear (ii) MOLECULE TYPE:  cDNA (vi) ORIGINAL SOURCE:
          (A) ORGANISM: S. pneumoniae (xi) SEQUENCE DESCRIPTION: SEQ ID NO:1:

atggcaaata aagcagtaaa tgactttata ctagctatga                              40
attacgataa aaagaaactc ttgacccatc agggagaaag                              80
tattgaaaat cgtttcatca aagagggtaa tcagctaccc                             120
```

| | |
|---|---|
| gatgagtttg ttgttatcga agaaagaag cggagcttgt | 160 |
| cgacaaatac aagtgatatt tctgtaacag ctaccaacga | 200 |
| cagtcgcctc tatcctggag cacttctcgt agtggatgag | 240 |
| accttgttag agaataatcc cactcttctt gcggtcgatc | 280 |
| gtgctccgat gacttatagt attgatttgc ctggtttggc | 320 |
| aagtagcgat agctttctcc aagtggaaga tcccagcaat | 360 |
| tcaagtgttc gcggagcggt aaacgatttg ttggctaagt | 400 |
| ggcatcaaga ttatggtcag gtcaataatg tcccagctag | 440 |
| aatgcagtat gaaaaaatca cggctcacag catggaacaa | 480 |
| ctcaaggtca agtttggttc tgactttgaa aagacaggga | 520 |
| attctcttga tattgatttt aactctgtcc attcaggcga | 560 |
| aaagcagatt cagattgtta attttaagca gatttattat | 600 |
| acagtcagcg tagacgctgt taaaaatcca ggagatgtgt | 640 |
| ttcaagatac tgtaacggta gaggatttaa acagagagg | 680 |
| aatttctgca gagcgtcctt tggtctatat ttcgagtgtt | 720 |
| gcttatgggc gccaagtcta tctcaagttg gaaaccacga | 760 |
| gtaagagtga tgaagtagag gctgcttttg aagctttgat | 800 |
| aaaaggagtc aaggtagctc ctcagacaga gtggaagcag | 840 |
| attttggaca atacagaagt gaaggcggtt attttagggg | 880 |
| gcgacccaag ttcgggtgcc cgagttgtaa caggcaaggt | 920 |
| ggatatggta gaggacttga ttcaagaagg cagtcgcttt | 960 |
| acagcagatc atccaggctt gccgatttcc tatacaactt | 1000 |
| ctttttttacg tgacaatgta gttgcgacct ttcaaaatag | 1040 |
| tacagactat gttgagacta aggttacagc ttacagaaac | 1080 |
| ggagatttac tgctggatca tagtggtgcc tatgttgccc | 1120 |
| aatattatat tacttggaat gaattatcct atgatcatca | 1160 |
| aggtaaggaa gtcttgactc ctaaggcttg ggacagaaat | 1200 |
| gggcaggatt taacggctca ctttaccact agtattcctt | 1240 |
| taaaagggaa tgttcgtaat ctctctgtca aaattagaga | 1280 |
| gtgtaccggg cttgcttggg aatggtggcg tacggtttat | 1320 |
| gaaaaaaccg atttgccact agtgcgtaag cggacgattt | 1360 |
| ctatttgggg aacaactctc tatccgcagg tagaagataa | 1400 |
| ggtagaaaat gac | 1413 |

(2) INFORMATION FOR SEQ ID NO:2:

(i) SEQUENCE CHARACTERISTICS:
        (A) LENGTH: 1413
        (B) TYPE: nucleic acid
        (C) STRANDEDNESS: double
        (D) TOPOLOGY: linear (ii) MOLECULE TYPE: cDNA (vi) ORIGINAL SOURCE:
   (A) ORGANISM: S. pneumoniae (xi) SEQUENCE DESCRIPTION: SEQ ID NO:2:

| | |
|---|---:|
| atggcaaata aagcagtaaa tgactttata ctagctatga | 40 |
| attacgatan aaanaaactc ttgacccatc agggagaaag | 80 |
| tattgaaaat cgtttcanca aagagggtaa tcagctaccc | 120 |
| gntgagtttg ttgntancga aagaaagaag cggagcttgt | 160 |
| cgacaaatac aagtgatatt nctgtancag ctaccnacga | 200 |
| cagtcgcctc tatcctggag cacttctcgt agtggatgag | 240 |
| accttgtnag agaataatcc cactcttctt gcggtngatc | 280 |
| gtgctccgat gacttatagt antgntttgc ctggtttggc | 320 |
| aagtagcgat agctttctcc aagtggaaga ncccagcaat | 360 |
| tcaagtgttc gcggagcggn anacgatttg ttggctaagt | 400 |
| ggcatcaaga ttatggtcag gtcaataatg tcccagctag | 440 |
| aangcagtat gaaaaaatna cggctcacag catggaacaa | 480 |
| ctcaaggtca agtttggttc tgactttgaa aagncaggga | 520 |
| attctcttga tattgatttt aactctgtcc attcaggnga | 560 |
| aaagcngatt cagattgtta atnttaagca gatttattat | 600 |
| acagtcagcg tagacgctgt taaaaatcca ggagatgtgt | 640 |
| ttcaagatac tgtaacggta gaggatttaa aacagagagg | 680 |
| aatttctgca gagcgtcctt tggtctatat ttcgagngtt | 720 |
| gcttatgggc gccaagtcta tctcaagttg aaaccacga | 760 |
| gtangagtgn tgaagtagag gctgcttttg aagctttgat | 800 |
| aaaaggagtc aaggtagctc ctcagacaga gtggaagcag | 840 |
| attttggaca atacagaagt gaaggcggtt attttagggg | 880 |
| gcgacccaag ttcgggtgcc cgagttgtaa caggcaaggt | 920 |
| ggatatggta gaggacttga ttcaagaagg cagtcgcttt | 960 |
| acagcagatc atccaggctt gccgatttcc tatacaactt | 1000 |
| cttttttacg tgacaatgta gttgcgacct ttcaaaanag | 1040 |
| tacagactat gttgagacta aggttacagc ttacagaaac | 1080 |
| ggagatttac tgctggatca tagtggtgcc tatgttgccc | 1120 |
| aatattatat tacttggnat gaattatcct atgatcatca | 1160 |
| aggtaaggaa gtcttgactc ctaaggcttg ggacagaaat | 1200 |
| gggcaggatt tnacggctca ctttaccact agtattcctt | 1240 |
| taaaagggaa tgttcgtaat ctctctgtca aaattagaga | 1280 |
| gtgtaccggg cttgcntggg aatggtggcg tacggtttat | 1320 |
| gaaaaaaccg atttgccact agtgcgtaag cggacgattt | 1360 |
| ctatttgggg aacaactctc tatccncagg tagangataa | 1400 |
| ggtagaaaat gac | 1413 |

```
(2) INFORMATION FOR SEQ ID NO:3:

(i) SEQUENCE CHARACTERISTICS:
        (A) LENGTH: 471
        (B) TYPE: amino acid
        (C) STRANDEDNESS: unknown
        (D) TOPOLOGY: linear (ii) MOLECULE TYPE: amino acid (vi) ORIGINAL SOURCE:
        (A) ORGANISM: S. pneumoniae (xi) SEQUENCE DESCRIPTION: SEQ ID NO:3:

Met Ala Asn Lys Ala Val Asn Asp Phe Ile Leu Ala
1               5                   10

Met Asn Tyr Asp Lys Lys Lys Leu Leu Thr His Gln
            15                  20

Gly Glu Ser Ile Glu Asn Arg Phe Ile Lys Glu Gly
        25              30                  35

Asn Gln Leu Pro Asp Glu Phe Val Val Ile Glu Arg
                40                  45

Lys Lys Arg Ser Leu Ser Thr Asn Thr Ser Asp Ile
        50              55                  60

Ser Val Thr Ala Thr Asn Asp Ser Arg Leu Tyr Pro
                65                  70

Gly Ala Leu Leu Val Val Asp Glu Thr Leu Leu Glu
                75                  80

Asn Asn Pro Thr Leu Leu Ala Val Asp Arg Ala Pro
85                      90                  95

Met Thr Tyr Ser Ile Asp Leu Pro Gly Leu Ala Ser
                100             105

Ser Asp Ser Phe Leu Gln Val Glu Asp Pro Ser Asn
        110             115                 120

Ser Ser Val Arg Gly Ala Val Asn Asp Leu Leu Ala
                125             130

Lys Trp His Gln Asp Tyr Gly Gln Val Asn Asn Val
            135                 140

Pro Ala Arg Met Gln Tyr Glu Lys Ile Thr Ala His
145                 150                 155

Ser Met Glu Gln Leu Lys Val Lys Phe Gly Ser Asp
                160             165

Phe Glu Lys Thr Gly Asn Ser Leu Asp Ile Asp Phe
        170             175                 180

Asn Ser Val His Ser Gly Glu Lys Gln Ile Gln Ile
                185             190

Val Asn Phe Lys Gln Ile Tyr Tyr Thr Val Ser Val
            195                 200

Asp Ala Val Lys Asn Pro Gly Asp Val Phe Gln Asp
205                 210                 215

Thr Val Thr Val Glu Asp Leu Lys Gln Arg Gly Ile
                220             225

Ser Ala Glu Arg Pro Leu Val Tyr Ile Ser Ser Val
        230             235                 240

Ala Tyr Gly Arg Gln Val Tyr Leu Lys Leu Glu Thr
                245             250
```

-continued

```
Thr Ser Lys Ser Asp Glu Val Glu Ala Ala Phe Glu
        255                 260

Ala Leu Ile Lys Gly Val Lys Val Ala Pro Gln Thr
265                 270                 275

Glu Trp Lys Gln Ile Leu Asp Asn Thr Glu Val Lys
            280                 285

Ala Val Ile Leu Gly Gly Asp Pro Ser Ser Gly Ala
290                 295                 300

Arg Val Val Thr Gly Lys Val Asp Met Val Glu Asp
            305                 310

Leu Ile Gln Glu Gly Ser Arg Phe Thr Ala Asp His
        315                 320

Pro Gly Leu Pro Ile Ser Tyr Thr Thr Ser Phe Leu
325                 330                 335

Arg Asp Asn Val Val Ala Thr Phe Gln Asn Ser Thr
                340                 345

Asp Tyr Val Glu Thr Lys Val Thr Ala Tyr Arg Asn
        350                 355                 360

Gly Asp Leu Leu Leu Asp His Ser Gly Ala Tyr Val
                365                 370

Ala Gln Tyr Tyr Ile Thr Trp Asn Glu Leu Ser Tyr
        375                 380

Asp His Gln Gly Lys Glu Val Leu Thr Pro Lys Ala
385                 390                 395

Trp Asp Arg Asn Gly Gln Asp Leu Thr Ala His Phe
                400                 405

Thr Thr Ser Ile Pro Leu Lys Gly Asn Val Arg Asn
        410                 415                 420

Leu Ser Val Lys Ile Arg Glu Cys Thr Gly Leu Ala
                425                 430

Trp Glu Trp Trp Arg Thr Val Tyr Glu Lys Thr Asp
            435                 440

Leu Pro Leu Val Arg Lys Arg Thr Ile Ser Ile Trp
445                 450                 455

Gly Thr Thr Leu Tyr Pro Gln Val Glu Asp Lys Val
                460                 465

Glu Asn Asp
        470
```

(2) INFORMATION FOR SEQ ID NO:4:

(i) SEQUENCE CHARACTERISTICS:
        (A) LENGTH: 471
        (B) TYPE: amino acid
        (C) STRANDEDNESS: unknown
        (D) TOPOLOGY: linear (ii) MOLECULE TYPE: amino acid (vi) ORIGINAL SOURCE:
        (A) ORGANISM: S. pneumoniae (xi) SEQUENCE DESCRIPTION: SEQ ID NO:4:

```
Met Ala Asn Lys Ala Val Asn Asp Phe Ile Leu Ala
1               5                   10

Met Asn Tyr Asp Xaa Xaa Lys Leu Leu Thr His Gln
        15                  20
```

-continued

Gly Glu Ser Ile Glu Asn Arg Phe Xaa Lys Glu Gly
 25                  30                  35

Asn Gln Leu Pro Xaa Glu Phe Val Xaa Xaa Glu Arg
             40                  45

Lys Lys Arg Ser Leu Ser Thr Asn Thr Ser Asp Ile
 50                  55                          60

Xaa Val Xaa Ala Thr Xaa Asp Ser Arg Leu Tyr Pro
                 65                  70

Gly Ala Leu Leu Val Val Asp Glu Thr Xaa Leu Glu
             75                  80

Asn Asn Pro Thr Leu Leu Ala Val Asp Arg Ala Pro
 85                  90                  95

Met Thr Tyr Ser Xaa Xaa Leu Pro Gly Leu Ala Ser
                 100                 105

Ser Asp Ser Phe Leu Gln Val Glu Asp Pro Ser Asn
         110                 115                 120

Ser Ser Val Arg Gly Ala Xaa Xaa Asp Leu Leu Ala
                 125                 130

Lys Trp His Gln Asp Tyr Gly Gln Val Asn Asn Val
             135                 140

Pro Ala Arg Xaa Gln Tyr Glu Lys Xaa Thr Ala His
145                 150                 155

Ser Met Glu Gln Leu Lys Val Lys Phe Gly Ser Asp
                 160                 165

Phe Glu Lys Xaa Gly Asn Ser Leu Asp Ile Asp Phe
         170                 175                 180

Asn Ser Val His Ser Gly Glu Lys Xaa Ile Gln Ile
                 185                 190

Val Asn Xaa Lys Gln Ile Tyr Tyr Thr Val Ser Val
             195                 200

Asp Ala Val Lys Asn Pro Gly Asp Val Phe Gln Asp
205                 210                 215

Thr Val Thr Val Glu Asp Leu Lys Gln Arg Gly Ile
                 220                 225

Ser Ala Glu Arg Pro Leu Val Tyr Ile Ser Xaa Val
         230                 235                 240

Ala Tyr Xaa Arg Gln Val Tyr Leu Lys Leu Glu Thr
                 245                 250

Thr Ser Xaa Ser Xaa Glu Val Glu Ala Ala Phe Glu
             255                 260

Ala Leu Ile Lys Gly Val Lys Val Ala Pro Gln Thr
265                 270                 275

Glu Trp Lys Gln Ile Leu Asp Asn Thr Xaa Val Lys
             280                 285

Ala Val Ile Leu Gly Gly Asp Pro Ser Ser Gly Ala
         290                 295                 300

Arg Val Val Thr Gly Lys Val Asp Met Val Glu Asp
                 305                 310

Leu Ile Gln Glu Gly Ser Arg Phe Thr Ala Asp His
             315                 320

Pro Gly Leu Pro Ile Ser Tyr Thr Thr Ser Phe Leu
325                 330                 335

```
Arg Asp Asn Val Val Ala Thr Phe Gln Asn Ser Thr
            340                 345

Asp Tyr Val Glu Thr Lys Val Thr Ala Tyr Arg Asn
    350             355                 360

Gly Asp Leu Leu Leu Asp His Ser Gly Ala Tyr Val
                365             370

Ala Gln Tyr Tyr Ile Thr Trp Xaa Glu Leu Ser Tyr
        375             380

Asp His Gln Gly Lys Glu Val Leu Thr Pro Lys Ala
385             390                 395

Trp Asp Arg Asn Gly Gln Asp Leu Thr Ala His Phe
            400             405

Thr Thr Ser Ile Pro Leu Lys Gly Asn Val Arg Asn
    410             415                 420

Leu Ser Val Lys Ile Arg Glu Cys Thr Gly Leu Ala
                425             430

Trp Glu Trp Trp Arg Thr Val Tyr Glu Lys Thr Asp
        435             440

Leu Xaa Leu Val Arg Lys Arg Thr Ile Ser Ile Trp
445             450                 455

Gly Thr Thr Leu Tyr Pro Gln Val Glu Asp Lys Val
            460             465

Glu Asn Asp
    470
```

(2) INFORMATION FOR SEQ ID NO:5:

(i) SEQUENCE CHARACTERISTICS:
        (A) LENGTH: 35
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: S. pneumoniae (xi) SEQUENCE DESCRIPTION: SEQ ID NO:5:

```
aaccttgatt gatctagata aggtatttat gttgg                            35
```

(2) INFORMATION FOR SEQ ID NO:6:

(i) SEQUENCE CHARACTERISTICS:
        (A) LENGTH: 33
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: S. pneumoniae (xi) SEQUENCE DESCRIPTION: SEQ ID NO:6:

```
tcttttgtc tctagaattc tcctctccta gtc                              33
```

(2) INFORMATION FOR SEQ ID NO:7:

(i) SEQUENCE CHARACTERISTICS:
        (A) LENGTH: 37
        (B) TYPE: nucleic acid

```
        (C) STRANDEDNESS:  single
        (D) TOPOLOGY:  linear (ii) MOLECULE TYPE:  DNA (vi) ORIGINAL SOURCE:
        (A) ORGANISM: S. pneumoniae (xi) SEQUENCE DESCRIPTION: SEQ ID NO:7:

tattaggagg agcatatggc aaataaagca gtaaatg                              37

(2) INFORMATION FOR SEQ ID NO:8:

(i) SEQUENCE CHARACTERISTICS:
        (A) LENGTH:  37
        (B) TYPE:  nucleic acid
        (C) STRANDEDNESS:  single
        (D) TOPOLOGY:  linear (ii) MOLECULE TYPE:  DNA (vi) ORIGINAL SOURCE:
        (A) ORGANISM: S. pneumoniae (xi) SEQUENCE DESCRIPTION: SEQ ID NO:8:

ggcctcttttt tgtctcgagc attctcctct cctagtc                             37

(2) INFORMATION FOR SEQ ID NO:9:

(i) SEQUENCE CHARACTERISTICS:
        (A) LENGTH:  21
        (B) TYPE:  nucleic acid
        (C) STRANDEDNESS:  single
        (D) TOPOLOGY:  linear (ii) MOLECULE TYPE:  nucleic acid (vi) ORIGINAL SOURCE:
        (A) ORGANISM: S. pneumoniae (xi) SEQUENCE DESCRIPTION: SEQ ID NO:9:

attacgcgac tcactatagg g                                               21

(2) INFORMATION FOR SEQ ID NO:10:

(i) SEQUENCE CHARACTERISTICS:
        (A) LENGTH:  21
        (B) TYPE:  nucleic acid
        (C) STRANDEDNESS:  single
        (D) TOPOLOGY:  linear (ii) MOLECULE TYPE:  DNA (vi) ORIGINAL SOURCE:
        (A) ORGANISM: S. pneumoniae (xi) SEQUENCE DESCRIPTION: SEQ ID NO:10:

attacgaaca ttccctttag g                                               21

(2) INFORMATION FOR SEQ ID NO:11:

(i) SEQUENCE CHARACTERISTICS:
        (A) LENGTH:  37
        (B) TYPE:  nucleic acid
        (C) STRANDEDNESS:  single
        (D) TOPOLOGY:  linear (ii) MOLECULE TYPE:  DNA
```

```
        (vi) ORIGINAL SOURCE:
              (A) ORGANISM: S. pneumoniae (xi) SEQUENCE DESCRIPTION: SEQ ID NO:11:

ggtcaggtca ataatgtccc agctagaaag cagtatg                                    37

(2) INFORMATION FOR SEQ ID NO:12:

(i) SEQUENCE CHARACTERISTICS:
              (A) LENGTH: 38
              (B) TYPE: nucleic acid
              (C) STRANDEDNESS: single
              (D) TOPOLOGY: linear (ii) MOLECULE TYPE: DNA (vi) ORIGINAL SOURCE:
              (A) ORGANISM: S. pneumoniae (xi) SEQUENCE DESCRIPTION: SEQ ID NO:12:

gctgtgagcc gtgatttttt catactgctt tctagctg                                   38

(2) INFORMATION FOR SEQ ID NO:13:

(i) SEQUENCE CHARACTERISTICS:
              (A) LENGTH: 38
              (B) TYPE: nucleic acid
              (C) STRANDEDNESS: single
              (D) TOPOLOGY: linear (ii) MOLECULE TYPE: DNA (vi) ORIGINAL SOURCE:
              (A) ORGANISM: S. pneumoniae (xi) SEQUENCE DESCRIPTION: SEQ ID NO:13:

gcagattcag attgttaatg ttaagcagat ttattata                                   38

(2) INFORMATION FOR SEQ ID NO:14:

(i) SEQUENCE CHARACTERISTICS:
              (A) LENGTH: 38
              (B) TYPE: nucleic acid
              (C) STRANDEDNESS: single
              (D) TOPOLOGY: linear (ii) MOLECULE TYPE: DNA (vi) ORIGINAL SOURCE:
              (A) ORGANISM: S. pneumoniae (xi) SEQUENCE DESCRIPTION: SEQ ID NO:14:

atctgcttaa cattaacaat ctgaatctgc ttttcgcc                                   38

(2) INFORMATION FOR SEQ ID NO:15:

(i) SEQUENCE CHARACTERISTICS:
              (A) LENGTH: 39
              (B) TYPE: nucleic acid
              (C) STRANDEDNESS: single
              (D) TOPOLOGY: linear (ii) MOLECULE TYPE: DNA (vi) ORIGINAL SOURCE:
              (A) ORGANISM: S. pneumoniae (xi) SEQUENCE DESCRIPTION: SEQ ID NO:15:

cagattgtta atattaagca gatttattat acagtcagc                                  39
```

-continued (2) INFORMATION FOR SEQ ID NO:16:

(i) SEQUENCE CHARACTERISTICS:
        (A) LENGTH: 39
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: S. pneumoniae (xi) SEQUENCE DESCRIPTION: SEQ ID NO:16:

aatctgctta atattaacaa tctgaatctg cttttcgcc        39

(2) INFORMATION FOR SEQ ID NO:17:

(i) SEQUENCE CHARACTERISTICS:
        (A) LENGTH: 39
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: S. pneumoniae (xi) SEQUENCE DESCRIPTION: SEQ ID NO:17:

acaagtgata ttcctgtaac agctaccaac gacagtcgc        39

(2) INFORMATION FOR SEQ ID NO:18:

(i) SEQUENCE CHARACTERISTICS:
        (A) LENGTH: 39
        (B) TYPE: nucleic acid
        (C) STRANDEDNESS: single
        (D) TOPOLOGY: linear (ii) MOLECULE TYPE: DNA (vi) ORIGINAL SOURCE:
        (A) ORGANISM: S. pneumoniae (xi) SEQUENCE DESCRIPTION: SEQ ID NO:18:

agctgttaca ggaatatcac ttgtatttgt cgacaagct        39